US007736680B2

(12) United States Patent
Lei et al.

(10) Patent No.: US 7,736,680 B2
(45) **Date of Patent: *Jun. 15, 2010**

(54) **USING MUTATIONS TO IMPROVE *ASPERGILLUS* PHYTASES**

(75) Inventors: Xingen Lei, Ithaca, NY (US); Edward J. Mullaney, New Orleans, LA (US); Abul Ullah, Slidell, LA (US)

(73) Assignees: Cornell Research Foundation, Inc., Ithaca, NY (US); The United States of America as Represented by the Secretary of Agriculture, Washington, DC (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/952,467

(22) Filed: Dec. 7, 2007

(65) Prior Publication Data

US 2009/0028994 A1 Jan. 29, 2009

(51) Int. Cl.
*A21D 2/00* (2006.01)
*C12N 9/16* (2006.01)
*C12N 5/04* (2006.01)
*C07H 21/04* (2006.01)

(52) U.S. Cl. ........................ 426/20; 435/196; 435/69.1; 536/23.2

(58) Field of Classification Search ....................... None
See application file for complete search history.

(56) References Cited

U.S. PATENT DOCUMENTS 3,819,528 A 6/1974 Berry
3,860,484 A 1/1975 O'Malley
3,966,971 A 6/1976 Morehouse et al.
4,038,140 A 7/1977 Jaworek et al.
4,375,514 A 3/1983 Siewert et al.
4,460,683 A 7/1984 Gloger et al.
4,470,968 A 9/1984 Mitra et al.
4,734,283 A 3/1988 Siren
4,765,994 A 8/1988 Holmgren
4,778,761 A 10/1988 Miyanohara et al.
4,914,029 A 4/1990 Caransa et al.
4,915,960 A 4/1990 Holmgren
4,950,609 A 8/1990 Tischer et al.
4,997,767 A 3/1991 Nozaki et al.
5,024,941 A 6/1991 Maine et al.
5,200,399 A 4/1993 Wettlaufer et al.
5,268,273 A 12/1993 Buckholz
5,290,765 A 3/1994 Wettlaufer et al.
5,316,770 A 5/1994 Edwards, Jr.
5,318,903 A 6/1994 Bewert et al.
5,366,736 A 11/1994 Edwards, Jr.
5,436,156 A 7/1995 Van Gorcom et al.
5,443,979 A 8/1995 Vanderbeke et al.
5,480,790 A 1/1996 Tischer et al.
5,492,821 A 2/1996 Callstrom et al.
5,516,525 A 5/1996 Edwards, Jr.
5,554,399 A 9/1996 Vanderbeke et al.
5,556,771 A 9/1996 Shen et al.
5,593,963 A 1/1997 Van Ooijen et al.
5,612,055 A 3/1997 Bedford et al.
5,691,154 A 11/1997 Callstrom et al.
5,716,655 A 2/1998 Hamstra et al.
5,736,625 A 4/1998 Callstrom et al.
5,780,292 A 7/1998 Nevalainen et al.
5,827,709 A 10/1998 Barendse et al.
5,830,696 A 11/1998 Short
5,830,733 A 11/1998 Nevalainen et al.
5,834,286 A 11/1998 Nevalainen et al.
5,853,779 A 12/1998 Takebe et al.
5,863,533 A 1/1999 Van Gorcom et al.
5,876,997 A 3/1999 Kretz
5,891,708 A 4/1999 Saniez et al.
5,900,525 A 5/1999 Austin-Phillips et al.
5,902,615 A 5/1999 Saniez et al.
5,935,624 A 8/1999 DeLuca et al.
5,955,448 A 9/1999 Colaco et al.
5,972,669 A 10/1999 Harz et al.
5,985,605 A 11/1999 Cheng et al.
5,989,600 A 11/1999 Nielsen et al.
6,022,555 A 2/2000 DeLuca et al.
6,039,942 A 3/2000 Lassen et al.
6,063,431 A 5/2000 Bae et al.

(Continued)

FOREIGN PATENT DOCUMENTS

CN 1126243 A 7/1996

(Continued)

OTHER PUBLICATIONS

Greiner et al., "Purification and Characterization of a Phytase from *Klebsiella terrigena*," Arch. Biochem. Biophys. 341 (2):201-206 (1997).

(Continued)

*Primary Examiner*—Ganapathirama Raghu
*Assistant Examiner*—Md. Younus Meah
(74) *Attorney, Agent, or Firm*—Nixon Peabody LLP

(57) ABSTRACT

The present invention relates to an isolated nucleic acid molecule encoding a mutant phytase and the isolated mutant phytase itself. The present invention further relates to methods of using the isolated nucleic acid molecule and the isolated mutant phytase of the present invention.

39 Claims, 34 Drawing Sheets

U.S. PATENT DOCUMENTS

| | | | |
|---|---|---|---|
| 6,083,541 | A | 7/2000 | Hamstra et al. |
| 6,110,719 | A | 8/2000 | Kretz |
| 6,139,892 | A | 10/2000 | Fredlund et al. |
| 6,139,902 | A | 10/2000 | Kondo et al. |
| 6,140,077 | A | 10/2000 | Nakamura et al. |
| 6,183,740 | B1 | 2/2001 | Short et al. |
| 6,190,897 | B1 | 2/2001 | Kretz |
| 6,204,012 | B1 | 3/2001 | Hellmuth et al. |
| 6,248,938 | B1 | 6/2001 | Austin-Phillips et al. |
| 6,261,592 | B1 | 7/2001 | Nagashima et al. |
| 6,264,946 | B1 | 7/2001 | Mullertz et al. |
| 6,274,178 | B1 | 8/2001 | Beven et al. |
| 6,277,623 | B1 | 8/2001 | Oh et al. |
| 6,284,502 | B1 | 9/2001 | Maenz et al. |
| 6,291,221 | B1 | 9/2001 | Van Loon et al. |
| 6,309,870 | B1 | 10/2001 | Kondo et al. |
| 6,350,602 | B1 | 2/2002 | Van Gorcom et al. |
| 6,391,605 | B1 | 5/2002 | Kostrewa et al. |
| 6,451,572 | B1 | 9/2002 | Lei |
| 6,475,762 | B1 | 11/2002 | Stafford et al. |
| 6,511,699 | B1 | 1/2003 | Lei |
| 6,514,495 | B1 | 2/2003 | Svendsen et al. |
| 6,599,735 | B1 | 7/2003 | Bartok et al. |
| 6,720,174 | B1 | 4/2004 | Lehmann |
| 6,841,370 | B1 | 1/2005 | Lei |
| 6,974,690 | B2 | 12/2005 | Lei |
| 7,022,371 | B2 | 4/2006 | Stafford et al. |
| 7,026,150 | B2 | 4/2006 | Lei |
| 2001/0018197 | A1 | 8/2001 | Wong et al. |
| 2001/0029042 | A1 | 10/2001 | Fouache et al. |
| 2002/0068350 | A1 | 6/2002 | Kondo et al. |
| 2002/0102692 | A1 | 8/2002 | Lei |
| 2002/0127218 | A1 | 9/2002 | Svendsen et al. |
| 2002/0136754 | A1 | 9/2002 | Short et al. |
| 2003/0092155 | A1 | 5/2003 | Kostrewa et al. |
| 2003/0206913 | A1 | 11/2003 | Webel et al. |
| 2005/0095691 | A1 | 5/2005 | Lei |
| 2006/0153902 | A1 | 7/2006 | Lei |

FOREIGN PATENT DOCUMENTS

| | | | |
|---|---|---|---|
| EP | 0449376 | A2 | 10/1991 |
| EP | 0556883 | A1 | 8/1993 |
| EP | 0649600 | A1 | 4/1995 |
| EP | 0684313 | A2 | 11/1995 |
| EP | 0699762 | A2 | 3/1996 |
| EP | 0772978 | B1 | 5/1997 |
| EP | 0779037 | A1 | 6/1997 |
| EP | 0897010 | A2 | 2/1999 |
| EP | 0897985 | A2 | 2/1999 |
| EP | 0909821 | A2 | 4/1999 |
| EP | 0420358 | B1 | 5/1999 |
| EP | 0925723 | A1 | 6/1999 |
| EP | 0955362 | A1 | 11/1999 |
| EP | 0960934 | A1 | 12/1999 |
| GB | 2286396 | A | 8/1995 |
| GB | 2316082 | A | 2/1998 |
| JP | 10276789 | | 10/1998 |
| JP | 2001292789 | | 10/2001 |
| RU | 2113468 | | 6/1998 |
| WO | 86/01179 | | 2/1986 |
| WO | 90/03431 | A1 | 4/1990 |
| WO | 90/05182 | A1 | 5/1990 |
| WO | 91/05053 | | 4/1991 |
| WO | 91/14773 | A2 | 10/1991 |
| WO | 91/14782 | A1 | 10/1991 |
| WO | 93/14645 | A1 | 8/1993 |
| WO | 93/16175 | A1 | 8/1993 |
| WO | 93/19759 | A1 | 10/1993 |
| WO | 94/03072 | A1 | 2/1994 |
| WO | 94/03612 | A1 | 2/1994 |
| WO | 97/16076 | A1 | 5/1997 |
| WO | 97/35017 | A1 | 9/1997 |
| WO | 97/39638 | A1 | 10/1997 |
| WO | 97/45009 | A2 | 12/1997 |
| WO | 97/48812 | A3 | 12/1997 |
| WO | 98/05785 | A1 | 2/1998 |
| WO | 98/06856 | A1 | 2/1998 |
| WO | 98/20139 | A2 | 5/1998 |
| WO | 98/30681 | A1 | 7/1998 |
| WO | 98/44125 | A1 | 10/1998 |
| WO | 98/54980 | A2 | 12/1998 |
| WO | 99/08539 | A1 | 2/1999 |
| WO | 99/49022 | | 9/1999 |
| WO | 99/49740 | A1 | 10/1999 |
| WO | 00/10404 | A2 | 3/2000 |
| WO | 00/20569 | A1 | 4/2000 |
| WO | 00/41509 | A2 | 7/2000 |
| WO | 00/43503 | | 7/2000 |
| WO | 00/47060 | A1 | 8/2000 |
| WO | 00/58481 | A2 | 10/2000 |
| WO | 00/71728 | A1 | 11/2000 |
| WO | 00/72700 | A1 | 12/2000 |
| WO | 01/36607 | A1 | 5/2001 |
| WO | 01/58275 | A2 | 8/2001 |
| WO | 01/58276 | A2 | 8/2001 |

OTHER PUBLICATIONS

Greiner et al., "Purification and Characterization of Two Phytases from *Escherichia coli*," Arch, Biochem. Biophys. 303:107-113 (1993).

Han et al., "Development of Phytase Overexpressing Microbes for Nutritional Use," Poster Presentation at Cornell University's Biotechnology Symposium, Ithaca, New York (Oct. 15, 1997).

Jia et al., "Purification, Crystallization and Preliminary X-ray Analysis of the *Escherichia coli* Phytase," Acta Cryst. D54:647-649 (1998).

Kanai et al., "Recombinant Thermostable Cycloinulo-oligosaccharide Fructanotransferase Product by *Saccharomyces cerevisiae*," Appl. Environ. Microbiol. 63(12):4956-4960 (1997).

Kerovuo et al., "Isolation, Characterization, Molecular Gene Cloning, and Sequencing of a Novel Pytase from *Bacillus subtilis*," Appl. Environ. Microbiol. 64(6):2079-2085 (1998).

Kim et al., "Cloning of the Thermostable Phytase Gene (phy) from *Bacillus* sp. DS11 and its Overexpression in *Escherichia coli*," FEMS Microbiol. Lett. 162:185-191 (1998).

Konietzny et al., "Model Systems for Developing Detection Methods for Foods Deriving from Genetic Engineering," J. Food Comp. Anal. 10:28-35 (1997).

Kumagi et al., "Conversion of Starch to Ethanol in a Recombinant *Saccharomyces cerevisiae* Strain Expressing Rice alpha-amylase from a Novel *Pichia pastoris* Alcohol Oxidase Promoter," Biotechnol. 11:606-610 (1993).

Leeson et al, "Efficacy of New Bacterial Phytase in Poultry Diets," Can. J. Anim. Sci. 80:527-528 (2000).

Lei et al., "Biotechnological Developments of Effective Phytases for Mineral Nutrition and Environmental Protection," Appl. Microbiol. Biotech. 57(4):474-481 (2001).

Lim et al., "Crystal Structure of *Escherichia coli* Phytase and its Complex with Phytase," Nat. Struct. Biol. 7(2):108-113 (2000).

Lim et al., "Studies of Reaction Kinetics in Relation to the T of Polymers in Frozen Model Systems," in Levine, eds., Water Relationships in Food, New York, NY: Plenum Press, pp. 103-122 (1991).

Lozano et al, "Effect of Polyols on alpha-Chymotrypsin Thermostability: A Mechanistic Analysis of the Enzyme Stabilization," J. Biotechnol. 35:9-18 (1994).

Lozano et al., "Influence of Polyhydroxylic Cosolvents on Papain Thermostability," Enzyme Microb. Technol. 15:868-873 (1993).

Maugenest et al., "Cloning and Characterization of cDNA Encoding a Maize Seedling Phytase," Biochem. J. 322:511-517 (1997).

Meldgaard et al., "Different Effects of N-Glycosylation on the Thermostability of Highly Homologous Bacterial (1,3-1,4) Beta-Glucanases Secreted from Yeast," Microbiol. 140(1):159-166 (1994).

Minamiguchi et al., "Secretive Expression of the *Aspergillus aculeatus* Cellulase (FI-CM Case) by *Saccharomyces cerevisiae*," J. Ferment. Bioengin. 79(4):363-366 (1995).
Moore et al., "Molecular Cloning, Expression and Evaluation of Phosphohydrolases for Phytase-Degrading Activity," J. Industrial Microbiol. 14:396-402 (1995).
Murray et al., "Construction of Artificial Chromosomes in Yeast," Nature 305:189-193 (1983).
Murry et al., "The Effect of Microbial Phytase in a Pearl Millet-Soybean Meal Diet on Apparent Digestibility and Retention of Nutrients, Serum Mineral Concentration, and Bone Mineral Density of Nursery Pigs," J. Animal Sci. 75:1284-1291 (1997).
Novozymes A/S, Opposition Brief for European Patent No. EP 1-090-129 (19 pages) (Nov. 2006).
Phillippy et al., "Expression of an *Aspergillus niger* Phytase (phyA) in *Escherichia coli*," J. Agric. Food Chem. 45 (8):3337-3342 (1997).
Piddington et al., "The Cloning and Sequencing of the Genes Encoding Phytase (phy) and pH 2.5-Optimum Acid Phosphatase (aph) From *Aspergillus niger* var. awamori," Gene 133:55-62 (1993).
Rodriguez et al., "Cloning, Sequencing, and Expression of an *Escherichia coli* Acid Phosphatase/Phytase Gene (appA2) Isolated from Pig Colon," Biochem. Biophys. Res. Comm. 257:117-123 (1999).
Rossi et al., "Stabilization of the Restriction Enzyme EcoRI Dried with Trehalose and Other Selected Glass-Forming Solutes," Biotechnol. Prog. 13:609-616 (1997).
Schebor et al., "Glassy State and Thermal Inactivation of Invertase and Lactase in Dried Amorphous Matrices," Biotechnol. Prog. 13:857-863 (1997).
Scott et al., "The Effect of Phosphorous, Phytase Enzyme, and Calcium on the Performance of Layers Fed Corn-Based Diets," Poultry Sci. 78:1742,1749 (1999).
Sebastian et al., "Apparent Digestibility of Protein and Amino Acids in Brioler Chickens Fed a Corn-Soybean Diet Supplemented with Microbial Phytase," Poultry Sci. 76:1760-1769 (1997).
Sidhu et al., Analysis of alpha-Factor Secretion Signals by Fusing with Acid Phosphatase of Yeast, Gene 54:175-184 (1987).
Sun et al., "Expression of *Aspergillus niger* Phytase in Yeast *Saccharomyces cerevisiae* for Poultry Diet Supplementation," Poultry Sci. 76(Suppl. 1):5 (1997).
Takahashi et al., "Independent Production of Two Molecular Forms of a Recombinant *Rhizopus oryzae* Lipase by KEX2-Engineered Strains of *Saccharomyces cerevisiae*," Appl. Microbiol. Biotechnol. 52(4):534-540 (1999).
Terashima et al., "The Roles of the N-Linked Carbohydrate Chain of Rice alpha-amylase in Thermostability and Enzyme Kinetics," Eur. J. Biochem. 226:249-254 (1994).
Touati et al., "Pleiotropic Mutations in appR Reduce pH 2.5 Acid Phosphatase Expression and Restore Succinate Utilisation in CRP-Deficient Strains of *Escherichia coli*," Mol. Gen. Genet. 202:257-264 (1986).
Tschopp et al., "Heterologous Gene Expression in Methylotrophic Yeast," Biotechnol. 18:305-322 (1991).
Ullah, A.H.J., "*Aspergillus ficuum* Phytase: Partial Primary Structure, Substrate Selectivity, and Kinetic Characterization," Prep. Biochem. 18(4):459-471 (1988).
Verwoerd et al., "Stable Accumulation of *Aspergillus niger* Phytase in Transgenic Tobacco Leaves," Plant Physiol. 109:1199-1205 (1995).
Yao et al., "Recombinant *Pichia pastoris* Overexpressing Bioactive Phytase," Science in China Series C. Life Sciences 41(3):330-336 (1998).
Zvonok et al., "Construction of Versatile *Escherichia coli*-Yeast Shuttle Vectors for Promoter Testing in *Saccharomyces cerevisiae*," Gene 66(2):313-318 (1988).
Ullah et al., "Differences in the Active Site Environment of *Aspergillus ficuum* Phytases," Biochem. Biophys. Res. Comm. 243:458-462 (1998).
GenBank Accession No. AAB96872 (Jan. 16, 1998).
GenBank Accession No. M94550 (Apr. 27, 1993).
GenBank Accession No. P34752 (Jan. 25, 2005).
Han et al., "Expression of an *Aspergillus niger* Phytase Gene (phyA) in *Saccharomyces cerevisiae*," Appl. Environ. Microbiol. 65(5):1915-1918 (1999).
Kostrewa et al., "Crystal Structure of *Aspergillus niger* pH 2.5 Acid Phosphatase at 2.4 A Resolution," J. Mol. Biol. 288:965-974 (1997).
Kostrewa et al., "Crystal Structure of Phytase from *Aspergillus ficuum* at 2.5 A Resolution," Nat. Struct. Biol. 4:185-190 (1997).
Lehmann et al., "Exchanging the Active Site Between Phytases for Altering the Functional Properties of the Enzyme," Protein Sci. 9(10):1866-1872 (2000).
Lehmann et al., "From DNA Sequence to Improved Functionality: Using Protein Sequence Comparisons to Rapidly Design a Thermostable Consensus Phytase," Protein Eng. 13(1):49-57 (2000).
Lei et al., "Calcium Level Affects the Efficacy of Supplemental Microbial Phytase in Corn-Soybean Meal Diets of Weanling Pigs," J. Anim. Sci. 72(1):139-143 (1994).
Lei et al., "Nutritional Benefits of Phytase and Dietary Determinants of its Efficacy," J. Appl. Anim. Res. 17:97-112 (2000).
Lei et al., "Supplemental Microbial Phytase Improves Bioavailability of Dietary Zinc to Weanling Pigs," J. Nutr. 123:1117-1123 (1993).
Lei et al., "Supplementing Corn-Soybean Meal Diets with Microbial Phytase Linearly Improves Phytase Phosphorus Utilization by Weanling Pigs," J. Anim. Sci. 71:3359-3367 (1993).
Mitchell et al., "The Phytase Subfamily of Histidine Acid Phosphatases: Isolation of Genes for Two Novel Phytases from the Fungi *Aspergillus terreus* and *Myceliophthora thermophila*," Microbiology 143:245-252 (1997).
Mullaney et al., "Advances in Phytase Research," Advances in Applied Microbiology 47:157-199 (2000).
Mullaney et al., "Phytase Activity in *Aspergillus fumigatus* Isolates," Biochem. Biphys. Res. Commun. 275:759-763 (2000).
Mullaney et al., "Positive Identification of a Lambda gt11 Clone Containing a Region of Fungal Phytase Gene by Immunoprobe and Sequence Verification," Appl. Microbiol. Biotechnol. 35:611-614 (1991).
Mullaney et al., "Site-Directed Mutagenesis of *Aspergillus niger* NRRL 3135 Phytase at Residue 300 to Enhance Catalysis at pH 4.0," Biochem. Biophys. Res. Commun. 297(4):1016-1020 (2002).
Nielsen et al., "The Determinants of alpha-Amylase pH-Activity Profiles," Protein Eng. 14(7):505-512 (2001).
Ostanin et al., "Asp304 of *Escherichia coli* Acid Phosphatase is Involved in Leaving Group Protonation," J. Biol. Chem. 268(28):20778-20784 (1993).
Ostanin et al., "Overexpression, Site-Directed Mutagenesis and Mechanism of *Escherichia coli* Acid Phosphatase," J. Biol. Chem. 267(32):22830-22836 (1992).
Pasamontes et al., "Gene Cloning, Purification, and Characterization of a Heat-Stable Phytase from the Fungus *Aspergillus fumigatus*," Appl. Environ. Microbiol. 63(5):1696-1700 (1997).
Rodriguez et al., "expression of the *Aspergillus fumigatus* Phytase Gene in *Pichia pastoris* and Characterization of the Recombinant Enzyme," Biochem. Biophys. Res. Commun. 268:373-378 (2000).
Rodriguez et al., "Site-Directed Mutagenesis Improves Catalytic Efficiency and Thermostability of *Escherichia coli* pH 2.5 Acid Phosphatase/Phytase Expressed in *Pichia pastoris*," Arch. Biochem. Biophys. 382:105-112 (2000).
Tomschy et al., "Active Site Residue 297 of *Aspergillus niger* Phytase Critically Affects the Catalytic Properties," FEBS Lett 472(2-3):169-172 (2000).
Tomschy et al., "Engineering of Phytase for Improved Activity at Low pH," Appl. Environ. Microbiol. 68(4):1907-1913 (2002).
Tomschy et al., "Optimization of the Catalytic Properties of *Aspergillus fumigatus* Phytase Based on the Three-Dimensional Dimensional Structure," Protein Sci. 9(7):1304-1311 (2000).
Ullah et al., "Cyclohexanedione Modification of Arginine at the Active Site of *Aspergillus ficuum* Phytase," Biochem. Biophys. Res. Commun. 178(1):45-53 (1991).
Ullah et al., "Extracellular Phytase (E.C. 3.1.3.8) from *Aspergillus ficuum* NRRL 3135:Purification and Characterization," Prep. Biochem. 17(1):63-91 (1987).

van Dijck, P.W.M., "Chymosin and Phytase Made by Genetic Engineering (No. 10 in a Series of Articles to Promote a Better Understanding of the Use of Genetic Engineering)," J. Biotechnology 67:77-80 (1999).

van Etten et al., "Covalent Structure, Disulfide Bonding, and Identification of Reactive Surface and Active Site Residues of Human Prostatic Acid Phosphatase," J. Biol. Chem. 266(4):2313-2319 (1991).

van Hartingsveldt et al., "Cloning, Characterization and Overexpression of the Phytase-Encoding Gene (phyA) of *Aspergillus niger*," Gene 127:87-94 (1993).

Wodzinski et al, "Phytase," Adv. Appl. Microbiol. 42:263-302 (1996).

Wyss et al., "Biochemical Characterization of Fungal Phytases (myo-Insositol Hexakisphosphate Phosphohydrolases): Catalytic Properties," Appl. Environ. Microbiol. 65(2):367-373 (1999).

Wyss et al., "Biophysical Characterization of Fungal Phytases (myo-Inositol Hexakisphosphate Phosphohydrolases): Molecular Size, Glycosylation Pattern, and Engineering of Proteolytic Resistance," Appl. Environ. Microbiol. 65 (2):359-366 (1999).

Yi et al., "Sites of Phytase Activity in the Gastrointestinal Tract of Young Pigs," Animal Feed Science Technology 61:361-368 (1996).

Atlung et al., "Role of the Transcriptional Activator AppY in Regulation of the cyx appA Operon of *Escherichia coli* by Anaerobiosis, Phosphate Starvation, and Growth Phase," J. Bacteriol. 176(17):5414-5422 (1994).

ATCC Catalog for Yeasts, 19th Edition (1995).

Belin et al., "A Pleiotropic Acid Phosphatase-Deficient Mutant of *Escherichia coli* Shows Premature Termination in the dsbA Gene. Use of dsbA::phoA Fusions to Localize a Structurally Important Domain in DsbA," Mol. Gen. Genet. 242:23-32 (1994).

Blondeau et al., "Development of High-Cell-Density Fermentation for Heterologous Interleukin 1Beta Production in *Kluyveromyces lactis* Controlled by the PHO5 Promoter," Appl. Microbiol. Biotechnol. 41:324-329 (1994).

Boctor et al., "Enhancement of the Stability of Thrombin by Polyols: Microcalorimetric Studies," J. Pharm. Pharmacol. 44:600-603 (1992).

Boer et al., "Characterization of *Trichoderma reesei* Cellobiohydrolase Cel7a Secreted from *Pichia pastoris* Using Two Different Promoters," Biotechnol. Bioengin. 69(5):486-494 (2000).

Brondsted et al., "Effect of Growth Conditions on Expression of the Acid Phosphatase (cyx-appA) Operon and the appY Gene, Which Encodes a Transcriptional Activator of *Escherichia coli*," J. Bacteriol. 178(6):1556-1564 (1996).

Chiarugi et al., "Differential Role of Four Cysteines on the Activity of a Low M, Phosphotyrosine Protein Phosphatase," FEBS Lett. 310(1):9-12 (1992).

Dassa et al., "Identification of the Gene appA for the Acid Phosphatase (pH Optimum 2.5) of *Escherichia coli*," Mol. Gen. Genet. 200:68-73 (1985).

Dassa et al., "The Complete Nucleotide Sequence of the *Escherichia coli* Gene appA Reveals Significant Homology Between pH 2.5 Acid Phosphatase and Glucose-1-Phosphatase," J. Bacteriol. 172(9):5497-5500 (1990).

Database Accession No. B36733, corresponding to Greiner et al., Arch. Biochem. Biophys. 303:107-113 (1993).

Divakaran et al., "In vitro Studies on the Interaction of Phytase with Trypsin and Amylase Extracted from Shrimp (*Penaeus vannamei*) Hepatopancreas," J. Agric. Food Chem. 46:4973-4976 (1998).

DSM Nutritional Products, Opposition Brief for European Patent No. EP 1-090-129 (10 pages) Nov. 15, 2006.

Golovan et al., "Characterization and Overproduction of the *E. coli* appA Encoded Biofunctional Enzyme that Exhibits Both Phytase and Acid Phosphatase Activities," Can. J. Microbiol. 46:59-71 (2000).

Granovskii et al., "Expression of Hepatitis B Virus HBsAg Gene in Yeast Cells Under Control of Promoter Region of PH05 Gene," Soviet Progress in Virology 5:45-47 (1985).

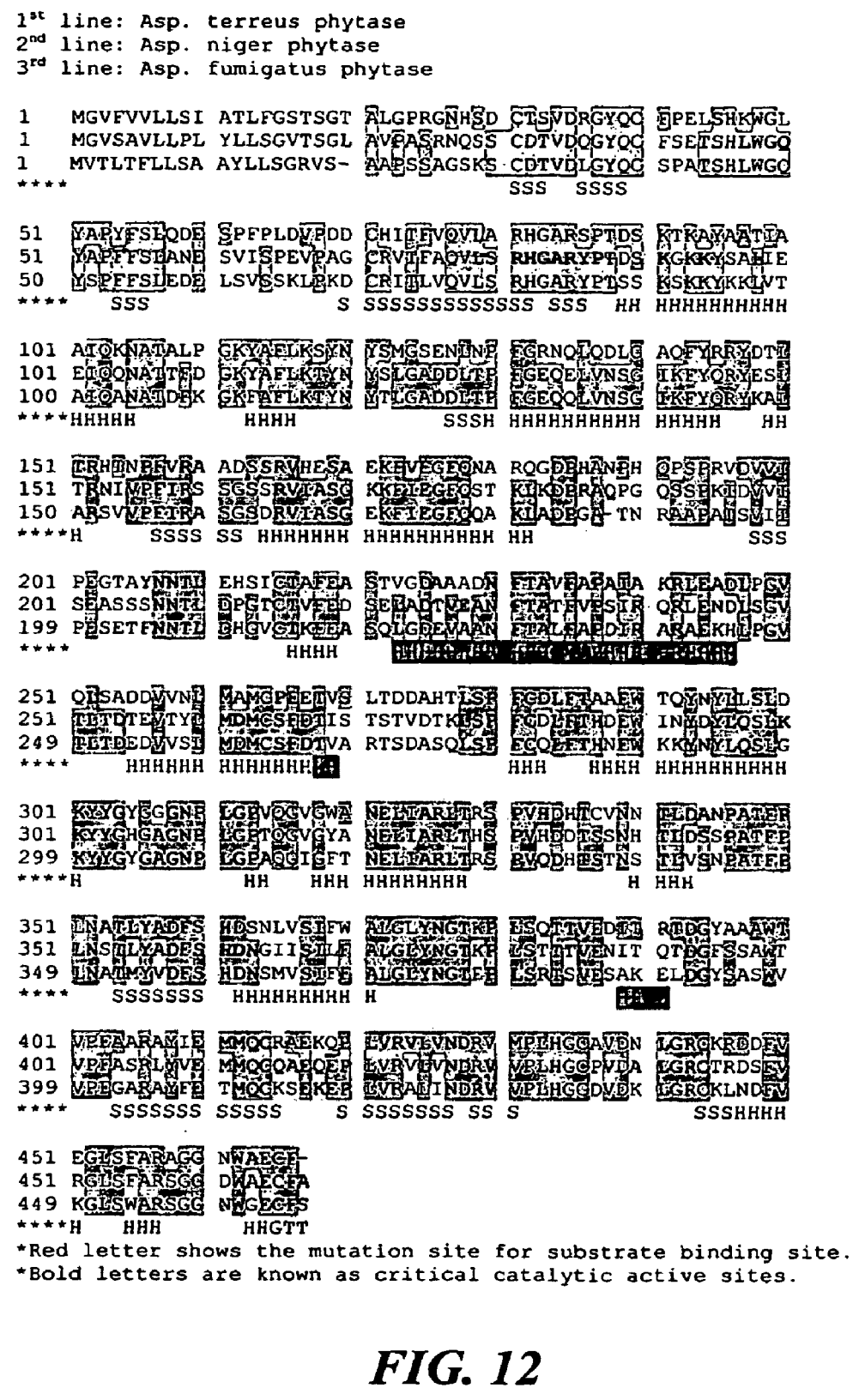

```
1st line: Asp. terreus phytase
2nd line: Asp. niger phytase
3rd line: Asp. fumigatus phytase

1    MGVFVVLLSI ATLFGSTSGT ALGPRGNHSD CTSVDRGYQC SPELSHKWGL
1    MGVSAVLLPL YLLSGVTSGL AVPASRNQSS CDTVDQGYQC FSETSHLWGQ
1    MVTLTFLLSA AYLLSGRVS- AAPSSAGSKS CDTVDLGYQC SPATSHLWGQ
****                                          SSS   SSSS

51   YAPYFSLQDE SPFPLDVPDD CHITFVQVLA RHGARSPTDS KTKAYAATIA
51   YAPFFSLANE SVISPEVPAG CRVTFAQVLS RHGARYPTDS KGKKYSALIE
50   YSPFFSLEDE LSVSSKLPKD CRITLVQVLS RHGARYPTSS KSKKYKKLVT
****   SSS            S SSSSSSSSSSSS SSS   HH HHHHHHHHHH

101  AIQKNATALP GKYAFLKSYN YSMGSENLNP FGRNQLQDLG AQFYRRYDTL
101  EIQQNATTFD GKYAFLKTYN YSLGADDLTP FGEQELVNSG IKFYQRYESL
100  AIQANATDFK GKFAFLKTYN YTLGADDLTP FGEQQLVNSG IKFYQRYKAL
****HHHHH     HHHH           SSSH HHHHHHHHHH HHHHH    HH

151  TRHINPFVRA ADSSRVHESA EKFVEGFQNA RQGDPHANPH QPSPRVDVVI
151  TRNIVPFIRS SGSSRVIASG KKFIEGFQST KLKDPRAQPG QSSPKIDVVI
150  ARSVVPFIRA SGSDRVIASG EKFIEGFQQA KLADPGA-TN RAAPAISVII
****H      SSSS SS HHHHHHH HHHHHHHHHH HH                SSS

201  PEGTAYNNTL EHSICTAFEA STVGDAAADN FTAVFAPAIA KRLEADLPGV
201  SEASSSNNTL DPGTCTVFED SELADTVEAN FTATFVPSIR QRLENDLSGV
199  PESETFNNTL DHGVCTKFEA SQLGDEVAAN FTALFAPDIR ARAEKHLPGV
****                HHHH   [illegible]

251  QLSADDVVNL MAMCPFETVS LTDDAHTLSP FCDLFTAAEW TQYNYLLSLD
251  TLTDTEVTYL MDMCSFDTIS TSTVDTKLSP FCDLFTHDEW INYDYLQSLK
249  TLTDEDVVSL MDMCSFDTVA RTSDASQLSP FCQLFTHNEW KKYNYLQSLG
****      HHHHHH HHHHHHH[illegible]            HHH    HHHH HHHHHHHHHH

301  KYYGYGGGNP LGPVQGVGWA NELIARLTRS PVHDHTCVNN TLDANPATFP
301  KYYGHGAGNP LGPTQGVGYA NELIARLTHS PVHDDTSSNH TLDSSPATFP
299  KYYGYGAGNP LGPAQGIGFT NELIARLTRS PVQDHTSTNS TLVSNPATFP
****H          HH   HHH HHHHHHHH              H HHH

351  LNATLYADFS HDSNLVSIFW ALGLYNGTKP LSQTTVEDIT RTDGYAAAWT
351  LNSTLYADFS HDNGIISILF ALGLYNGTKP LSTTTVENIT QTDGFSSAWT
349  LNATMYVDFS HDNSMVSIFF ALGLYNGTEP LSRTSVESAK ELDGYSASWV
****     SSSSSSS  HHHHHHHHH H                [illegible]

401  VPFAARAYIE MMQCRAEKQP LVRVLVNDRV MPLHGCAVDN LGRCKRDDFV
401  VPFASRLYVE MMQCQAEQEP LVRVLVNDRV VPLHGCPVDA LGRCTRDSFV
399  VPFGARAYFE TMQCKSEKEP LVRALINDRV VPLHGCDVDK LGRCKLNDFV
****     SSSSSSS SSSSS     S SSSSSSS SS S            SSSHHHH

451  EGLSFARAGG NWAECF-
451  RGLSFARSGG DWAECFA
449  KGLSWARSGG NWGECFS
****H    HHH        HHGTT
```

*Red letter shows the mutation site for substrate binding site.
*Bold letters are known as critical catalytic active sites.

*FIG. 12*

Plasma Alkaline Phosphatase (AKP) Activity of Pigs Fed Low-P Diets

Average Daily Gain (ADG) of Pigs Fed Low-P Diets

USING MUTATIONS TO IMPROVE *ASPERGILLUS* PHYTASES

The subject matter of this application was made with support from the United States Government under USDA Project No. 6435-13410-002-00D. The U.S. Government may have certain rights.

This application is a Continuation of U.S. application Ser. No. 10/662,914, filed Sep. 15, 2003, which is issuing as U.S. Pat. No. 7,309,505. This application claims the benefit of U.S. Provisional Patent Application Ser. No. 60/410,736, filed Sep. 13, 2002, which is hereby incorporated by reference in its entirety.

FIELD OF THE INVENTION

The present invention relates to using mutations to improve phytases of *Aspergillus*.

BACKGROUND OF THE INVENTION

Phytase enzymes are a group of histidine acid phosphatases with great potential for improving mineral nutrition and protecting the environment from phosphorus pollution coming from animal waste (Lei et al., *J. Appl. Anim. Res.* 17:97-112 (2000)). *Aspergillus niger* NRRL 3135 phyA phytase has been cloned (Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991); and Van Hartingsveldt et al., "Cloning, Characterization and Overexpression of the Phytase-Encoding Gene (phyA) of *Aspergillus niger," Gene* 127:87-94 (1993)) and overexpressed for commercial use as animal feed additive (Van Dijck, *J. Biotechnology* 67:77-80 (1999)). Recent information on its molecular structure from its X-ray-deduced three dimensional structure (Kostrewa et al., "Crystal Structure of Phytase from *Aspergillus ficuum* at 2.5 Å Resolution," *Nat. Struct. Biol.* 4:185-190 (1997)) has facilitated several studies to enhance the specific activity of other phytases. In one of these studies, a recombinant *A. fumigatus* ATCC 13070 phytase had its specific activity with phytic acid as substrate significantly enhanced by the replacement of glutamine (Q) at position 27 for leucine (L). It was suggested that amino acid ("AA") residue 27 was part of the active site in *A. fumigatus* phytase (Tomschy et al., "Optimization of the Catalytic Properties of *Aspergillus fumigatus* Phytase Based on the Three-Dimensional Structure," *Protein Science* 9:1304-1311 (2000)). The presence of leucine at this AA residue in *A. terreus* phytase (Mitchell et al., "The Phytase Subfamily of Histidine Acid Phosphatases: Isolation of Genes for Two Novel Phytases From the Fungi *Aspergillus terreus* and *Myceliophthora thermophila," Microbiology* 143:245-252 (1997)) also supports this replacement of glutamine with leucine, since *A. terreus* phytase displays even higher activity than *A. niger* NRRL 3135 phytase (Wyss et al., "Biochemical Characterization of Fungal Phytases (myo-inositol hexakisphosphate phosphohydrolases): Catalytic Properties," *Appl. Environ. Microbiol.* 65:367-373 (1999)). The replacement of Q with L was theorized as resulting in the elimination of a hydrogen bond between the side chain of Q and the 6-phosphate group of myo-inositol hexakisphosphate. This bond was postulated to be a reason for the lower specific activity of *A. fumigatus* ATTC 13070 phytase. Substitution of proline at residue 27 resulted in lower activity than the wild type enzyme. However, it was noted in that study that the proline substitution mutant phytase displayed a tendency to aggregate and precipitate and this could have lowered its true activity level. *A. niger* NRRL 3135 phytase like *A. fumigatus* phytase has Q at AA residue 27, and it remains to be determined how specific activity responds to substitutions of Q27L and Q27P.

Phytase from *Aspergillus fumigatus* has been studied for its good thermotolerance properties, significant levels of activity over a wide range of pH, and resistance to hydrolysis by pepsin (Pasamontes et al., "Gene Cloning, Purification, and Characterization of a Heat-Stable Phytase From the Fungus *Aspergillus fumigatus," Appl. Environ. Microbiol.* 63:1696-1700 (1997); and Rodriguez et al., "Expression of the *Aspergillus fumigatus* Phytase Gene in *Pichia pastoris* and Characterization of the Recombinant Enzyme," *Biochem. Biophys. Res. Commun.* 268:373-378 (2000)). However, specific activity of this phytase is not as high as some other fungal phytases such as those produced by *A. terreus* or *A. niger.*

During the last decade, the increased use of plant proteins such as soybean meal, etc., in animal feed (Berlan et al., "The Growth of the American 'Soybean Complex'," *Eur. R. Agr. Eco.* 4:395-416 (1977)) has created an expanding market for phytase as an animal feed additive. Adding phytase allows monogastric animals, i.e., poultry and swine, to utilize the phytin phosphorus in this plant meal (Mullaney et al., "Advances in Phytase Research," *Advances in Applied Microbiology* 47:157-199 (2000)). Without phytase, the phytin bound phosphorus is unavailable to these animals and is excreted in their manure where it can potentially harm the environment by further elevating the soil phosphorus levels (Wodzinski et al., "Phytase," *Advances in Applied Microbiology* 42:263-302 (1996)). During this period, the phytaseA gene (phyA) from *Aspergillus niger* (ficuum) NRRL 3135 was cloned, overexpressed, and its product marketed as (Natuphos®) in the animal feed industry as an effective means to lower phosphate levels in manure from poultry and swine (van Hartingsveldt et al., "Cloning, Characterization and Overexpression of the Phytase-Encoding Gene (phyA) of *Aspergillus niger," Gene* 127:87-94 (1993)).

The native NRRL 3135 phyA phytase is a stable enzyme (Ullah et al., "Extracellular Phytase (E. C. 3.1.3.8) from *Aspergillus ficuum* NRRL 3135: Purification and Characterization," *Prep. Boichem.* 17:63-91 (1987)) that has a high specific activity for phytic acid (Wyss et al., "Biochemical Characterization of Fungal Phytases (Myo-inositol Hexakisphosphate Phosphohydrolases): Catalytic Properties," *Applied and Envir. Micro.* 65:367-373 (1999)). This has contributed to its acceptance by the animal feed industry (Wodzinski et al., "Phytase," *Advances in Applied Microbiology* 42:263-302 (1996)). It has also been widely researched and utilized to engineer improved features into other fungal phytases by recombinant DNA techniques (Wyss et al., "Biophysical Characterization of Fungal Phytases (Myo-iositol Hexakisphosphate Phosphohydrolases): Molecular Size, Glycosylation Pattern, and Engineering of Proteolytic Resistance," *Applied and Envir. Micro.* 65:359-366 (1999); and Lehmann et al., "Exchanging the Active Site Between Phytases for Altering the Functional Properties of the Enzyme," *Protein Science* 9:1866-1872 (2000)). However, to date no studies have successfully employed any of this information to improve this widely used benchmark phytase.

NRRL 3135 PhyA is known to have an active site motif characteristic of the histidine acid phosphatase (HAP) class of enzymes (Ullah et al., "Cyclohexanedione Modification of Arginine at the Active Site of *Aspergillus ficuum* Phytase," *Biochem. Biophys. Res. Commun.* 178:45-53 (1991); and Van Etten et al., "Covalent Structure, Disulfide Bonding, and Identification of Reactive Surface and Active Site Residues of Human Prostatic Acid Phosphatase," *J. Biol. Chem.* 266: 2313-2319 (1991)). Previous studies of the crystal structure of the *A. niger* NRRL 3135 phyA (Kostrewa et al., "Crystal Structure of Phytase from *Aspergillus ficuum* at 2.5 Å Resolution," *Nat. Struct. Biol.* 4:185-190 (1997)) and phyB (Kostrewa et al., "Crystal Structure of *Aspergillus niger* pH 2.5 Acid Phosphatase at 2.4 Å Resolution," *J. Mol. Biol.* 288:965-974 (1999)) molecules have provided researchers with structural models of both these enzymes. These models have facilitated the identification of the residues constituting the catalytic active center of the molecules, i.e., both the active site and substrate specificity site. Its active site consists of a catalytic center (R81, H82, R66, R156, H361 D362) and a substrate specificity site (K91, K94, E228, D262, K300, K301) (Kostrewa et al., "Crystal Structure of *Aspergillus niger* pH 2.5 Acid Phosphatase at 2.4 Å Resolution," *J. Mol. Biol.* 288:965-974 (1999)). The amino acid numbers refer to full length phytase encoded by the *A. niger* NRRL 3135 phyA gene (NCBI Accession No. P34752). Amino acid reference numbers in Kostrewa et al., "Crystal Structure of *Aspergillus niger* pH 2.5 Acid Phosphatase at 2.4 Å Resolution," *J. Mol. Biol.* 288:965-974 (1999) were derived from a slightly truncated sequence. The narrow substrate specificity and the unique pH activity profile of this phytase, a drop in activity in the pH range 3.0-5.0, have been ascribed to the interaction of these acidic and basic amino acids comprising the substrate specificity site. This low activity at this intermediate pH range is not observed in other fungal phytases and is an undesirable feature of *A. niger* NRRL 3135 phyA.

This information has enabled the catalytic properties of other phyAs to be altered by site-directed mutations of specific amino acids (Tomschy et al., "Optimization of the Catalytic Properties of *Aspergillus fumigatus* Phytase Based on the Three-Dimensional Structure," *Protein Science* 9:1304-1311 (2000); Tomschy et al., "Active Site Residue 297 of *Aspergillus niger* Phytase Critically *Affects the Catalytic Properties," FEBS* 472:169-172 (2000); and Lehmann et al., "Exchanging the Active Site Between Phytases for Altering the Functional Properties of the Enzyme," *Protein Science* 9:1866-1872 (2000)). In the case of *A. fumigatus*, the three-dimensional structure of the native NRRL 3135 phytase molecule was utilized to identify nonconserved amino acids that were associated with increased catalytic activity (Tomschy et al., "Optimization of the Catalytic Properties of *Aspergillus fumigatus* Phytase Based on the Three-Dimensional Structure," *Protein Science* 9:1304-1311 (2000)). In that study, the change of a single amino acid residue, Q27, had a significant effect on specific activity, pH activity profile, and substrate specificity. The critical role of a single amino acid residue, R297, was also demonstrated in *A. niger* T213 phyA (Tomschy et al., "Active Site Residue 297 of *Aspergillus niger* Phytase Critically Affects the Catalytic Properties," *FEBS* 472:169-172 (2000)). *A. niger* T213 phyA differs from *A. niger* NRRL 3135 phyA in only 12 amino acid residues, but has a significantly lower specific activity for phytic acid than NRRL 3135 phytase. An analysis of the available 3D structure information identified only three divergent residues with an association with the substrate binding site. Independent site-directed mutation replacements of these three amino acids established that only R297 was responsible for strain T213's lower specific activity. Replacement of this residue with glutamine (Q), the residue at this position in *A. niger* NRRL 3135 phyA, resulted in a two optima pH profile and a specific activity level nearly identical with *A. niger* NRRL 3135 phyA. The shorter side chain of the neutral Q, which results in lower binding of substrates and products, was cited as the presumed reason for the increased specific activity in the recombinant phytase. Lehmann et al. modified the catalytic properties of a synthetic phytase, consensus phytase-1, by replacing 23 amino acids in the synthetic phytase with the corresponding amino acid in *A. niger* NRRL 3135 phyA (Lehmann et al., "Exchanging the Active Site Between Phytases for Altering the Functional Properties of the Enzyme," *Protein Science* 9:1866-1872 (2000)). This new consensus phytase, consensus phytase-7, and *A. niger* NRRL 3135 phyA then had almost identical amino acids within or immediately adjacent to their active site. Consensus phytase-7 catalytic characteristics were reported to have shifted to the more favorable properties of *A. niger* NRRL 3135 phyA.

Phytate (myo-inositol hexakisphosphate) is the major form of phosphorus in plant origin feed. Non-ruminants such as poultry and swine are unable to utilize phytate phosphorus in soy-corn based diet. Supplemental microbial phytase has been used successfully to improve phytate phosphorus utilization and to reduce phosphorus excretion by these animals (Lei et al., "Supplementing Corn-Soybean Meal Diets with Microbial Phytase Linearly Improves Phytate Phosphorus Utilization by Weanling Pigs," *J. Anim. Sci.* 71:3359-3367 (1993); and Lei et al., "Supplemental Microbial Phytase Improves Bioavailability of Dietary Zinc to Weanling Pigs," *J. Nutr.* 123:1117-23 (1993)). The most widely used commercial phytase is *Aspergillus niger* PhyA. However, this enzyme has a unique pH profile: two pH optima, 5 to 5.5 and 2.5, a drop in activity in the range of pH 3 to 5, and a dip at pH 3.5. Because phytate degradation by dietary phytase takes place mainly in the stomach (Yi et al., "Sites of Phytase Activity in the Gastrointestinal Tract of Young Pigs," *Animal Feed Science Technology* 61:361-368 (1996)), in which pH ranges from 2.5 to 3.5, the activity dip of PhyA at pH 3.5 really limits its efficacy in animal feeding.

PhyA belongs to the histidine acid phosphatase (HAP) enzyme family and has the characteristic active site motifs: RHG and HD. In general, histidine in the RHG motif is proposed to perform the nucleophilic attack, and aspartic acid in the HD motif is proposed to protonate the leaving alcohol (Ostanin et al., "Overexpression, Site-Directed Mutagenesis, and Mechanism of *Escherichia coli* Acid Phosphatase," *J. Biol. Chem.* 267:22830-22836 (1992); Ostanin et al., "Asp (304) of *Escherichia coli* Acid Phosphatase is Involved in Leaving Group Protonation," *J. Biol. Chem.* 268(28):20778-20784 (1993); and Kostrewa et al., "Crystal Structure of Phytase from *Aspergillus ficuum* at 2.5 Å Resolution," *Nat. Struct. Biol.* 4:185-90 (1997)). The clustering of basic amino acids at the active site of PhyA creates a favorable electrostatic environment for binding the highly negatively charged substrate phytate. Two arginine residues (81 and 85) in the RHG motif are known to bind with the scissible phosphate group of the phytate, while other amino acid residues in the α-domain are involved in the substrate binding (P87, T88, K91, K94, E228, D262, K300, K301) (Kostrewa et al., "Crystal Structure of *Aspergillus niger* pH 2.5 Acid Phosphatase at 2.4 Å Resolution," *J. Mol. Biol.* 288:965-974 (1999)).

The $pK_a$ values of the acid/base catalysts in the catalytic active sites normally determine the pH profiles of enzyme activity (Nielsen et al., "The Determinants of—Amylase pH-Activity Profiles," *Protein Eng.* 14:505-512 (2001)). Since the $pK_a$ value of a residue depends on the free energy difference between the neutral and the charged states of the residue in the protein, an enzyme pH profile may be altered by changing the charges of amino acid residues near the acid/base catalytic residues. A negatively charged amino acid generally raises the $pK_a$ value of the titratable residue and a positively charged amino acid reduces the $pK_a$ value. Phytase protein sequence comparisons indicate that the enzyme with acidic optimal pH has more positively charged amino acids in the substrate binding site, which gives a more favorable environment for substrate binding at low pH by providing more ionized groups in the binding site. In addition, the pH profile of phytase is affected by substrate or buffer.

SUMMARY OF THE INVENTION

The present invention relates to an isolated nucleic acid molecule encoding a mutant phytase. In one embodiment, the isolated nucleic acid molecule of the present invention can encode a mutant phytase that has an amino acid sequence having at least 96 percent sequence identity to SEQ ID NO:2 over a region of at least 100 amino acid residues. In this embodiment, the amino acid sequence of the mutant phytase can contain at least one substitution of at least one amino acid residue corresponding to residue 50, 91, 94, 228, 262, 300, and/or 301 of SEQ ID NO:2. In another embodiment, the isolated nucleic acid molecule of the present invention can encode a mutant phytase that has an amino acid sequence having at least 96 percent sequence identity to SEQ ID NO:4 over a region of at least 100 amino acid residues. In this embodiment, the amino acid sequence of the mutant phytase can contain a substitution corresponding to amino acid residue 363 of SEQ ID NO:4. The present invention further relates to recombinant DNA expression systems and host cells containing the isolated nucleic acid molecule of the present invention.

The present invention also relates to a method of recombinantly producing a mutant phytase. This method involves transforming a host cell with at least one heterologous nucleic acid molecule according to the present invention under conditions suitable for expression of the mutant phytase. The mutant phytase is then isolated.

The present invention further relates to an isolated mutant phytase having an amino acid sequence that has at least 96 percent sequence identity to SEQ ID NO:2 over a region of at least 100 amino acid residues. This mutant phytase can contain at least one substitution of at least one amino acid residue corresponding to residue 50, 91, 94, 228, 262, 300, and/or 301 of SEQ ID NO:2. The present invention also relates to an isolated mutant phytase having an amino acid sequence that has at least 96 percent identity to SEQ ID NO:4 over a region of at least 100 amino acid residues. This mutant phytase can contain a substitution of an amino acid residue corresponding to residue 363 of SEQ ID NO:4. The present invention also relates to an animal feed composition containing the isolated mutant phytase of the present invention, as well as a foodstuff containing the animal feed composition.

The present invention further relates to a method of feeding a monogastric animal. This method involves feeding to the animal a foodstuff in combination with the isolated mutant phytase of the present invention.

The present invention further relates to a method of improving the nutritional value of a foodstuff consumed by an animal. This method involves providing a foodstuff including myo-inositol hexakisphosphate. A mutant phytase of the present invention is also provided. The foodstuff, in combination with the mutant phytase, is fed to the animal under conditions effective to increase the bioavailability of phosphate from phytate.

The present invention also relates to a method for altering the enzymatic properties of a wild-type phytase of an *Aspergillus* species. This method involves providing a wild-type phytase of an *Aspergillus* species. Examples of suitable wild-type *Aspergillus* species include, without limitation, *Aspergillus niger* and *Aspergillus fumigatus*. In one embodiment, the wild-type phytase is an *Aspergillus niger* phytase having an amino acid sequence that has at least 96 percent sequence identity to SEQ ID NO:2 over a region of at least 100 amino acid residues. In another embodiment, the wild-type phytase is an *Aspergillus fumigatus* phytase having an amino acid sequence that has at least 96 percent sequence identity to SEQ ID NO:4 over a region of at least 100 amino acid residues. The method also involves altering the amino acid sequence of the wild-type phytase under conditions effective to yield a mutant phytase having a modified substrate binding region and/or improved catalytic efficiency compared to the amino acid sequence of the wild-type phytase. In one embodiment, altering the amino acid sequence involves introducing into the amino acid sequence of an *Aspergillus niger* wild-type phytase at least one substitution of at least one amino acid residue corresponding to residue 50, 91, 94, 228, 262, 300, and/or 301 of SEQ ID NO:2. In another embodiment, altering the amino acid sequence involves introducing into the amino acid sequence of the *Aspergillus fumigatus* wild-type phytase a substitution at an amino acid residue corresponding to residue 363 of SEQ ID NO:4.

The present invention also relates to a method of in vitro hydrolysis of phytate. This method involves providing a mutant phytase of the present invention. The mutant phytase is combined with a phytate source under conditions effective to increase the bioavailability of phosphate from the phytate source.

The present invention also relates to a method of improving the nutritional value of a foodstuff consumed by humans. This method involves providing a mutant phytase according to the present invention. The mutant phytase is combined with a foodstuff consumed by humans under conditions effective to increase the bioavailability of minerals from the foodstuff. Suitable minerals can include, without limitation, iron, zinc, phosphorus, and calcium.

The present invention further relates to a method of imparting improved mineral nutritional value to a plant that is edible for consumption by animals. This method involves providing a transgene containing an isolated nucleic acid molecule of the present invention. The isolated nucleic acid molecule is operatively associated with a regulatory sequence containing transcriptional and translational regulatory elements that control expression of the isolated nucleic acid molecule in a transgenic plant cell. The method also involves providing a non-transformed plant that is edible for consumption by animals. The transgene is inserted into the genome of the non-transformed plant under conditions effective to yield a transformed plant that transgenically expresses a mutant phytase encoded by the isolated nucleic acid molecule of the present invention. The resulting transformed plant has improved mineral nutritional value compared to that of the non-transformed plant.

The mutant phytases of the present invention exhibit a number of improved attributes compared to their non-mutant counterpart phytases. For example, the mutant phytases of the present invention exhibit improved phytase activity over their non-mutant counterpart phytases. The mutant phytases of the present invention also exhibit altered pH profiles and altered pH optima that favor their use in acidic environments such as the gastrointestinal tracts of animals. The mutant phytases of the present invention exhibit such improved attributes without sacrificing their thermostability, in that the mutant phytases have equal or better thermostability than their non-mutant counterpart phytases. The mutant phytases of the present invention may also be useful to produce specific inositol phosphate metabolites or products for nutritional and biomedical applications.

BRIEF DESCRIPTION OF THE DRAWINGS

FIG. 5B=0.2 M, pH 3.5) or sodium acetate (FIG. 5C=0.01 M; FIG. 5D=0.1 M, pH 5.5). Results are representative of three independent experiments. Values within the same temperature group not sharing a common letter differ ($P<0.05$).

FIG. 8A: 50Q. FIG. 8B: 91K. FIG. 8C: 94K. FIG. 8D: 228K. FIG. 8E: 262E. FIG. 8F: 300K. FIG. 8G: 301K.

FIG. 10A: WT, 2: K300R, 3: K300T, 4: K300D, 5: K94E, 6: E228K, 7: K301E, and M: Marker; 0.1 U enzyme was loaded/lane. FIG. 10B: EndoHf: Deglycosylase control, DG: Deglycosylated phytase, G: phytase with glycosylation, M: molecular size markers.

FIG. 12 is a diagram showing the amino acid comparisons of three PhyA phytases; namely, *A. terreus* phytase (SEQ ID NO:14), *A. niger* phytase (SEQ ID NO:2), and *A. fumigatus* phytase (SEQ ID NO:4).

FIG. 13A: Combination of 300 & 301, FIG. 13B: Combination of 94 and others, FIG. 13C: Combination of 228 & 300, FIG. 13D: Combination of 228, 300 & 301, FIG. 13E: Combination of 91, 228 & 300, FIG. 13F: *A. terreus* mimic mutant.

DETAILED DESCRIPTION

Figure 1:
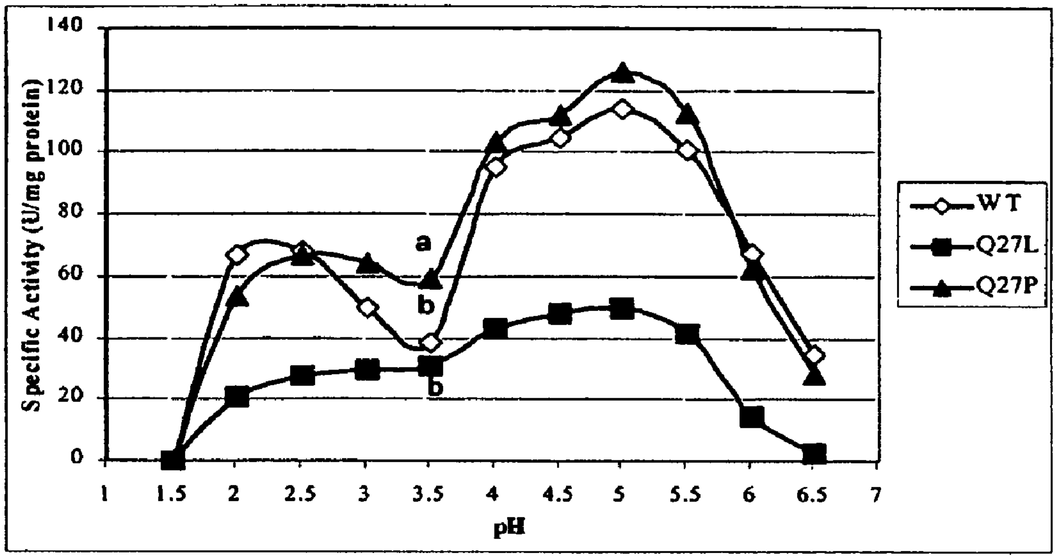
FIG. 1 is a graph showing the pH profiles of *A. niger* wild-type ("WT") phytase and mutations Q27L and Q27P. Results are means of three independent determinations. Means at pH 3.5 not sharing a common letter differ ($P<0.05$). For the rest of pH profile points, mutant Q27L is significantly lower than the WT.

The present invention relates to an isolated nucleic acid molecule encoding a mutant phytase. In one embodiment, the isolated nucleic acid molecule of the present invention can encode a mutant phytase that has an amino acid sequence having at least 96 percent sequence identity to SEQ ID NO:2 over a region of at least 100 amino acid residues. In this embodiment, the amino acid sequence of the mutant phytase can contain at least one substitution of at least one amino acid residue corresponding to residue 50, 91, 94, 228, 262, 300, and/or 301 of SEQ ID NO:2. In another embodiment, the isolated nucleic acid molecule of the present invention can encode a mutant phytase that has an amino acid sequence having at least 96 percent sequence identity to SEQ ID NO:4 over a region of at least 100 amino acid residues. In this embodiment, the amino acid sequence of the mutant phytase can contain a substitution corresponding to amino acid residue 363 of SEQ ID NO:4.

As referred to herein, SEQ ID NO:2 is the amino acid sequence of the wild-type ("WT") *Aspergillus niger* phytase (Genank protein P34752), and has an amino acid sequence as follows:

```
Met Gly Val Ser Ala Val Leu Leu Pro Leu Tyr Leu Leu Ser Gly Val
 1               5                   10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Gln Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430
```

-continued

```
Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

As referred to herein, SEQ ID NO:1 corresponds to the nucleotide sequence of the wild-type *Aspergillus niger* phytase (GenBank Protein M94550) and has the following nucleotide sequence:

```
gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccqcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcgaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacqactacc tccagtcctt   1680

gaaaaagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860
```

-continued

```
ttcgcatgac aacggcatca tctccattct ctttgcttta ggtctgtaca acggcactaa   1920

gccgctatct accacgaccg tggagaatat cacccagaca gatggactct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

cgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc cctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                          2665
```

As referenced herein, amino acid substitutions may be indicated using conventional one-letter abbreviations for the amino acid residues involved in the substitutions. Table 1 describes the one-letter and three-letter codes for the various amino acid residues.

TABLE 1

Three-Letter and One-Letter Codes for Amino Acid Residues

| Amino Acid | 3-Letter Code | 1-Letter Code |
|---|---|---|
| Alanine | Ala | A |
| Cysteine | Cys | C |
| Aspartic acid or aspartate | Asp | D |
| Glutamic acid or glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

As generally described herein, a single amino acid residue substitution can be indicated as follows: the original amino acid residue (expressed as a single-letter abbreviation), followed by the position of the original amino acid residue (i.e., a numerical expression), followed by the new amino acid residue (expressed as a single-letter abbreviation) to be inserted in place of the original amino acid residue. For example, "Q50L" means that the original glutamine (Q) residue at position 50 is to be replaced by the new leucine (L) residue. For multiple substitutions (e.g., double-substitutions, triple-substitutions, and quadruple-substitutions), the various substitutions are separated by either a slash (/) or by a space. An example of a double-substitution may be expressed as either "K300T/E228K" or as "K300T E228K." In such a double-substitution, there are two mutations: the K residue at position 300 is replaced with a T residue, and the E residue at position 228 is replaced with a K residue.

With respect to the isolated nucleic acid molecules of the present invention that encode mutant phytases that have at least 96 percent sequence identity to SEQ ID NO:2 over a region of at least 100 amino acid residues, the at least one substitution can be, without limitation, as follows:

The at least one substitution can be of an amino acid residue corresponding to amino acid residue 50 of SEQ ID NO:2. Examples of suitable substitutions of an amino acid residue corresponding to residue 50 of SEQ ID NO:2 can include Q50L (nucleotide sequence=SEQ ID NO:11, amino acid sequence=SEQ ID NO:12) and Q50P (nucleotide sequence=SEQ ID NO:5, amino acid sequence=SEQ ID NO:6).

The at least one substitution can also be of an amino acid residue corresponding to amino acid residue 91 of SEQ ID NO:2. Examples of suitable substitutions of an amino acid residue corresponding to residue 91 of SEQ ID NO:2 can include K91A (nucleotide sequence=SEQ ID NO:15, amino acid sequence=SEQ ID NO:16) and K91E (nucleotide sequence=SEQ ID NO:17, amino acid sequence=SEQ ID NO:18).

The at least one substitution can also be of an amino acid residue corresponding to amino acid residue 94 of SEQ ID NO:2. Examples of suitable substitutions of an amino acid residue corresponding to residue 94 of SEQ ID NO:2 can include K94E (nucleotide sequence=SEQ ID NO:19, amino acid sequence=SEQ ID NO:20).

The at least one substitution can also be of an amino acid residue corresponding to amino acid residue 228 of SEQ ID NO:2. Examples of suitable substitutions of an amino acid residue corresponding to residue 228 of SEQ ID NO:2 can include E228Q (nucleotide sequence=SEQ ID NO:21, amino acid sequence=SEQ ID NO:22) and E228K (nucleotide sequence=SEQ ID NO:23, amino acid sequence=SEQ ID NO:24).

The at least one substitution can also be of an amino acid residue corresponding to amino acid residue 262 of SEQ ID NO:2. Examples of suitable substitutions of an amino acid residue corresponding to residue 262 of SEQ ID NO:2 can include D262H (nucleotide sequence=SEQ ID NO:25, amino acid sequence=SEQ ID NO:26).

The at least one substitution can also be of an amino acid residue corresponding to amino acid residue 300 of SEQ ID NO:2. Examples of suitable substitutions of an amino acid residue corresponding to residue 300 of SEQ ID NO:2 can include K300R (nucleotide sequence=SEQ ID NO:27, amino acid sequence=SEQ ID NO:28), K300T (nucleotide sequence=SEQ ID NO:29, amino acid sequence=SEQ ID NO:30), K300D (nucleotide sequence=SEQ ID NO:31, amino acid sequence=SEQ ID NO:32), and K300E (nucleotide sequence=SEQ ID NO:7, amino acid sequence=SEQ ID NO:8).

The at least one substitution can also be of an amino acid residue corresponding to amino acid residue 301 of SEQ ID NO:2. Examples of suitable substitutions of an amino acid residue corresponding to residue 301 of SEQ ID NO:2 can include K301E (nucleotide sequence=SEQ ID NO:33, amino acid sequence=SEQ ID NO:34).

The at least one substitution can also be a double-substitution. Examples of suitable double-substitutions can include, without limitation, substitutions of at least two different amino acid residues corresponding to the following substitutions of SEQ ID NO:2: (1) K300E/K301E (nucleotide sequence=SEQ ID NO:35, amino acid sequence=SEQ ID NO:36); (2) K300D/E228K (nucleotide sequence=SEQ ID NO:37, amino acid sequence=SEQ ID NO:38); (3) K300T/E228K (nucleotide sequence=SEQ ID NO:68, amino acid sequence=SEQ ID NO:69); (4) K300R/E228K (nucleotide sequence=SEQ ID NO:39, amino acid sequence=SEQ ID NO:40); and (5) E228K/K94E (nucleotide sequence=SEQ ID NO:41, amino acid sequence=SEQ ID NO:42).

The at least one substitution can also be a triple-substitution. Examples of suitable triple-substitutions can include, without limitation, substitutions of at least three different amino acid residues corresponding to the following substitutions of SEQ ID NO:2: (1) K300R/K301E/E228K (nucleotide sequence=SEQ ID NO:43, amino acid sequence=SEQ ID NO:44); (2) K300T/K301E/E228K (nucleotide sequence=SEQ ID NO:45, amino acid sequence=SEQ ID NO:46); (3) K300D/K301E/E228K (nucleotide sequence=SEQ ID NO:47, amino acid sequence=SEQ ID NO:48); (4) K300E/K301E/K94E (nucleotide sequence=SEQ ID NO:49, amino acid sequence=SEQ ID NO:50); (5) K301E/E228K/K94E (nucleotide sequence=SEQ ID NO:51, amino acid sequence=SEQ ID NO:52); and (6) K300E/K91A/E228Q (nucleotide sequence=SEQ ID NO:53, amino acid sequence=SEQ ID NO:54).

The at least one substitution can further be a quadruple-substitution. Examples of suitable quadruple-substitutions can include, without limitation, substitutions of at least four different amino acid residues corresponding to the following substitutions of SEQ ID NO:2: K300D/K94A/E228A/D262A (nucleotide sequence=SEQ ID NO:55, amino acid sequence=SEQ ID NO:56).

With respect to the isolated nucleic acid molecules of the present invention that encode mutant phytases that have at least 96 percent sequence identity to SEQ ID NO:4 over a region of at least 100 amino acid residues, the substitution of an amino acid residue corresponding to residue 363 of SEQ ID NO:4 can be, without limitation, M362L (nucleotide sequence=SEQ ID NO:9, amino acid sequence=SEQ ID NO:10).

Other suitable phytases that can be used in the various aspects of the present invention as templates for amino acid residue substitutions can be derived from various sources, including, without limitation, from wild-type phytases of *Aspergillus fumigatus* (nucleotide sequence=SEQ ID NO:3, amino acid sequence=SEQ ID NO:4) and/or *Aspergillus terreus* (nucleotide sequence=SEQ ID NO:13, amino acid sequence=SEQ ID NO:14) (see FIG. 12).

The isolated nucleic acid molecules of the present invention can also comprise a nucleotide sequence that is 99 percent homologous to SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68, or a nucleotide sequence of at least 18 contiguous nucleic acid residues that hybridize to SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68 under any of the following stringent conditions: (a) 6×SSC at 68° C.; (b) 5×SSC and 50% formamide 37° C.; or (c) 2×SSC and 40% formamide at 40° C.

Generally, suitable stringent conditions for nucleic acid hybridization assays or gene amplification detection procedures are as set forth above or as identified in Southern, "Detection of Specific Sequences Among DNA Fragments Separated by Gel Electrophoresis," *J. Mol. Biol.* 98:503-17 (1975), which is hereby incorporated by reference in its entirety. For example, conditions of hybridization at 42° C. with 5×SSPE and 50% formamide with washing at 50° C. with 0.5×SSPE can be used with a nucleic acid probe containing at least 20 bases, preferably at least 25 bases or more preferably at least 30 bases. Stringency may be increased, for example, by washing at 55° C. or more preferably 60° C. using an appropriately selected wash medium having an increase in sodium concentration (e.g., 1×SSPE, 2×SSPE, 5×SSPE, etc.). If problems remain with cross-hybridization, further increases in temperature can also be selected, for example, by washing at 65° C., 70° C., 75° C., or 80° C. By adjusting hybridization conditions, it is possible to identify sequences having the desired degree of homology (i.e., greater than 80%, 85%, 90%, or 95%) as determined by the TBLASTN program (Altschul, S. F., et al., "Basic Local Alignment Search Tool," *J. Mol. Biol.* 215:403-410 (1990), which is hereby incorporated by reference in its entirety) on its default setting.

The present invention also relates to nucleic acid molecules having at least 8 nucleotides (i.e., a hybridizable portion) of the nucleic acid molecules of SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68. In other embodiments, the nucleic acid molecules have at least 12 (continuous) nucleotides, 18 nucleotides, 25 nucleotides, 50 nucleotides, 100 nucleotides, 150 nucleotides, or 200 nucleotides of SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68. The invention also relates to nucleic acid molecules hybridizable to or complementary to the foregoing sequences or their complements. In specific aspects, nucleic acid molecules are provided which comprise a sequence complementary to at least 10, 25, 50, 100, or 200 nucleotides or the entire coding region of the isolated nucleic acid molecules encoding the mutant phytase of the present invention.

In a specific embodiment, a nucleic acid molecule which is hybridizable to a nucleic acid molecule of the present invention (e.g., having sequence SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68, or an at least 10, 25, 50, 100, or 200 nucleotide portion thereof), or to a nucleic acid molecule encoding a derivative of a nucleic acid molecule of the present invention, under conditions of low stringency is provided. By way of example and not limitation, procedures using such conditions of low stringency are as follows (see also Shilo et al., *PNAS USA* 78:6789-6792 (1981), which is hereby incorporated by reference in its entirety): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×$10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

In another specific embodiment, a nucleic acid molecule which is hybridizable to a nucleic acid molecule of the present invention under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5-20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

Also suitable as an isolated nucleic acid molecule according to the present invention is an isolated nucleic acid molecule including at least 20 contiguous nucleic acid residues that hybridize to a nucleic acid having a nucleotide sequence of SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68, or the complements of SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68, under stringent conditions. Homologous nucleotide sequences can be detected by selectively hybridizing to each other. The term "selectively hybridizing" is used herein to mean hybridization of DNA or RNA probes from one sequence to the "homologous" sequence under stringent conditions which are characterized by a hybridization buffer comprising 2×SSC, 0.1% SDS at 56° C. (Ausubel et al., eds., *Current Protocols in Molecular Biology* Vol. I, New York: Greene Publishing Associates, Inc. and John Wiley & Sons, Inc., p. 2.10.3 (1989), which is hereby incorporated by reference in its entirety). Another example of suitable stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μg/ml *E. coli* DNA. In one embodiment, the present invention is directed to isolated nucleic acid molecules having nucleotide sequences containing at least 20 contiguous nucleic acid residues that hybridize to the nucleic acid molecules of the present invention, including, SEQ ID NO:5, SEQ ID NO:7, SEQ ID NO:9, SEQ ID NO:11, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:68 under stringent conditions including 50 percent formamide at 42° C.

Alternatively, or additionally, two nucleic acid sequences are substantially identical if they hybridize under high stringency conditions. By "high stringency conditions" is meant conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually 16 nucleotides or longer for PCR or sequencing and 40 nucleotides or longer for in situ hybridization). The high stringency conditions used in these techniques are well known to those skilled in the art of molecular biology, and examples of them can be found, for example, in Ausubel et al., *Current Protocols in Molecular Biology* John Wiley & Sons, New York, N.Y., 1998, which is hereby incorporated by reference in its entirety.

The present invention also relates to a recombinant DNA expression system containing a nucleic acid molecule of the present invention. The nucleic acid molecule can be in a heterologous expression vector.

The present invention further relates to a host cell containing a heterologous nucleic acid molecule of the present invention. The host cell can be a yeast cell or a non-yeast cell. Examples of particular yeast host cells include, without limitation, *Saccharomyces, Kluyveromyces, Torulaspora, Schizosaccharomyces, Pichia, Hansenula, Torulupsis, Candida*, and *Karwinskia*. In another preferred embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera *Pichia, Hansenula, Torulopsis, Candida*, and *Karwinskia*. These yeast genera can use methanol as a sole carbon source. In a more preferred embodiment, the methylotrophic yeast strain is *Pichia pastoris*. Examples of particular non-yeast host cells include, without limitation, bacterial and fungal cells. Suitable examples of non-yeast fungal host cells can include *Aspergillus* species, *Trichoderma* species, and *Neurospora* species.

The present invention also relates to a method of recombinantly producing a mutant phytase. This method involves transforming a host cell with at least one heterologous nucleic acid molecule of the present invention under conditions suitable for expression of the mutant phytase. The mutant phytase is then isolated. Suitable host cells for this method are as described herein (above).

The isolated nucleic acid molecule of the present invention can be expressed in any prokaryotic or eukaryotic expression system by incorporation of the isolated nucleic acid molecule of the present invention in the expression system in proper orientation and correct reading frame. A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used. For example, an isolated nucleic acid molecule in accordance with the present invention is spliced in frame with a transcriptional enhancer element.

The present invention also provides a yeast strain having a heterologous gene which encodes a mutant phytase with phytase activity. The heterologous gene should be functionally linked to a promoter capable of expressing the mutant phytase in yeast.

Yet another aspect of the invention is a vector for expressing the mutant phytase (encoded by the isolated nucleic acid molecule of the present invention) in yeast. The isolated nucleic acid molecule of the present invention can be cloned into any vector which replicates autonomously or integrates into the genome of yeast. The copy number of autonomously replicating plasmids, e.g. YEp plasmids, may be high, but their mitotic stability may be insufficient (Bitter et al., "Expression and Secretion Vectors for Yeast," *Meth. Enzymol.* 153:516-44 (1987), which is hereby incorporated by reference in its entirety). They may contain the 2 mu-plasmid sequence responsible for autonomous replication, and an *E. coli* sequence responsible for replication in *E. coli*. The vectors preferably contain a genetic marker for selection of yeast transformants, and an antibiotic resistance gene for selection in *E. coli*. The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (Struhl et al., "High-Frequency Transformation of Yeast: Autonomous Replication of Hybrid DNA Molecules," *Proc. Nat'l Acad. Sci. USA* 76:1035-39 (1979); Powels et al., *Cloning Vectors, I-IV, et seq.* Elsevier, (1985); and Sakai et al., "Enhanced Secretion of Human Nerve Growth Factor from *Saccharomyces Cerevisiae* Using an Advanced 6-Integration System," *Biotechnology* 9:1382-85 (1991), which are hereby incorporated by reference in their entirety). Some vectors have an origin of replication, which functions in the selected host cell. Suitable origins of replication include 2μ, ARS1, and 25 μM. The vectors have restriction endonuclease sites for insertion of the fusion gene and promoter sequences, and selection markers. The vectors may be modified by removal or addition of restriction sites, or removal of other unwanted nucleotides.

The isolated nucleic acid molecule of the present invention can be placed under the control of any promoter (Stetler et al., "Secretion of Active, Full- and Half-Length Human Secretory Leukocyte Protease Inhibitor by *Saccharomyces cerevisiae*," *Biotechnology* 7:55-60, (1989), which is hereby incorporated by reference in its entirety). One can choose a constitutive or regulated yeast promoter. Suitable promoter sequences for yeast vectors include, among others, promoters for metallothionein, 3-phosphoglycerate kinase (Hitzeman et al., *J. Biol. Chem.* 255:2073 (1980), which is hereby incorporated by reference in its entirety) or other glycolytic enzymes (Hess et al., *J. Adv. Enzyme Reg.* 7:149 (1968); and Holland et al., *Biochem.* 17:4900, (1978), which are hereby incorporated by reference in their entirety), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in EP A-73,657 to Hitzeman, which is hereby incorporated by reference in its entirety. Another alternative is the glucose-repressible ADH2 promoter described by Russell et al., *J. Biol. Chem.* 258:2674 (1982) and Beier et al., *Nature* 300:724 (1982), which are hereby incorporated by reference in their entirety.

The strong promoters of e.g., phosphoglycerate kinase (PGK) gene, other genes encoding glycolytic enzymes, and the alpha-factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP150 terminator, or any other functional terminator is used. Here, promoters and terminators are called control elements. The present invention is not restricted to any specific vector, promoter, or terminator.

The vector may also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, or antibiotic resistance genes.

The vector may also have an origin of replication capable of replication in a bacterial cell. Manipulation of vectors is more efficient in bacterial strains. Preferred bacterial origin of replications are ColE1, Ori, or oriT.

Preferably, the mutant phytase encoded by the isolated nucleic acid molecule of the present invention is secreted by the cell into growth media. This allows for higher expression levels and easier isolation of the product. The mutant phytase is coupled to a signal sequence capable of directing the protein out of the cell. Preferably, the signal sequence is cleaved from the protein.

A leader sequence either from the yeast or from phytase genes or other sources can be used to support the secretion of expressed mutant phytase enzyme into the medium. The present invention is not restricted to any specific type of leader sequence or signal peptide.

Suitable leader sequences include the yeast alpha factor leader sequence, which may be employed to direct secretion of the mutant phytase. The alpha factor leader sequence is often inserted between the promoter sequence and the structural gene sequence (Kurjan et al., *Cell* 30:933, (1982); Bitter et al., *Proc. Natl. Acad. Sci. USA* 81:5330, (1984); U.S. Pat. No. 4,546,082; and European Patent Application No. 324, 274, which are hereby incorporated by reference in their entirety). Another suitable leader sequence is the *S. cerevisiae* MF alpha 1 (alpha-factor) which is synthesized as a prepro form of 165 amino acids comprising signal-or prepeptide of 19 amino acids followed by a "leader" or propeptide of 64 amino acids, encompassing three N-linked glycosylation sites followed by (LysArg(Asp/Glu, Ala)2-3 alpha-factor)$_4$ (Kurjan, et al., *Cell* 30:933-43 (1982), which is hereby incorporated by reference in its entirety). The signal-leader part of the preproMF alpha 1 has been widely employed to obtain synthesis and secretion of heterologous proteins in *S. cerivisiae*. Use of signal/leader peptides homologous to yeast is known from: U.S. Pat. No. 4,546,082; European Patent Applications Nos. 116,201, 123,294, 123,544, 163,529, and 123,289; and DK Patent Application No. 3614/83, which are hereby incorporated by reference in their entirety. In European Patent Application No. 123,289, which is hereby incorporated by reference in its entirety, utilization of the *S. cerevisiae* a-factor precursor is described whereas WO 84/01153, which is hereby incorporated by reference in its entirety, indicates utilization of the *Saccharomyces cerevisiae* invertase signal peptide, and German Patent Application DK 3614/83, which is hereby incorporated by reference in its entirety, indicates utilization of the *Saccharomyces cerevisiae* PH05 signal peptide for secretion of foreign proteins.

The alpha-factor signal-leader from *Saccharomyces cerevisiae* (MF alpha 1 or MF alpha 2) may also be utilized in the secretion process of expressed heterologous proteins in yeast (U.S. Pat. No. 4,546,082; European Patent Applications Nos. 16,201, 123,294, 123,544, and 163,529, which are hereby incorporated by reference in their entirety). By fusing a DNA sequence encoding the *S. cerevisiae* MF alpha 1 signal/leader sequence at the 5' end of the gene for the desired protein, secretion and processing of the desired protein was demonstrated. The use of the mouse salivary amylase signal peptide (or a mutant thereof) to provide secretion of heterologous proteins expressed in yeast has been described in WO 89/02463 and WO 90/10075, which are hereby incorporated by reference in their entirety.

U.S. Pat. No. 5,726,038 describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929 (1978), which is hereby incorporated by reference in its entirety. The Hinnen et al. protocol selects for Trp transformants in a selective medium, wherein the selective medium consists of 0.67% yeast nitrogen base, 0.5% casamino acids, 2% glucose, 10 μg/ml adenine, and 20 μg/ml uracil.

The isolated nucleic acid molecule of the present invention may be maintained in a stable expression vector, an artificial chromosome, or by integration into the yeast host cell chromosome. Integration into the chromosome may be accomplished by cloning the mutant phytase gene into a vector which will recombine into a yeast chromosome. Suitable vectors may include nucleotide sequences which are homologous to nucleotide sequences in the yeast chromosome. Alternatively, the mutant phytase gene may be located between recombination sites, such as transposable elements, which can mobilize the gene into the chromosome.

The present invention also relates to an isolated mutant phytase. In one embodiment, the mutant phytase of the present invention can have an amino acid sequence having at least 96 percent sequence identity to SEQ ID NO:2 over a region of at least 100 amino acid residues. In this embodiment, the amino acid sequence of the mutant phytase can contain at least one substitution of at least one amino acid residue corresponding to residue 50, 91, 94, 228, 262, 300, and/or 301 of SEQ ID NO:2. In another embodiment, the mutant phytase of the present invention can have an amino acid sequence having at least 96 percent sequence identity to SEQ ID NO:4 over a region of at least 100 amino acid residues. In this embodiment, the amino acid sequence of the mutant phytase can contain a substitution of an amino acid residue corresponding to residue 363 of SEQ ID NO:4. Specific suitable amino acid substitutions are as already described herein (see above). The isolated mutant phytase can be in pure or non-pure form. The isolated mutant phytase can also be recombinant.

A purified protein or polypeptide of the mutant phytase of the present invention can be obtained by several methods. The purified protein or polypeptide of the mutant phytase of the present invention is preferably produced in pure form (preferably at least about 80%, more preferably 90%, pure) by conventional techniques well known in the art. Typically, the purified protein or polypeptide of the mutant phytase of the present invention is secreted into the growth medium of recombinant host cells. Alternatively, the purified protein or polypeptide of the mutant phytase of the present invention is produced but not secreted into growth medium. In such cases, to isolate the protein or polypeptide of the mutant phytase, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the mutant phytase of the present invention is subjected to gel filtration in an appropriately sized dextran or polyacrylamide column to separate the proteins. If necessary, the protein fraction (containing the mutant phytase of the present invention) may be further purified by HPLC.

The present invention also relates to an animal feed composition. The animal feed composition can contain the isolated mutant phytase of the present invention. The present invention further relates to a food stuff containing the animal feed composition. The foodstuff can further contain greater than 1.0 percent by weight of a vitamin and mineral mix. The foodstuff can also further include soybean meal. The foodstuff can still further include antibiotics.

The mutant phytase of this invention can be used in an animal feed composition to improve the digestion of phosphate by various "animals" (as defined below). The present invention would decrease the need for supplementing animal feed with large amounts of inorganic phosphate, resulting in a less expensive form of animal feed and one that is less concentrated with the non-renewable form of phosphate. Since the present invention enhances the ability of simple-stomached animals to absorb phosphate, the fecal waste of these animals will contain less unutilized phytate-phosphate, which decreases the amount of phosphate pollution.

As used herein, the term "animals" includes domestic and non-domestic animals, and includes, without limitation, fowl species, porcine species, aquatic species, canine species, feline species, and humans. Other suitable animals that are encompassed by the term "animals" include, without limitation, mammalian species such as an *Oryctolagus* species, a *Capra* species, a *Bos* species, an *Equus* species, and/or an *Ovis* species. Further, all physiological stages (infant, juvenile, adult) of a particular species described herein are meant to be encompassed by the scope of the present invention. Thus, the term "animals" includes such simple-stomached animals as poultry, swine, pre-ruminant calves, zoo animals, and pets (e.g., cats and dogs).

In making the animal feed composition of the present invention, the mutant phytase is combined with a raw plant material and then processed into a pellet or powder form. The raw plant material may include various combinations of a number of plants and/or plant by-products commonly used in animal feed, including plants such as maize, soybean, wheat, rice, cotton seed, rapeseed, sorghum, and potato. In addition, the animal feed composition may be fortified with various vitamins, minerals, animal protein, and antibiotics. One embodiment of the animal feed composition includes a mixture of appropriate concentrations of the mutant phytase, an energy source(s) (e.g., maize, wheat), a protein source(s) (e.g., soybean, rice, cottonseed meal, rapeseed meal, sorghum meal), and vitamin/mineral supplements. In particular, the amount of the mutant phytase can be between about 100-2,000 Units/kg of feed. In another embodiment, the amount of the mutant phytase can be between about 200-1,500 Units/kg of feed. In yet another embodiment, the amount of the mutant phytase can be between about 300-1,000 Units/kg of feed. One example of a typical animal feed composition would include 50-70% maize, 20-30% soybean, approximately 1% vitamin and mineral supplements, and an appropriate amount of mutant phytase.

In addition, the mutant phytase of the present invention could be used to enhance human nutrition, particularly by increasing the uptake of such minerals as zinc and iron. By adding the mutant phytase to the diets of humans, various problems arising from nutrient deficiencies, such as stunted growth and mental retardation in children, could be treated and avoided.

The present invention also relates to a method of feeding a monogastric animal. This method involves feeding to the animal a foodstuff in combination with the isolated mutant phytase of the present invention. Suitable animals can include, without limitation, the animals described above. In one embodiment, the animal is fed the foodstuff in combination with between about 100-2,000 units of the phytase expressed in yeast per kilogram of the foodstuff. In another embodiment, the animal is fed the foodstuff in combination with between about 200-1,500 units of the phytase expressed in yeast per kilogram of the foodstuff. In yet another embodiment, the animal is fed the foodstuff in combination with between about 300-1,000 units of the phytase expressed in yeast per kilogram of the foodstuff.

The present invention also relates to a method of improving the nutritional value of a foodstuff consumed by an animal. This method involves providing a foodstuff containing myo-inositol hexakisphosphate, and also providing a mutant phytase of the present invention. The animal is then fed the foodstuff in combination with the mutant phytase under conditions effective to increase the bioavailability of phosphate from phytate. Suitable animals are as described above. The animal can also be a human. In one embodiment, the foodstuff can be pig feed. In another embodiment, the foodstuff can be poultry feed. In one embodiment, the animal is fed the foodstuff in combination with between about 100-2,000 units of the phytase expressed in yeast per kilogram of the foodstuff. In another embodiment, the animal is fed the foodstuff in combination with between about 200-1,500 units of the phytase expressed in yeast per kilogram of the foodstuff. In yet another embodiment, the animal is fed the foodstuff in combination with between about 300-1,000 units of the phytase expressed in yeast per kilogram of the foodstuff.

The present invention also relates to a method for altering the enzymatic properties of a wild-type phytase of an *Aspergillus* species. This method involves providing a wild-type phytase of an *Aspergillus* species. Examples of suitable wild-type *Aspergillus* species include, without limitation, *Aspergillus niger* and *Aspergillus fumigatus*. In one embodiment, the wild-type phytase is an *Aspergillus niger* phytase having an amino acid sequence that has at least 96 percent sequence identity to SEQ ID NO:2 over a region of at least 100 amino acid residues. In another embodiment, the wild-type phytase is an *Aspergillus fumigatus* phytase having an amino acid sequence that has at least 96 percent sequence identity to SEQ ID NO:4 over a region of at least 100 amino acid residues. The method also involves altering the amino acid sequence of the wild-type phytase under conditions effective to yield a mutant phytase having a modified substrate binding region and/or improved catalytic efficiency compared to the amino acid sequence of the wild-type phytase. In one embodiment, altering the amino acid sequence involves introducing into the amino acid sequence of an *Aspergillus niger* wild-type phytase at least one substitution of at least one amino acid residue corresponding to residue 50, 91, 94, 228, 262, 300, and/or 301 of SEQ ID NO:2. Suitable specific substitutions can include those already described above. In another embodiment, altering the amino acid sequence involves introducing into the amino acid sequence of the *Aspergillus fumigatus* wild-type phytase a substitution at an amino acid residue corresponding to residue 363 of SEQ ID NO:4. Suitable specific substitutions can include those already described above.

The present invention also relates to a method of in vitro hydrolysis of phytate. This method involves providing a mutant phytase of the present invention. The mutant phytase is combined with a phytate source under conditions effective to increase the bioavailability of phosphate from the phytate source. A suitable phytate source can be, without limitation, an animal feed and/or a foodstuff. The method can further involve combining the mutant phytase with a phytate source under conditions effective to increase the bioavailability of various minerals such as, including, without limitation, calcium, zinc, and/or iron, from the phytate source.

The present invention also relates to a method of improving the nutritional value of a foodstuff consumed by humans. This method involves providing a mutant phytase according to the present invention. The mutant phytase is combined with a foodstuff consumed by humans under conditions effective to increase the bioavailability of minerals from the foodstuff. Suitable minerals can include, without limitation, iron, zinc, phosphorus, and calcium.

The present invention further relates to a method of imparting improved mineral nutritional value to a plant that is edible for consumption by animals. This method involves providing a transgene containing an isolated nucleic acid molecule of the present invention. The isolated nucleic acid molecule is operatively associated with a regulatory sequence containing transcriptional and translational regulatory elements that control expression of the isolated nucleic acid molecule in a transgenic plant cell. The method also involves providing a non-transformed plant that is edible for consumption by animals. The transgene is inserted into the genome of the non-transformed plant under conditions effective to yield a transformed plant that transgenically expresses a mutant phytase encoded by the isolated nucleic acid molecule of the present invention. The resulting transformed plant has improved mineral nutritional value compared to that of the non-transformed plant.

In order to transgenically express the mutant phytase of the present invention in plants, transgenic plants carrying the isolated nucleic acid molecule of the present invention are produced by transforming a plant with a transgene (e.g., a chimeric DNA) construct that expresses the mutant phytase.

In order to express the mutant phytase from the trangene, the construct should include a plant specific promoter. The promoter should ensure that the foreign gene is expressed in the plant. The promoter can be chosen so that the expression occurs only in specified tissues, at a determined time point in the plant's development or at a time point determined by outside influences. The promoter can be homologous or heterologous to the plant. Suitable promoters include, e.g. the RUBISCO small subunit promoter, tissue-specific promoters, the promoter of the 35S RNA of the cauliflower mosaic virus described in U.S. Pat. No. 5,034,322 (which is hereby incorporated by reference in its entirety), the enhanced 35S promoter described in U.S. Pat. No. 5,106,739 (which is hereby incorporated by reference in its entirety), the dual S35 promoter, the FMV promoter from figwort mosaic virus that is described in U.S. Pat. No. 5,378,619 (which is hereby incorporated by reference in its entirety), the RI T-DNA promoter described in U.S. Pat. No. 5,466,792 (which is hereby incorporated by reference in its entirety), the octopine T-DNA promoter described in U.S. Pat. No. 5,428,147 (which is hereby incorporated by reference in its entirety), the alcohol dehydrogenase 1 promoter (Callis et al., *Genes Dev.* 1(10): 1183-1200 (1987), which is hereby incorporated by reference in its entirety), the patatin promoter B33 (Rocha-Sosa et al., *EMBO J.* 8:23-29 (1989), which is hereby incorporated by reference in its entirety), the E8 promoter (Deikman et al., *EMBO J.* 7(11):3315-3320 (1988), which is hereby incorporated by reference in its entirety), the beta-conglycin promoter (Tiemey et al., *Planta* 172:356-363 (1987), which is hereby incorporated by reference in its entirety), the acid chitinase promoter (Samac et al., *Plant Physiol.* 93:907-914 (1990), which is hereby incorporated by reference in its entirety), the *Arabidopsis* histone H4 promoter described in U.S. Pat. No. 5,491,288 (which is hereby incorporated by reference in its entirety), or the recombinant promoter for expression of genes in monocots described in U.S. Pat. No. 5,290,924 (which is hereby incorporated by reference in its entirety).

Preferred promoters include the RUBISCO small subunit promoter, the 35S promoters, fiber enhanced promoters, vascular cell enhanced promoters, stem cell enhanced promoters, or seed enhanced promoters. Such promoters may ensure expression in a tissue specific or tissue-enhanced manner, but may allow expression in other cell types. For example it may ensure enhanced expression in photosynthetically active tissues (RUBISCO (Worrell et al., *The Plant Cell* 3:1121-1130 (1991), which is hereby incorporated by reference in its entirety)) or other mesophyll-cell-specific promoter (Datta et al., *Theor. Appl. Genet.* 97:20-30 (1998), which is hereby incorporated by reference in its entirety). Other promoters can be used that ensure expression only in specified organs, such as the leaf, root, tuber, seed, stem, flower or specified cell types such as parenchyma, epidermal, or vascular cells. One example of a tissue-specific promoter is the RB7 promoter that is root specific (U.S. Pat. No. 5,459,252, which is hereby incorporated by reference in its entirety). Such promoters may be used either alone or in combination to optimize overexpression in the most desirable set of tissues or organs.

In one embodiment of the present invention the, transgene is stably integrated into the genome of the non-transformed plant. When a plant is transformed by *Agrobacterium* mediated transformation, a portion of the Ti plasmid integrates into the plant genome and is stably passed on to future generations of plant cells.

Numerous methods exist for transforming plant cells. The preferred methods include electroporation, *Agrobacterium* mediated transformation, biolistic gene transformation, chemically mediated transformation, or microinjection.

The vector described above can be microinjected directly into plant cells by use of micropipettes to transfer mechanically the recombinant DNA (Crossway, *Mol. Gen. Genetics* 202:179-185 (1985), which is hereby incorporated by reference in its entirety). The genetic material may also be transferred into the plant cell using polyethylene glycol (Krens et al., *Nature* 296:72-74 (1982), which is hereby incorporated by reference in its entirety).

Another approach to transforming plant cells with an isolated nucleic acid molecule of the present invention is particle bombardment (also known as biolistic transformation) of the host cell. This can be accomplished in one of several ways.

The first involves propelling inert or biologically active particles at cells. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies (Fraley et al., *Proc. Natl. Acad. Sci. USA* 79:1859-63 (1982), which is hereby incorporated by reference in its entirety).

The isolated nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the isolated nucleic acid molecule of the present invention into plant cells is to infect a plant cell with *Agrobacterium tumefaciens* or *A. rhizogenes* previously transformed with the isolated nucleic acid molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, *Science* 237:1176-83 (1987), which is hereby incorporated by reference in its entirety).

After transformation, whole transformed plants can be recovered. If transformed seeds were produced directly, these can be selected by germination on selection medium and grown into plants (Glough et al. *The Plant Journal* 16:735-743 (1998), which is hereby incorporated by reference in its entirety). If transformed pollen was produced directly, this can be used for in vivo pollination followed by selection of transformed seeds (Touraev et al., *The Plant Journal* 12:949-956 (1997), which is hereby incorporated by reference in its entirety). If meristems were transformed, these can be grown into plants in culture then transferred to soil (Gould, J. et al., *Plant Cell Rep.* 10:12-16 (1991), which is hereby incorporated by reference in its entirety).

If protoplasts or explants were transformed, plants can be regenerated. Plant regeneration from cultured protoplasts is described in Evans et al., *Handbook of Plant Cell Cultures*, Vol. 1, New York, N.Y.: MacMillan Publishing Co., (1983); and Vasil, ed., *Cell Culture and Somatic Cell Genetics of Plants*, Orlando: Acad. Press, Vol. I (1984), and Vol. III (1986), which are hereby incorporated by reference in their entirety. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

It is known that practically all plants can be regenerated from cultured cells or tissues, including but not limited to, species of sugarcane, sugar beets, cotton, forest trees, forage crops, and fiber producing plants. Regeneration is also possible in seed-producing plants including, but not limited to, maize, rice, wheat, soybean, rape, sunflower, and peanut.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the isolated nucleic acid molecule encoding a mutant phytase of the present invention. Alternatively, transgenic seeds are recovered from the transgenic plants. These seeds can then be planted in the soil and cultivated using conventional procedures to produce transgenic plants.

The mutant phytases of the present invention may also be useful to produce specific inositol phosphate metabolites or products for nutritional and biomedical applications.

EXAMPLES

Example 1

Using Mutations to Improve *Aspergillus* Phytases

As used in Examples 1-13, amino acid residue 27 of the *Aspergillus niger* phytase corresponds to amino acid residue 50 as referenced in SEQ ID NOS:2, 6, and 12, and in the claims of the present application. Also, as used in Examples 1-13, amino acid residue 362 of the *Aspergillus fumigatus* phytase corresponds to amino acid residue 363 as referenced in SEQ ID NOS:4 and 10 and in the claims of the present application.

The objectives of this study included the following: (1) to compare the specific activity of mutants Q27L and Q27P in *A. niger* phytase as well as M362L in *A. fumigatus* phytase with the respective wild-type controls; and (2) to determine the impacts of these single amino acid substitutions on the pH profile and heat-tolerance of the recombinant phytases.

Site-directed mutagenesis was conducted to enhance catalytic activities of *Aspergillus niger* and *A. fumigatus* phytases.

Mutation Q27L in *A. niger* phytase caused a 52% reduction in the specific activity of the recombinant enzyme. However, mutation Q27P improved specific activity by 30-53% at pH 3-3.5, but had no effect on specific activity at its optimal pH of 5. Also, substitution of M362 for L in *A. fumigatus* phytase increased its specific activity by 25%, without major impacts on its pH profile. However, heat-tolerance of these recombinant enzymes was not affected by the site-directed mutagenesis, but was closely associated with the specificity of buffer used in the heat treatment.

Example 2

Phytase Mutations

Plasmid pYPP1 containing the cloned *A. niger* NRRL 3135 phyA phytase gene (Han et al., "Expression of an *Aspergillus niger* Phytase Gene (phyA) in *Saccharomyces cerevisiae*," *Appl. Environ. Microbiol.* 65:1915-1918 (1999), which is hereby incorporated by reference in its entirety) was utilized to generate two mutants of Q27L and Q27P. Based on the published sequence of this phyA phytase gene (GeneBank accession no. M94550), the following oligonucleotides were synthesized to generate site specific mutations at the Gln 27 residue, corresponding to the same residue in *A. fumigatus* (Tomschy et al., "Optimization of the Catalytic Properties of *Aspergillus fumigatus* Phytase Based on the Three-Dimensional Structure," *Protein Science* 9:1304-1311 (2000), which is hereby incorporated by reference in its entirety), Leu 27 5'-CTTT GGGGTCTATACGCACCG-3' (SEQ ID NO:57) and Pro 27 5'-CTTTGGGGTCCATACGCACCG-3' (SEQ ID NO:58). The primers were phosphorylated and the Gene Editor™ in vitro Site-Directed Mutageneis System (Promega, Madison, Wis.) was used to generate the desired mutations. The annealing temperature was 75° C. for 5 min and the reaction was allowed to cool at 1.5° C. per min until 37° C. The presence of the specific mutations in the transformants was confirmed by DNA sequencing.

*Aspergillus fumigatus* phytase gene (*A. fumigatus* SRRC 322) cloned into plasmid pCR2.1 (Invitrogen Corp. San Diego, Calif.) (Mullaney et al., "Phytase Activity in *Aspergillus fumigatus* Isolates," *Biochem. Biophys. Res. Commun.* 275:759-763 (2000), which is hereby incorporated by reference in its entirety) was used as the template for site-directed mutagenesis of M362L. The oligonucleotide 5'-CACGACAACAGCCTGGTTTCCATCTTC-3' (SEQ ID NO:59) was synthesized to generate this mutation. The resulting construct (M362L) was amplified using the following primers: forward: 5'-GCGAATTCTCCAAGTCCTGCGATAC-3' (SEQ ID NO:60) and reverse, 5'-ACATCTAGACTAAAGCACTCTCC-3' (SEQ ID NO:61). The forward and reverse primer contained EcoRI and XbaI restriction site, respectively. Amplified PCR product was cloned into pGEM-T vector (Promega) according to the manufacturer instructions and transformed into TOP10F' (Invitrogen, Carlsbad, Calif.) to screen for positive colonies. The isolated fragment was inserted into pPICZαA (Invitrogen, CA) at the Eco RI and Xba I sites in frame with the alpha factor secretion signal present in the vector. The construct was transformed into TOP10F'-competent cells which were plated on LB medium containing 25 μg zeocin/ml. Positive colonies were grown to prepare DNA for transformation.

Example 3

Yeast Transformation and Protein Expression

*Saccharomyces cerevisiae* INVSc1 (Invitrogen) were grown in yeast extract-peptone-dextrose medium (YPD) and prepared for transformation according to the manufacturer instructions. Plasmid DNA containing Q27L or Q27P was transformed into *Saccharomyces* by electroporation (1.5 KV, 50 μF, 129Ω. ECM 600 Electro Cell Manipulator, Genetronics, BTX Instrument Division, San Diego, Calif.). After incubation for 2 h at 30° C. in 1 M sorbitol without agitation, cells were plated in URA(−) selective medium to screen for positive transformants. Colonies were grown in 9 mL YPD broth for 36-48 h, and then centrifuged at 1,500 rpm, 25° C. for 10 min. The cell pellet was resuspended in YPG medium (1% Yeast extract, 2% peptone, 2% galactose) for induction of the recombinant enzyme expression. Activity in the medium was measured after 24-36 h. Transformation of plasmid DNA containing M362L in *Pichia pastoris* strain X33, and induction of phytase expression were the same as previously described (Rodriguez et al., "Expression of the *Aspergillus fumigatus* Phytase Gene in *Pichia pastoris* and Characterization of the Recombinant Enzyme," *Biochem. Biophys. Res. Commun.* 268:373-378 (2000); and Han et al., "Expression of an *Aspergillus niger* Phytase Gene (phyA) in *Saccharomyces cerevisiae*," *Appl Environ. Microbiol.* 65:1915-1918 (1999), which are hereby incorporated by reference in their entirety).

Example 4

Purification of the Expressed Phytases

All steps were carried out at 4° C. Culture samples were concentrated by ultrafiltration (Amicon Stirred Ultrafiltration Cells. Millipore Corp, Bedford, Mass.). The concentrated phytase solution was loaded onto a DEAE-Cellulose column and eluted using a linear gradient from 0-0.5 M NaCl in Tris.HCl, pH 7.4. Fractions with phytase activity were pooled and concentrated using Macrosep Centrifugal concentrators (Pall Filtron Corp, Northborough, Mass.) before loading onto a Sephadex G-75 gel filtration column equilibrated with 10 mM citrate buffer, pH 5.5.

Example 5

Phytase Activity and Properties

Enzyme activity was determined as previously described (Han et al., "Role of Glycosylation in the Functional Expression of an *Aspergillus niger* Phytase (phyA) in *Pichia pastoris*," *Arch. Biochem. Biophys.* 364:83-90 (1999); and Han et al., "Expression of an *Aspergillus niger* Phytase Gene (phyA) in *Saccharomyces cerevisiae*," *Appl. Environ. Microbiol.* 65:1915-1918 (1999), which are hereby incorporated by reference in their entirety). One phytase unit is the amount of enzyme that releases 1 μmol of inorganic phosphorus from sodium phytate at pH 5 and 37° C. The pH profile of the different phytases expressed was determined using the following buffers: 0.2 M glycine.HCl for pH 2-3.5; 0.2 M citrate for pH 4-6.5; 0.2 M Tris.HCl for pH 7-8.5. Sodium phytate was used as substrate. It was dissolved in the same buffers used for the pH profile curve. For a comparison of their thermotolerance, the purified enzymes were diluted up to a protein concentration of 25 μg/mL in a final volume of 500 μl using two different buffers: glycine.HCl, pH 3.5 (0.01 M or 0.2 M), and sodium acetate buffer, pH 5.5 (0.01 M or 0.1 M). The samples were subjected to 37° C., 55° C., and 85° C. for 15 min and chilled on ice for another 15 min prior to phytase activity determination. Results are expressed as percentage of remaining activity compared to the untreated control samples.

Example 6

SDS-PAGE

Samples of purified protein were subjected to 13% SDS-PAGE using a Mini-Protein II Cell (Bio-Rad Laboratories, Hercules, Calif.) (Laemmli, "Cleavage of Structural Proteins During the Assembly of the Head of Bacteriophage T4," *Nature* 227:680-685 (1970), which is hereby incorporated by reference in its entirety). Protein was stained with Coomassie Brilliant Blue R-250. The molecular weight marker used was prestained SDS-PAGE standard (Broad Range, Bio-Rad Laboratories, Hercules, Calif.). Protein concentration was determined using the method of Lowry et al., *J. Biol. Chem.* 193:265-275 (1951), which is hereby incorporated by reference in its entirety.

Example 7

Deglycosylation of Phytase

Deglycosylation of different phytases was done using 0.075 units of endoglycosidase Hf (Endo Hf) for 2 h at 37° C. according to the manufacturer instructions (New England Biolabs, Beverly, Mass.). The deglycosylated proteins were also analyzed in a 13% SDS-PAGE.

Example 8

Statistics

Data on specific activity and pH profiles of *A. niger* WT, Q27L, and Q27P were analyzed using one-way ANOVA (SAS Institute, Inc. Cary, N.C.), with Duncan test for mean comparisons. Differences in specific activity between *A. fumigatus* WT phytase and M362L (Table 2) were analyzed using student's t-test. Thermotolerance data from three different *A. niger* phytases were pooled due to the lack of difference to determine the effect of our test buffer conditions, using student's t-test. Thermotolerance data of the two *A. fumigatus* phytases were analyzed using one-way ANOVA, and Duncan's test was applied to compare the effects of buffer specificity at a given temperature.

Example 9

Mutations Q27L and Q27P of *A. niger* Phytase and M362L of *A. fumigatus* Phytase Affect Specific Activity of the Enzymes at pH 5

Specific activity was determined at the optimal pH of 5 in all the WT and mutant phytases, with two or three independent purifications. Compared with the wild type, mutant Q27L reduced its specific activity by 52% (54.6 vs 113.6 U/mg) (Table 2), while mutant Q27P showed a 13% increase (127.8 vs 113.6 U/mg). The mutation M362L in *A. fumigatus* phytase increased specific activity by 25% over the wild type control (63.6 vs 49.8 U/mg) ($P<0.05$).

TABLE 2

Specific Activity of *A. fumigatus* and *A. niger* WT and Mutant Phytases at pH 5.0.

| PHYTASE | U/mg protein (means ± S.D.) | N |
|---|---|---|
| *A. niger* WT | $113.6 \pm 8.67^a$ | 3 |
| Q27L | $54.57 \pm 8.24^b$ | 3 |
| Q27P | $127.8 \pm 11.16^a$ | 3 |
| *A. fumigatus* WT | $49.8 \pm 9.02^A$ | 4 |
| *A. fumigatus* M362L | $63.6 \pm 2.9^B$ | 4 |

N = number of measurements.
*A. niger*: a vs b ($P < 0.05$);
*A. fumigatus*: A vs B ($P < 0.05$)

Example 10

Mutations Q27L and Q27P Affect the pH Profile of *A. niger* Phytase

Figure 2:
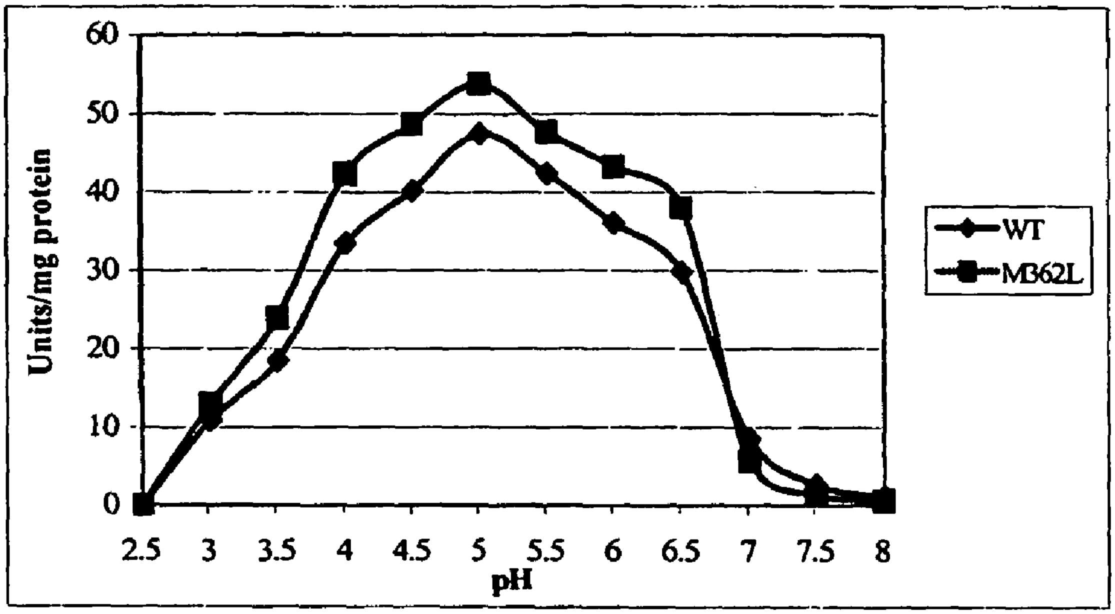
FIG. 2 is a graph showing the pH profile of *A. fumigatus* WT phytase and mutation M362L. Results are means of 4 independent measurements.

*A. niger* WT phytase showed the characteristic two pH optimum at 2.5 and 5, and lower values for specific activity at pH 3 and 3.5 (FIG. 1). Specific activity for Q27L was significantly lower than the WT enzyme at all tested pH points with the exception of pH 3.5 at which no difference was found. Mutant Q27P exhibited a general increase in specific activity at most points of the pH profile compared with the wild type, although differences were only significant at pH 3.5 and marginally significant at pH 3 ($P=0.11$). No major change was found in the pH profile of mutation M362L when compared with the WT enzyme (FIG. 2), both enzymes were active over a broad range of pH and displayed relatively high activity between pH 4 and 6.5.

Example 11

Glycosylation of *A. fumigatus* Phytase is Affected by the M362L Mutation

Figure 3:
FIG. 3 shows the results of an SDS-PAGE of purified *A. fumigatus* (6.5 μg) and *A. niger* (3.5 μg) phytases before and after deglycosylation by Endo Hf. Lane M, prestained standard from Bio-Rad. Lane 1, *A. fumigatus* WT phytase expressed in *Pichia pastoris*. Lane 2, mutation M362L expressed in *Pichia pastoris*. Lane 3, *A. fumigatus* WT+Endo Hf. Lane 4, mutation M362L+Endo Hf. Lane 5, Endo Hf. Lane 6, *A. niger* WT phytase expressed in *S. cerevisiae*. Lane 7, Q27L mutant expressed in *S. cerevisiae*. Lane 8, Q27P 1'-mutant expressed in *S. cerevisiae*. Lane 9, *A. niger* WT phytase+Endo Hf. Lane 10, mutant Q27L+Endo Hf Lane 11, mutant Q27P+Endo Hf.

*A. fumigatus* WT phytase showed a greater size than mutant M362L when both were resolved in a 13% SDS-PAGE (FIG. 3). However, after treatment with endoglycosidase Hf, both enzymes had the same size of 49 KD. *A. niger* WT phytase, as well as mutants Q27L and Q27P expressed in *S. cerevisiae*, showed higher levels of glycosylation than *A. fumigatus* WT phytase or M362L expressed in *P. pastoris*. No difference in glycosylation was observed resulting from the site-directed mutations in *A. niger* phytase.

Example 12

Figure 4:
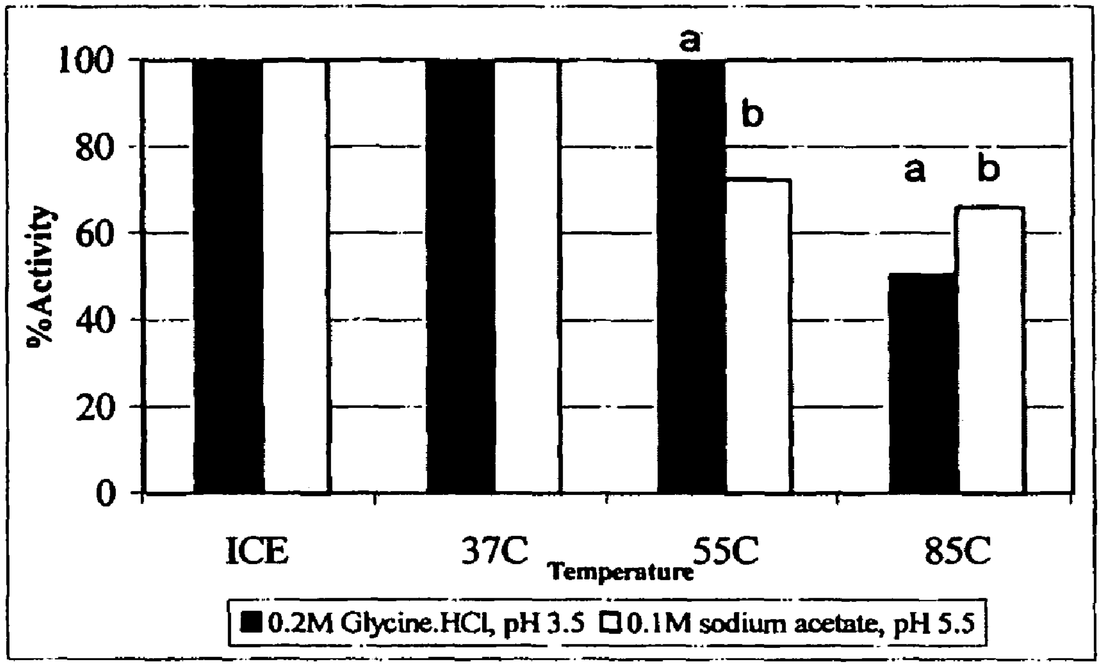
FIG. 4 is a graph showing the residual phytase activity of *A. niger* WT and mutants Q27L and Q27P after exposure for 15 min to the indicated temperatures, in 0.1 M sodium acetate buffer, pH 5.5 or 0.2 M glycine.HCl buffer, pH 3.5. Since there was no significant differences in thermotolerance due to the mutations, results of WT, Q27L, and Q27P phytases are pooled for each temperature point as a single common bar. Results are means of three independent experiments. Values within each individual temperature not sharing a common letter differ ($P<0.05$).

Thermotolerance of Recombinant Phytases is Modulated by the Specificity of the Buffer Used There was no difference in heat tolerance among the three *A. niger* phytases at any given treatment. Data were pooled for individual buffer conditions. *A. niger* phytase retained 30% higher activity after heating at 55° C. in glycine.HCl, pH 3.5 than in sodium acetate, pH 5.5 (FIG. 4). However, sodium acetate enabled a higher residual phytase activity to be retained at 85° C. than glycine.HCl (67 vs 50%). Salt concentrations in the buffers (0.01 M, 0.1 M, or 0.2 M) for a given pH did not affect results for thermotolerance.

Figure 5A:
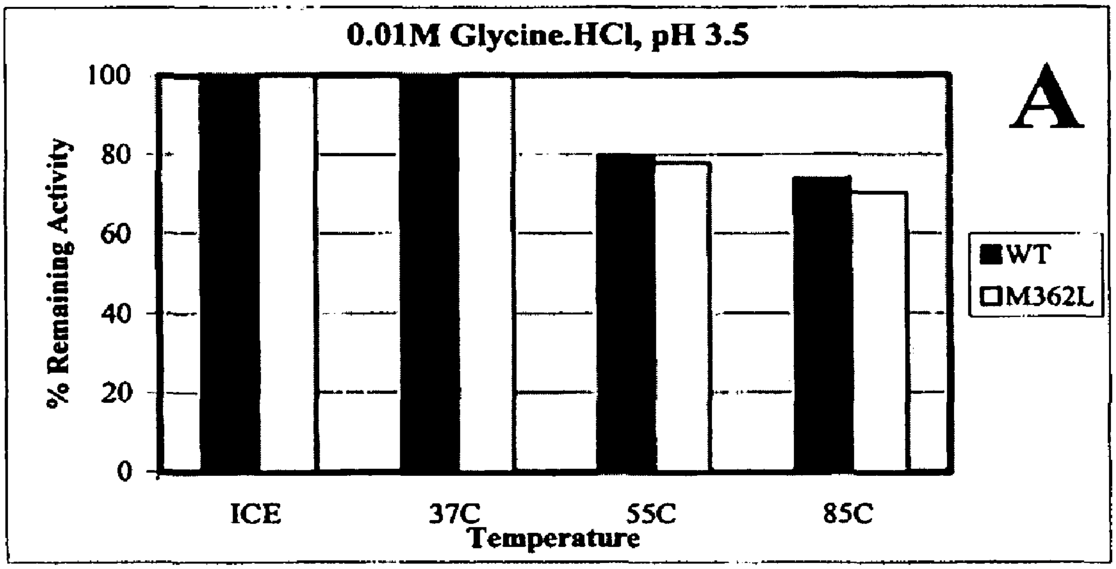
FIGS. 5A-5D are graphs showing the residual activity of *A. fumigatus* WT phytase and mutant M362L after exposure for 15 min to the indicated temperatures, in glycine.HCl (FIG. 5A=0.01 M.
Figure 5B:
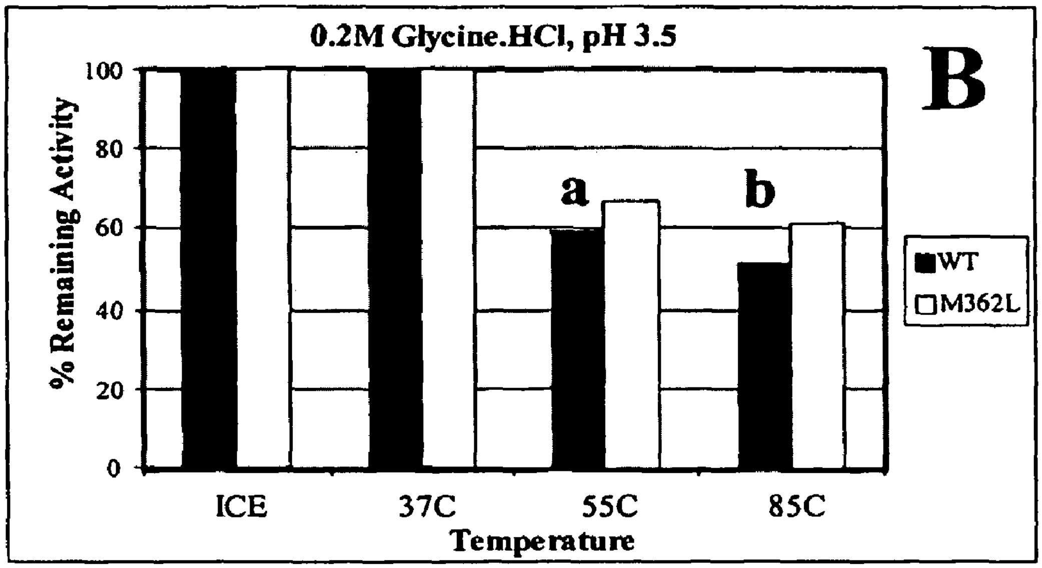
Figure 5C:
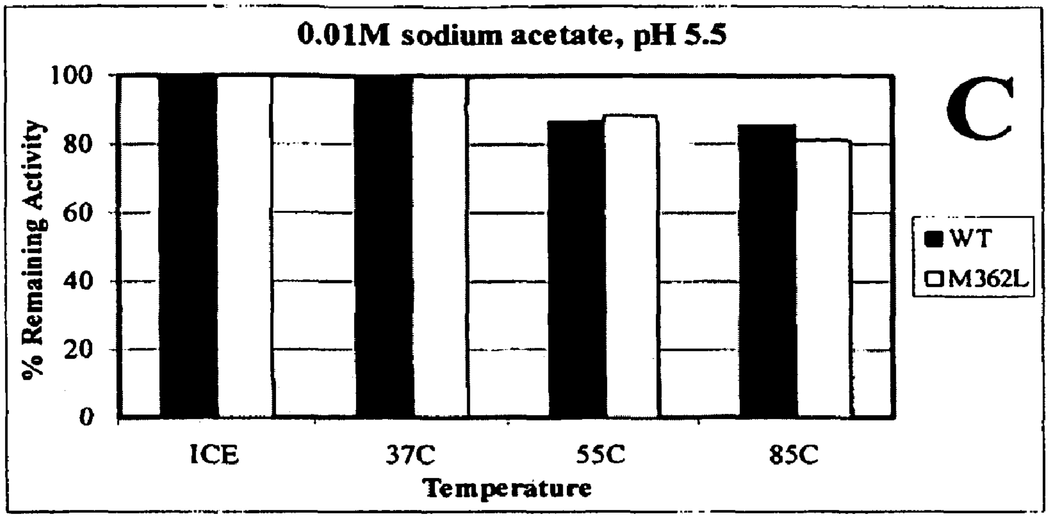
Figure 5D:
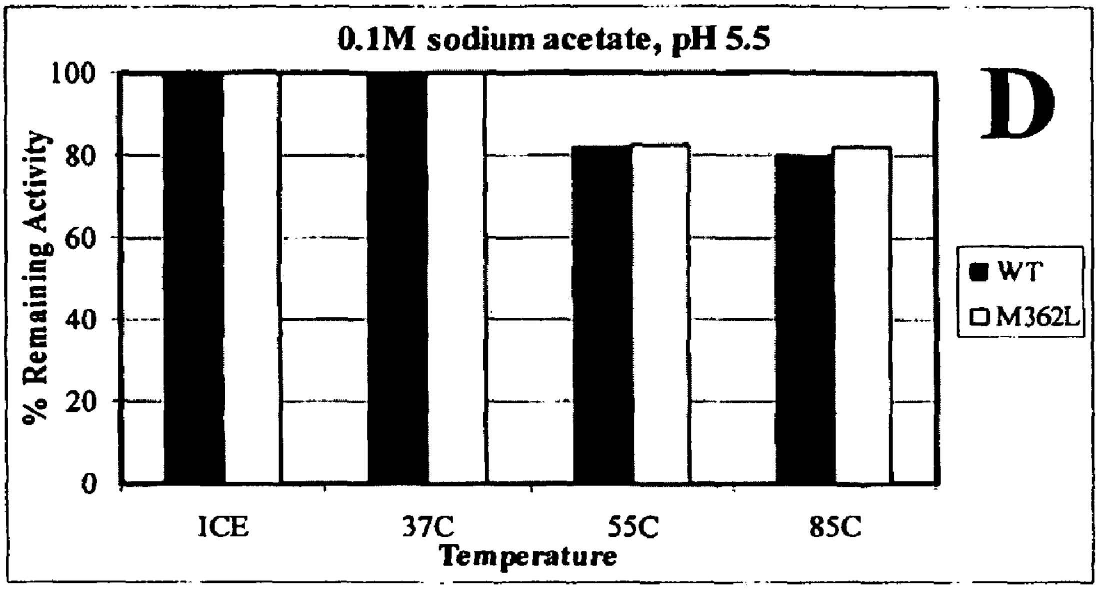

*A. fumigatus* WT phytase and mutant M362L maintained 77-88% of their initial activity after heating at 55° C. or 85° C.

in 0.01 M glycine.HCl (FIG. 5A) or sodium acetate buffer (0.01 M or 0.1 M) (FIGS. 5C and 5D). Thermotolerance of the two enzymes in 0.2 M glycine.HCl buffer was significantly reduced at either 55° C. or 85° C. A 10% difference ($P<0.05$) was observed between the WT and M362L at 85° C. in 0.2 M glycine.HCl, pH 3.5 (FIG. 5B).

Example 13

Analysis of Site-Directed Mutatgenesis of *Aspergillus* Phytases

Based on the three dimensional structural model of *A. niger* NRRL 3135 (Kostrewa et al., "Crystal Structure of Phytase from *Aspergillus ficuum* at 2.5 Å Resolution," *Nat. Struct. Biol.* 4:185-190 (1997), which is hereby incorporated by reference in its entirety), Tomschy et al. identified 43 AA residues whose side chain is exposed to the active site cavity (Tomschy et al., "Optimization of the Catalytic Properties of *Aspergillus fumigatus* Phytase Based on the Three-Dimensional Structure," *Protein Science* 9:1304-1311 (2000), which is hereby incorporated by reference in its entirety). Nineteen of these residues are identical in *A. niger* NRRL 3135, *A. fumigatus* ATTC 13073, and *A. terreus* CBS 116.46. Residue 27 is one of the 24 non-conserved amino acids ("AAs"). Changing this residue to L in *A. fumigatus* ATTC 13073 phytase significantly enhanced its catalytic property (Tomschy et al., "Optimization of the Catalytic Properties of *Aspergillus fumigatus* Phytase Based on the Three-Dimensional Structure," *Protein Science* 9:1304-1311 (2000), which is hereby incorporated by reference in its entirety). However, the identical AA substitution in *A. niger* NRRL 3135 phytase lowered its specific activity. This suggests that some unidentified interaction of one or more of the 24 non-conserved AAs with AA residue 27 is occurring in phytase. The lack of observable protein aggregation with the Q27P suggests a need for additional factors to produce this physical change.

The six amino acids comprising the *A. niger* phytase substrate specificity site (Kostrewa et al., "Crystal Structure of *Aspergillus niger* pH 2.5 Acid Phosphatase at 2.4 Å Resolution," *J. Molec. Biol.* 288:965-974 (1999), which is hereby incorporated by reference in its entirety) have an essential role in determining the ability of the phytase molecule to bind the substrate. While all six have side chains in the molecule's active cavity, only two of the six are conserved. At pH 5, the four basic and two acidic AAs of the *A. niger* PhyA substrate specificity site have a net positive charge that attracts the negatively charged phosphate group of phytate. The substrate specificity sites of *A. fumigatus* and *A. terreus* phytase contain more neutral amino acids and the attraction of the phytase and their individual catalytic rate may depend more on the hydrogen bond between AA residue 27 and the phosphate group of phytate. To further define the role of *A. niger* substrate specificity site, studies have been and/or are being conducted to determine if any of its AAs residue do significantly interact with AA residue 27.

The genetic algorithm used to examine the binding of *A. fumigatus* phytase to phytic acid indicated higher instability of the enzyme-substrate complex if M present in position 362 of the WT phytase was substituted for L. That mutation was made to improve the rate of product release from the active site of the enzyme and increase its specific activity without decreasing the heat tolerance properties. There was a 25% increase in specific activity of mutant M362L, but the increment was not as significant as initially expected based on the calculations done by the docking program and the presence of L at the same position in *A. terreus* phytase (Tomschy et al., "Optimization of the Catalytic Properties of *Aspergillus fumigatus* Phytase Based on the Three-Dimensional Structure," *Protein Science* 9:1304-1311 (2000), which is hereby incorporated by reference in its entirety). Given that M362 is not one of the AAs whose side chain is exposed to the active site cavity of the phytase, a dramatic change in pH profile of the enzyme would not be expected.

Protein glycosylation is a common feature of most yeast expression systems (Cereghino et al., "Heterologous Protein Expression in the Methylotrophic Yeast *Pichia pastoris,*" *FEMS Microbiol. Rev.* 24:45-66 (2000); and Schuster et al., "Protein Expression in Yeast; Comparison of Two Expression Strategies Regarding Protein Maturation," *J. Biotechnol.* 84:237-248 (2000), which are hereby incorporated by reference in their entirety). Mutation M362L has decreased the level of glycosylation imposed by the host *P. pastoris* when compared to *A. fumigatus* WT phytase (FIG. 3). Since the mutation is not directly affecting any potential glycosylation site of the phytase, a change in protein conformation caused by the amino acid substitution is the most probable reason for this reduced glycosylation (Trimble et al., "GlycoProtein Biosynthesis in Yeast. Protein Conformation Affects Processing of High Mannose Oligo saccharides on Carboxypeptidase Y and Invertase," *J. Biol. Chem.* 258:2562-2567 (1983), which is hereby incorporated by reference in its entirety).

In general, the different mutations described in Examples 1-13 have had a marginal effect on thermotolerance. However, specificity of the buffer has modulated to a great extent the different responses to heat denaturation observed in either *A. niger* or *A. fumigatus* phytase. All this variability in the data suggest the importance of defining very clearly the conditions used in each particular thermotolerance experiment and required caution when comparing the different values for thermotolerance of any particular phytase reported in the literature.

Example 14

Site-Directed Mutagenesis of *Aspergillus niger* NRRL 3135 Phytase at Residue 300 to Enhance Catalysis at pH 4.0.

Molecular modeling data, sequence comparison data among other fungal phytases, and site-directed mutagenesis were employed to develop a recombinant phytase with a higher activity for phytate at pH levels between 4.0 and 5.0 at 37° C. The substitution of a single amino acid, Glutamic acid (E) for Lysine (K) at residue 300, produced this desired change. This is the first reported enhancement of the catalytic activity at pH 4 of this widely used phytase at the physiologically important temperature of 37° C.

Increased phytase activity for *Aspergillus niger* NRRL 3135 phytaseA (phyA) at intermediate pH levels (3.0-5.0) was achieved by site-directed mutagenesis of its gene at amino acid residue 300. A single mutation, K300E, resulted in an increase of the hydrolysis of phytic acid of 56% and 19% at pH 4.0 and pH 5.0, respectively, at 37° C. This amino acid residue has previously been identified as part of the substrate specificity site for phyA and a comparison of the amino acid sequences of other cloned fungal phytases indicated a correlation between a charged residue at this position and high specific activity for phytic acid hydrolysis. The substitution at this residue by either another basic (e.g., R=arginine), uncharged (e.g., T=threonine), or acidic (e.g, D=aspartic acid) amino acid did not yield a recombinant enzyme with the same favorable properties. Therefore, it was concluded that this residue is not only important for the catalytic function of phyA, but also essential for imparting a favorable pH environment for catalysis.

Example 15

Phytase Mutations

Plasmid pYPP1, containing the *A. niger* NRRL 3135 phyA gene, cloned into a *Saccharomyces cerevisiae* expression vector pYES2 was employed to generate the mutations (Han et al., "Expression of an *Aspergillus niger* Phytase Gene (phyA) in *Saccharomyces cerevisiae," Appl. Environ. Microbiol.* 65:1915-1918 (1999), which is hereby incorporated by reference in its entirety). The following oligonucleotides were synthesized to generate site specific mutations at K300 residue: K300E mutation 5'CTC CAG TCC TTG GAA AAG TAT TACG 3' (SEQ ID NO:62), K300D mutation 5'CTC CAG TCC TTG GATAAG TAT TAC GGC 3' (SEQ ID NO:63), K300R 5'CTC CAG TCC TTG AGA AAG TAT TAC GGC 3' (SEQ ID NO:64), and K300T was 5'CTC CAG TCC TTG ACA AAG TAT TAC GGC3' (SEQ ID NO:65). The oligonucleotides were phosphorylated and the Gene Editor™ in vitro Site-Directed Mutageneis System (Promega, Madison, Wis.) was used to generate the desired mutations. The annealing temperature for K300E and K300D was 75° C. for 5 minutes, and for K300R and K300T it was 80° C. for 5 minutes. The reactions were allowed to cool at 1.5° C. per minute until 37° C. was reached. DNA sequencing then confirmed the presence of the desired mutation in the selected transformants. The transformation procedure was previously described in Han et al., "Expression of an *Aspergillus niger* Phytase Gene (phyA) in *Saccharomyces cerevisiae," Appl Environ. Microbiol.* 65:1915-1918 (1999), which is hereby incorporated by reference in its entirety.

Example 16

Transformation and Protein Expression

*Saccharomyces cerevisiae* INVSc1 (Invitrogen) were grown in yeast extract-peptone-dextrose medium (YPD) and prepared for transformation according to the manufacturer instructions (Invitrogen, Catalog no. V825-20). Plasmid DNA containing phyA mutant genes was transformed into *Saccharomyces* by the electroporation (1.5 kV, 129Ω, 4.9 msec. ECM 600 Electro Cell Manipulator, Genetronics, BTX Instrument Division, San Diego, Calif.). After incubation for 2 hours at 30° C. in 1 M sorbitol without agitation, cells were plated in uracil deficient (URA(−)) selective agar to screen for positive transformants. Isolated positive colonies were initially grown in URA (−) broth at 30° C. for 48 hours and prepared for glycerol stock culture. An aliquot of URA (−) culture was inoculated into YPD broth and grown for 36 to 48 hours for cell enrichment, and then centrifuged at 1,500 rpm, 25° C. for 10 min. The cell pellet was suspended in YPG medium (1% Yeast extract, 2% peptone, 2% galactose) for induction of the recombinant enzyme expression. Phytase activity of the culture medium was measured after 36 to 48 hours.

Example 17

Purification of Phytase

About 90 ml of crude culture filtrate containing the phytase expressed in yeast was dialyzed against 25 mM sodium acetate, pH 3.75. The dialyzed protein was first loaded onto a 5.0 ml MacroPrep S column equilibrated in the acetate buffer. The column was run at 3.0 ml per min at room temperature using the Econo-Column System (Bio-Rad) which was programmed to run a liner sodium chloride gradient (0 to 0.3M) in acetate buffer over 15 min. The column was then flushed with 15 ml portions each of 0.5M and 1.0M sodium chloride solution in acetate buffer to strip tightly bound proteins from the column. The active phytase came in the salt gradient in several fractions, which were pooled. The second column was also a cationic exchanger (MacroPrep S) but the column volume was only 1 ml. The active protein from step one was diluted 1:3 with acetate buffer and then loaded onto this column. After loading and washing the column with acetate buffer, a salt gradient (0-0.3 M NaCl) was run at a flow rate of 3.0 ml per min. The active phytase was eluted as a single peak in the salt gradient, which was dialyzed against 25 mM imidazole, pH 7.0. The dialyzed protein was loaded onto a MacroPrep Q anion exchanger (1.0 ml column). The bound protein was eluted as a sharp peak using a 0 to 0.3M NaCl gradient at a flow rate of 3.0 ml per min.

Example 18

Purity and Homogeneity of Phytase

All five phytases, the unmodified control and all four mutants, were checked for purity after purification by SDS-PAGE. A diffused single protein band was discerned at about 200-kDa. This is due to higher glycosylation of the phytase molecule that had taken place in a yeast expression system (Han et al., "Expression of an *Aspergillus niger* Phytase Gene (phyA) in *Saccharomyces cerevisiae," Appl. Environ. Microbiol.* 65:1915-1918 (1999), which is hereby incorporated by reference in its entirety). Nonetheless, the expressed phytase was purified to near homogeneity by sequential chromatographies as mentioned above.

Example 19

Phytase Assay

Assays were performed in 1.0 mL volumes at designated temperatures in the appropriate buffer. The buffer used for pH 1.0-2.5 was 50 mM glycine HCl; pH 3.0-5.0 was 50 mM sodium acetate; and pH 6.0-9.0 was 50 mM imidazole. The liberated inorganic ortho phosphates were quantitated spectrophotometrically by a modified method from Heinonen et al., "A New and Convenient Colorimetric Determination of Inorganic Orthophosphate and its Application to the Assay of Inorganic Pyrophosphatase," *Analytical Biochemistry* 113: 313-317 (1981), which is hereby incorporated by reference in its entirety, using a freshly prepared acidified acetone and ammonium molybdate (AMA) reagent consisting of acetone, 10 mM ammonium molybdate, and 5.0 N sulfuric acid, (2:1:1, v/v/v). Adding 2.0 mL AMA solution per assay tube terminated the phytase assay. After 30 seconds, 0.1 mL of 1.0 M citric acid was added to each tube. Absorbance was read at 355 nm after zeroing the spectrophotometer with an appropriate control. A standard curve for inorganic ortho phosphate was made within the range of 10 to 500 nmoles. Activity was expressed in Kat (moles of substrate conversion per second).

Example 20

Analysis of Site-Directed Mutagenesis of *Aspergillus niger* NRRL 3135 Phytase at Residue 300 to Enhance Catalysis at pH 4.0

Figure 6:
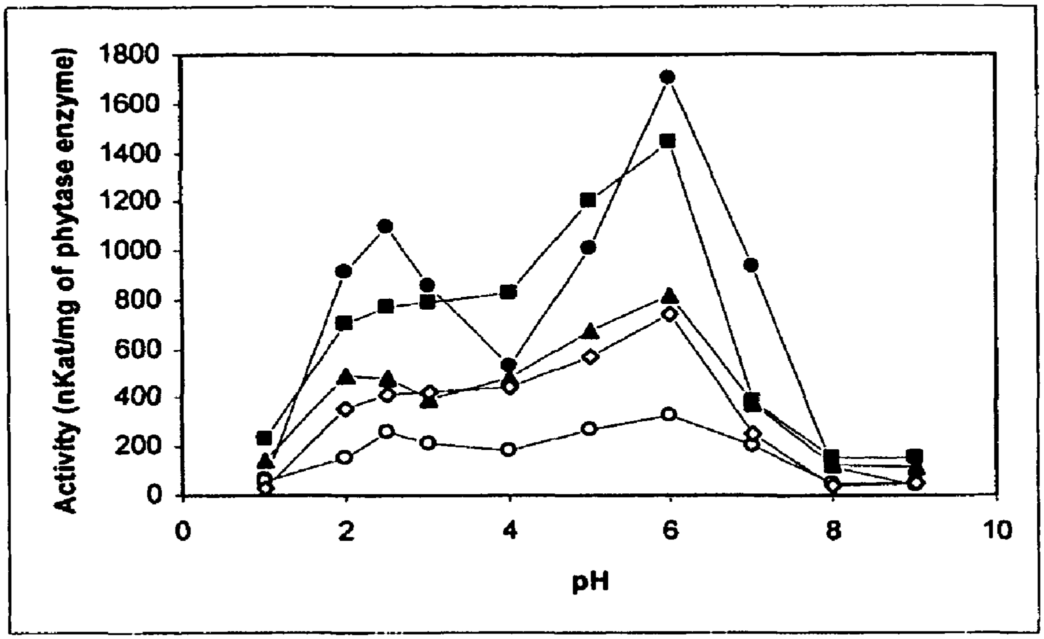
FIG. 6 is a graph showing the pH activity profiles of *A. niger* NRRL phyA (●), and the single mutants K300E (■), K300D (▲), K300R(○) and K300T (◇).

Site-directed mutagenesis in the NRRL 3135 phyA gene at the DNA sequence encoding residue 300 was performed. K was replaced by similarly charged R, oppositely charged D and E, and uncharged but polar T. All four mutants proteins were purified to near homogeneity and then each was characterized for its activity as a function of pH. The results are shown in FIG. 6. The pH profile of all four mutants (K300E, K300D, K300R and K300T) were altered from the unique bi-hump pH optima profile characteristic of native NRRL 3135 phyA (FIG. 6). Of all four mutants tested at 37° C., one mutation, K300E, imparted increased specific activity for the substrate phytic acid at pH 4.0 and 5.0. In this mutation, the basic amino acid lysine (K) was replaced by an acidic residue amino acid, glutamic acid (E). Replacement of this K residue with another acidic residue, aspartic acid (D), or an uncharged but polar amino acid, threonine (T), did not significantly alter activity at pH 4. Replacement with the acidic residue arginine (R) lowered activity over the pH range 2.0 to 6.0. It is noteworthy that the native NRRL 3135 phyA has slightly higher activity at pH 6.0 than the mutant K300E.

Unlike other known enzymes, NRRL 3135 phyA phytase shows a characteristic bi-hump two pH optima profile (Ullah et al., "Extracellular Phytase (E. C. 3.1.3.8) from *Aspergillus* ficuum NRRL 3135: Purification and Characterization," *Prep. Boichem.* 17:63-91 (1987), which is hereby incorporated by reference in its entirety). The reason for this is the dip in activity around pH 3.5 to 4.0. To assess the effect on relative activity of mutations at 300 residue at pH 6.0 where it is maximal, and pH 4.0, where there is a noticeable dip for wild type NRRL 3135 phytase, activity was measured at 37° C. Table 3 shows the results. As expected, the native enzyme gave the highest ratio. Among the four mutants only K300E maintained a high specific activity. The specific activity was lowered substantially for the three other mutants, K300D, K300R, and K300T (Table 3). The results point out the importance of residue 300 in both catalytic rate determination and pH optima. The substitution of E for K at residue 300 has resulted in the lowering of the ratio without affecting the catalytic function of the mutant protein.

TABLE 3

The Ratio of Enzyme Activity at pH 6.0 Over pH 4.0 for Native *A. niger* NRRL 3135 phyA and Mutant Proteins.

| Protein | Ratio of activity at pH 6.0/4.0 at 37° C. |
|---|---|
| *A. niger* NRRL 3135 phytase | 3.29 |
| *A. niger* NRRL 3135 K300E | 1.74 |
| *A. niger* NRRL 3135 K300D | 1.71 |
| *A. niger* NRRL 3135 K300R | 1.81 |
| *A. niger* NRRL 3135 K300T | 1.68 |

The experiments and data described in Examples 14-20 demonstrate the influence amino acid residue 300 has on the catalytic properties of *A. niger* NRRL 3135 phyA. Mutant K300E displays higher specific phytase activity at the intermediate pH range (4.0 to 5.0) than the native NRRL 3135 phytase at 37° C. Since phytase is now widely used as an animal feed additive, enhanced activity at this temperature is extremely desirable. The reduced specific activity of K300E for phytic acid at pH 2.0-3.0 and also at pH 6.0-7.0 also supports the model advanced for the substrate specificity site in phyA (Kostrewa et al., "Crystal Structure of *Aspergillus niger* pH 2.5 Acid Phosphatase at 2.4 Å Resolution," *J. Mol. Biol.* 288:965-974 (1999), which is hereby incorporated by reference in its entirety). That model predicts that the substitution of an acidic amino acid for the basic residue K300 would lower the local electrostatic field attraction for phytic acid at both these pH ranges.

Amino acid residues K300 and K301 are both components of the substrate specific site in *A. niger* NRRL 3135 phyA (Kostrewa et al., "Crystal Structure of *Aspergillus niger* pH 2.5 Acid Phosphatase at 2.4 Å Resolution," *J. Mol. Biol.* 288:965-974 (1999), which is hereby incorporated by reference in its entirety). An analysis of the amino acid sequences in this region of other fungal phyAs discloses that while residue R301 is strongly conserved, the residues at 300 vary broadly. This variation at residue 300 is presented in Table 4. This analysis also suggests a possible correlation between the amino acid at position 300 and the native enzyme's level of phytase activity. Wyss et al., "Biochemical Characterization of Fungal Phytases (Myo-inositol Hexakisphosphate Phosphohydrolases): Catalytic Properties," *Applied and Envir. Micro.* 65:367-373 (1999), which is hereby incorporated by reference in its entirety, described two classes of HAP phytases, one with a broad substrate specificity but a lower specific activity for phytate and the other class with a narrow substrate specificity but a high specific activity with phytic acid. The former class includes phytases from *A. fumigatus, A. nidulans*, and *M. thermophila* and the latter include *A. niger* NRRL 3135, *A. terreus* 9 µl, and *A. terreus* CBS. A neutral amino acid occupies the residue corresponding to K300 in *A. niger* NRRL 3135 phyA in all the phytases with low specific activity for phytate. However, the phytases with high specific phytase activity have either a basic or acidic amino acid at this position.

TABLE 4

Comparison of *A. niger* NRRL 3135 PhyA Residues 300 and 301 with the Analogous Residues in Other Fungal PhyAs Having Different Levels of Specific Activity for Phytic Acid as a Substrate.

| | Residue Number | | Class of Amino Acid | Specific Activity High (H) or |
|---|---|---|---|---|
| Source of Phytase | 300 | 301 | At Residue 300 | Low (L) |
| *A. niger* NRRL 3135 | K | K | Basic | H (6) |
| *A. terreus* 9A1 | D | K | Acidic | H (6) |
| *A. terreus* CBS 116.46 | D | K | Acidic | H (6) |
| *P. lycii* CBS 686.96 | D | K | Acidic | H (18) |
| *A. fumigatus* ATCC 13073 | G | K | Neutral | L (6) |
| *A. nidulans Roche* Nr. R1288 | S | K | Neutral | L (6) |
| *M. thermophila* ATCC 48102 | G | K | Neutral | L (6) |
| *T. thermophilus* ATCC 20186 | G | K | Neutral | — |
| Consensus-1 Phytase | G | K | Neutral | L (8) |

Recent research has established that the level of specific activity of the phyA phytase molecule is the result of numerous interactions between the many amino acids comprising its catalytic center, substrate specificity site and other structures (Tomschy et al., "Optimization of the Catalytic Properties of *Aspergillus fumigatus* Phytase Based on the Three-Dimensional Structure," *Protein Science* 9:1304-1311 (2000); Tomschy et al., "Active Site Residue 297 of *Aspergillus niger* Phytase Critically Affects the Catalytic Properties,"

*FEBS* 472:169-172 (2000); and Lehmann et al., "Exchanging the Active Site Between Phytases for Altering the Functional Properties of the Enzyme," *Protein Science* 9:1866-1872 (2000), which are hereby incorporated by reference in their entirety). The importance of these interactions is supported by the pH activity profile of other mutants described in herein. Enhanced specific activity over wild type at pH 4.0 was not evident in either the K300D or K300T (FIG. 6). The profiles of K300D and K300T were similar and indicate that the increase in specific activity in K300E was not caused merely by the substitution of an acidic amino acid. The results point to a relationship between the increased specific activity and the longer side chain of glutamic acid. The similarity of the specific activity of K300D and K300T over the pH range 2.0 to 6.0 also hints at the importance of the side chain in K300E. The low specific activity of K300R over this same range also supports the negative effect of R at residue 297 cited earlier (Tomschy et al., "Active Site Residue 297 of *Aspergillus niger* Phytase Critically Affects the Catalytic Properties," *FEBS* 472:169-172 (2000), which is hereby incorporated by reference in its entirety). It has been shown that when R is substituted for an adjacent amino acid residue, 300, a similar decrease in specific activity results over a wide pH range.

In the Tomschy et al. study (Tomschy et al., "Active Site Residue 297 of *Aspergillus niger* Phytase Critically Affects the Catalytic Properties," *FEBS* 472:169-172 (2000), which is hereby incorporated by reference in its entirety), the site-directed mutation R297Q increased the specific activity of *A. niger* T213 phytase at pH 2.5 and 4.5-7.0. No enhancement of specific activity was reported in the pH 3.0-4.5 range and the need for future research was noted in order to explain the decline of catalytic activity in this range. The two optima pH profiles for NRRL 3135 phyA have been noted in previous studies (Ullah et al., "Extracellular Phytase (E. C. 3.1.3.8) from *Aspergillus ficuum* NRRL 3135: Purification and Characterization," *Prep. Boichem.* 17:63-91 (1987); Wyss et al., "Biochemical Characterization of Fungal Phytases (Myo-inositol Hexakisphosphate Phosphohydrolases): Catalytic Properties," *Applied and Envir. Micro.* 65:367-373 (1999); Lehmann et al., "Exchanging the Active Site Between Phytases for Altering the Functional Properties of the Enzyme," *Protein Science* 9:1866-1872 (2000); and Tomschy et al., "Active Site Residue 297 of *Aspergillus niger* Phytase Critically Affects the Catalytic Properties," *FEBS* 472:169-172 (2000), which are hereby incorporated by reference in their entirety). Explanations of its unique pH profile have ranged from possible buffer effect (Lehmann et al., "Exchanging the Active Site Between Phytases for Altering the Functional Properties of the Enzyme," *Protein Science* 9:1866-1872 (2000), which is hereby incorporated by reference in its entirety) to an artifact (Berka et al., "Molecular Characterization and Expression of a Phytase Gene From the Thermophilic Fungus *Thermomyces lanuginosus," Appl. Environ. Microbiol.* 64:4423-4427 (1998), which is hereby incorporated by reference in its entirety). Examples 14-20 describe the link between a structural component of the *A. niger* NRRL 3135 phyA substrate specificity site and this unique catalytic feature.

In the experiments described in Examples 14-20, three buffers were used to cover the entire range from pH 1 through 9 for the pH profile. A 50 mM imidazole buffer was used for the range pH 6 through 9. The selection of buffer is very important in this range. For example, Tris buffer at higher ionic strength (200 mM) was found to inhibit phytase essay. Therefore, the pH profile may look somewhat different depending upon what buffers were used. Using a Tris buffer in this range would have altered the pH profile for both the wild type and the mutants in the basic range.

In addition, a significant role of the amino acid corresponding to *A. niger* 300K in *A. fumigatus* ATCC 13073 phyA (277G) has been reported (Tomschy et al., "Engineering of Phytase for Improved Activity at Low pH," *Appl. Environ. Microbiol.* 68:1907-1913 (2002), which is hereby incorporated by reference in its entirety). In that study, the double mutations, G277K and Y282H, gave rise to a second pH optimum, pH 2.8-3.4, in *A. fumigatus* phytase. This *A. fumigatus* mutant phytase displayed the two optima pH profile unique to NRRL 3135 phyA.

In conclusion, both an analysis of a substrate specificity site, previously identified from 3D structure studies of *A. niger* NRRL 3135 phyA, together with amino acid sequences from other fungal phytases were utilized to identify a single residue for site-directed mutations. This has resulted in one mutant K300E with enhanced specific activity for phytic acid in the pH range 3.5-5.0 at the physiologically important temperature of 37° C. While phytase from *A. niger* NRRL 3135 is extensively utilized as an animal feed additive, this is the first reported enhancement of a catalytic feature for this *A. niger* enzyme. Information from these mutations has validated the important role of this amino acid residue in the substrate specificity site of this enzyme and also advanced the understanding of the actual relationship between a specific phyA component and a characteristic feature. Based on these results, further research on the substrate specificity site has the potential to improve the catalytic effectiveness of *A. niger* NRRL 3135 phyA as a feed additive to lower phosphorus levels in animal manure.

Example 21

Improving *Aspergillus niger* PhyA Phytase by Protein Engineering

Figure 7B:
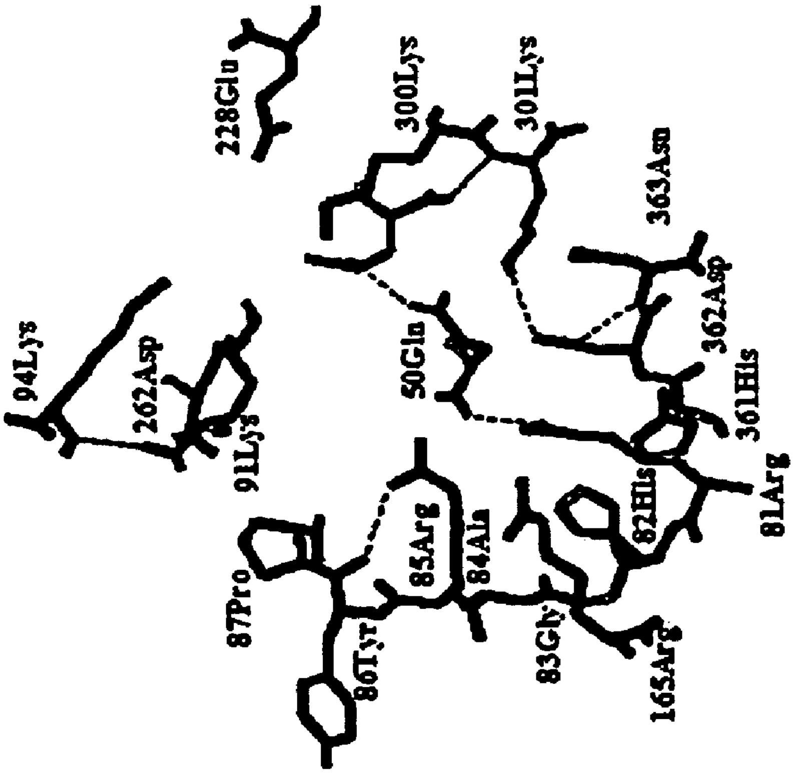
FIGS. 7A-7B are diagrams showing the crystal structure of *A. niger* phytase (phyA) (FIG. 7A) and its active site (FIG. 7B) containing RHX motif, HD motif and amino acid residues involved in substrate binding (Kostrewa et al., "Crystal Structure of *Aspergillus niger* pH 2.5 Acid Phosphatase at 2.4 Å Resolution," *J. Mol. Biol.* 288:965-974 (1999)).
Figure 7A:
Figure 8A:
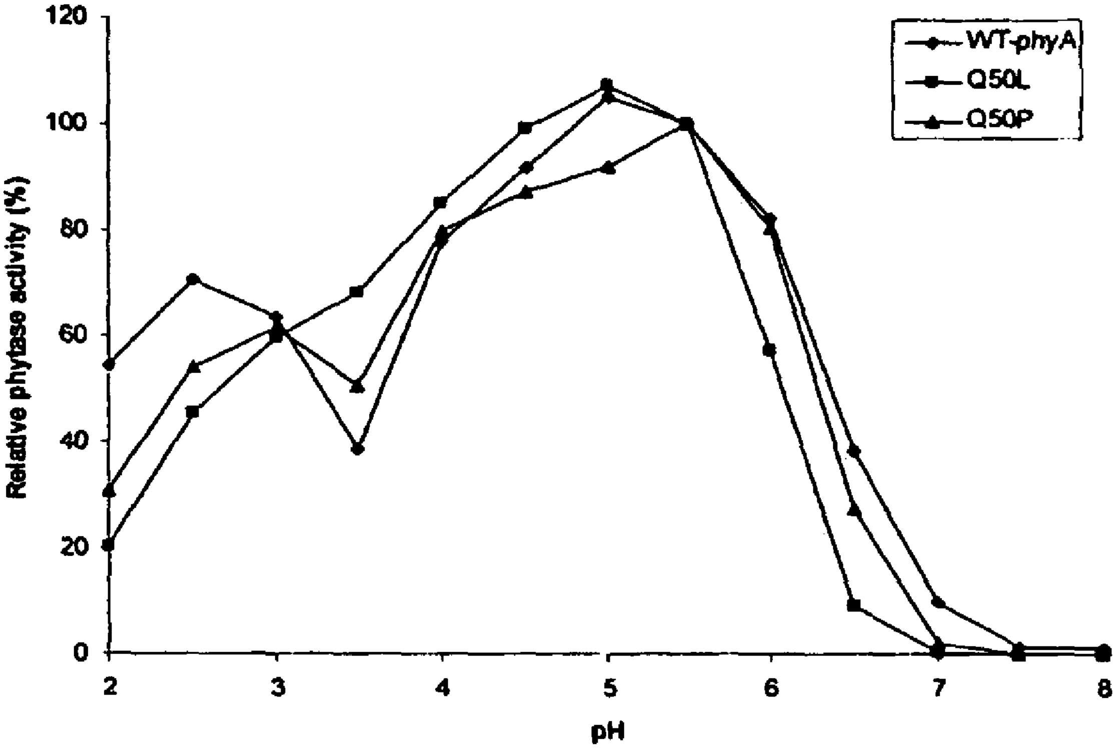
FIGS. 8A-8G are graphs showing the pH profiles of PhyA mutants. Amino acids in the substrate binding site were replaced with other amino acid residues with different polarity and charges.
Figure 8B:
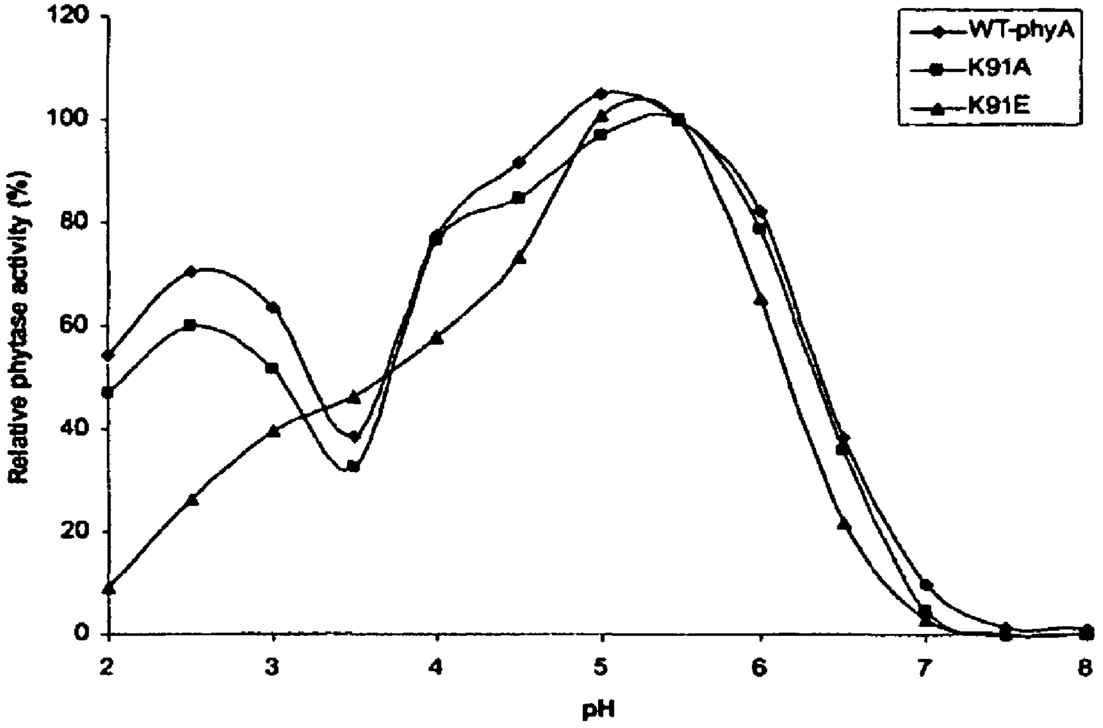
Figure 8C:
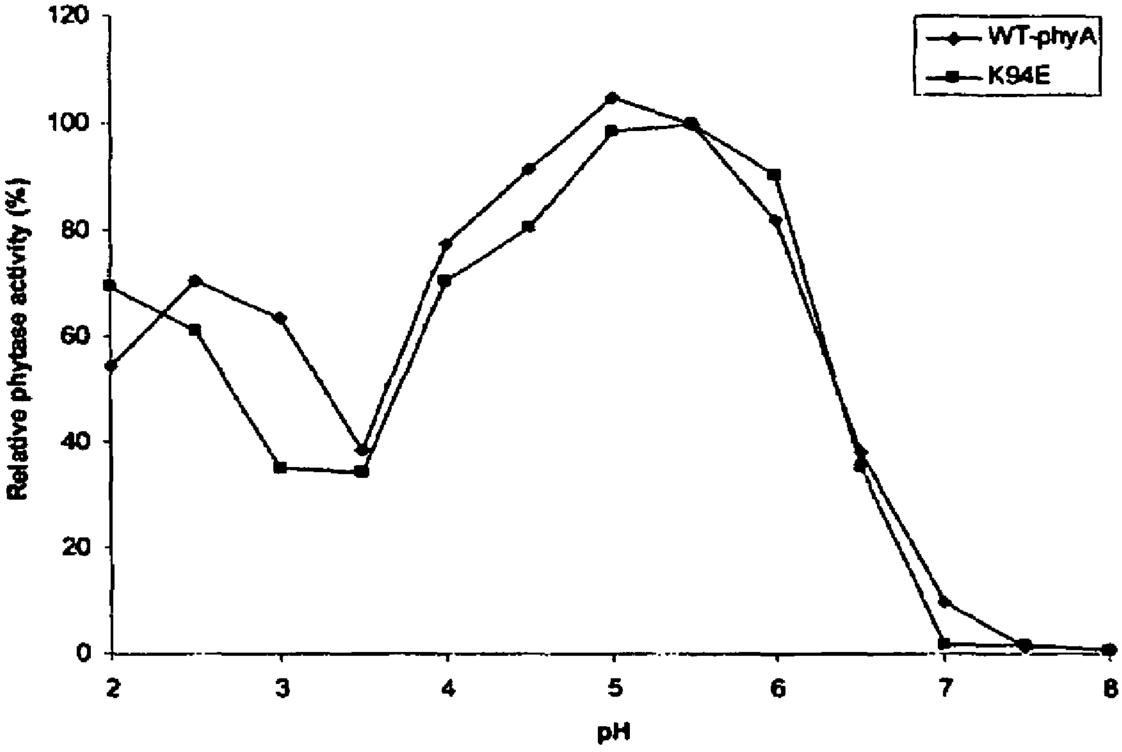
Figure 8D:
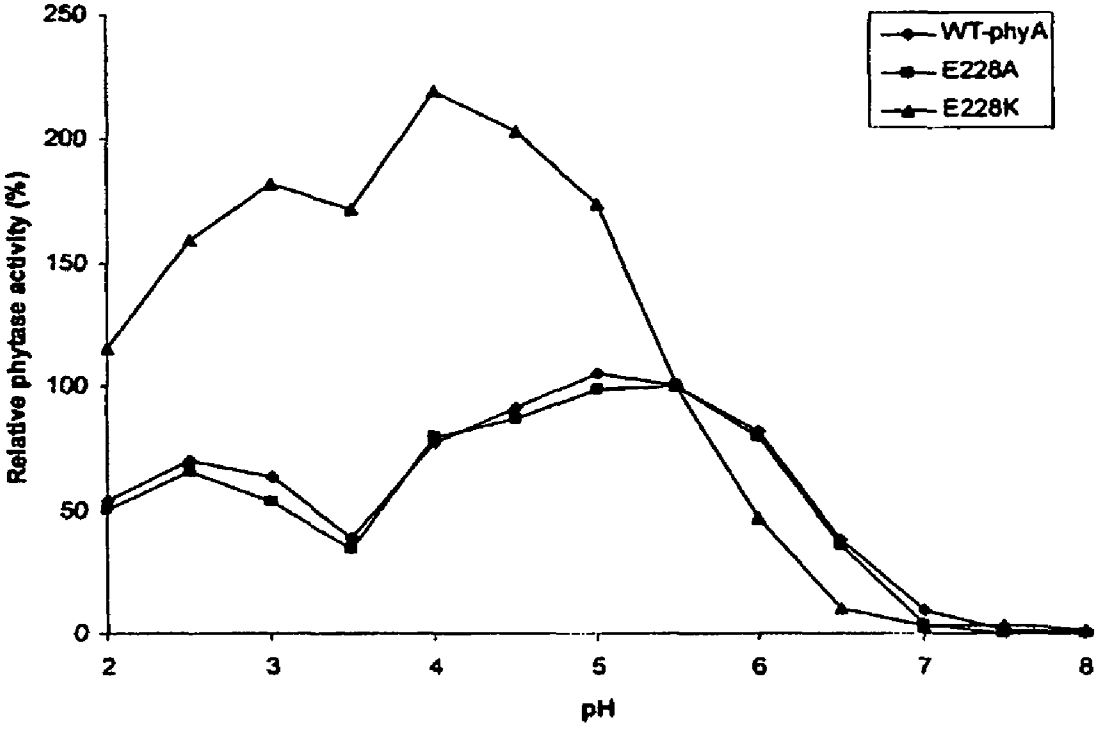
Figure 8E:
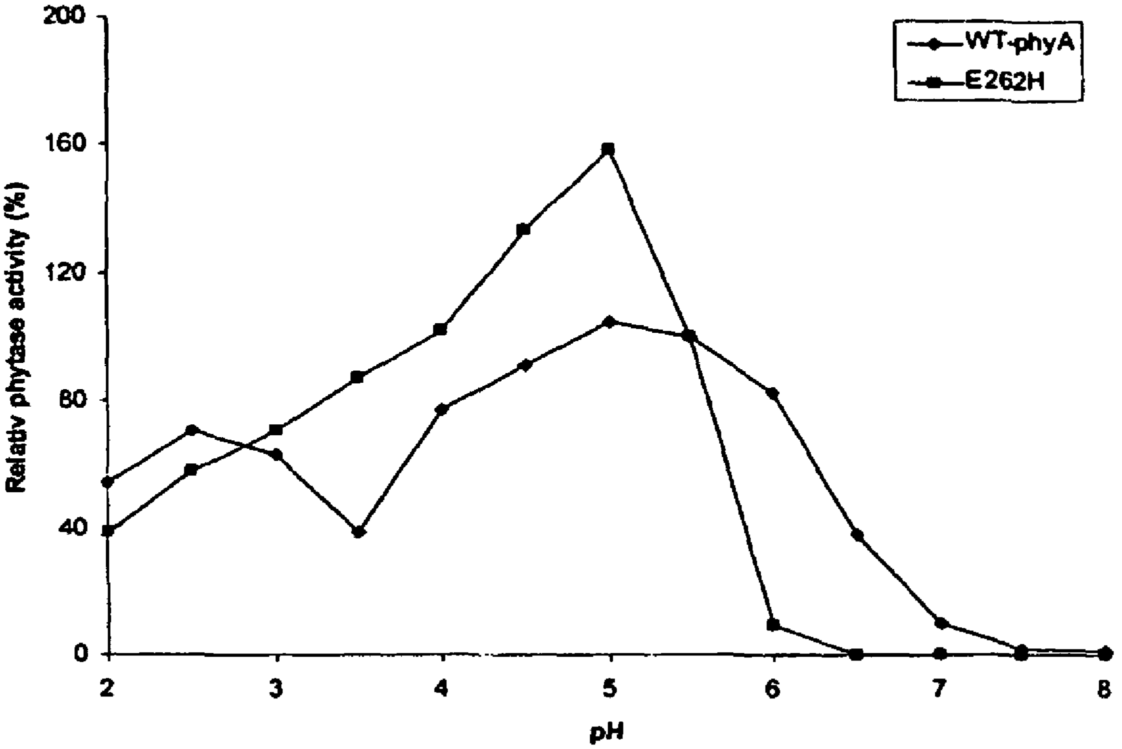
Figure 8F:
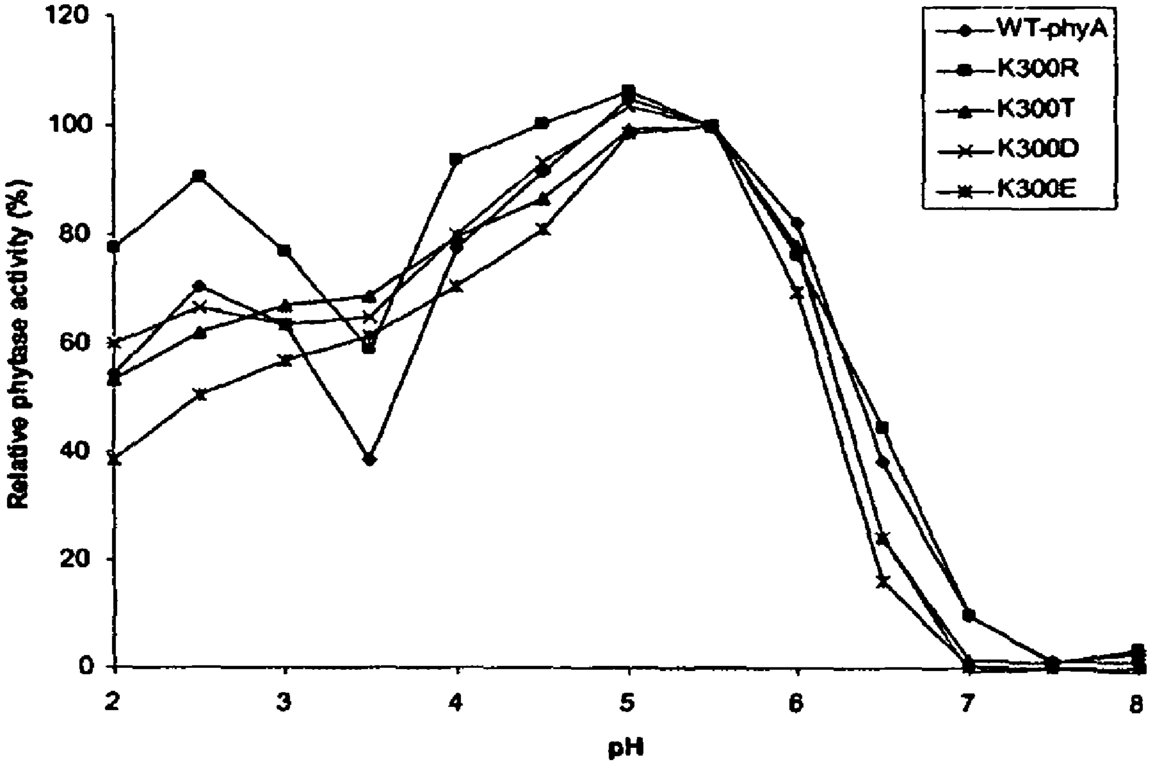
Figure 8G:
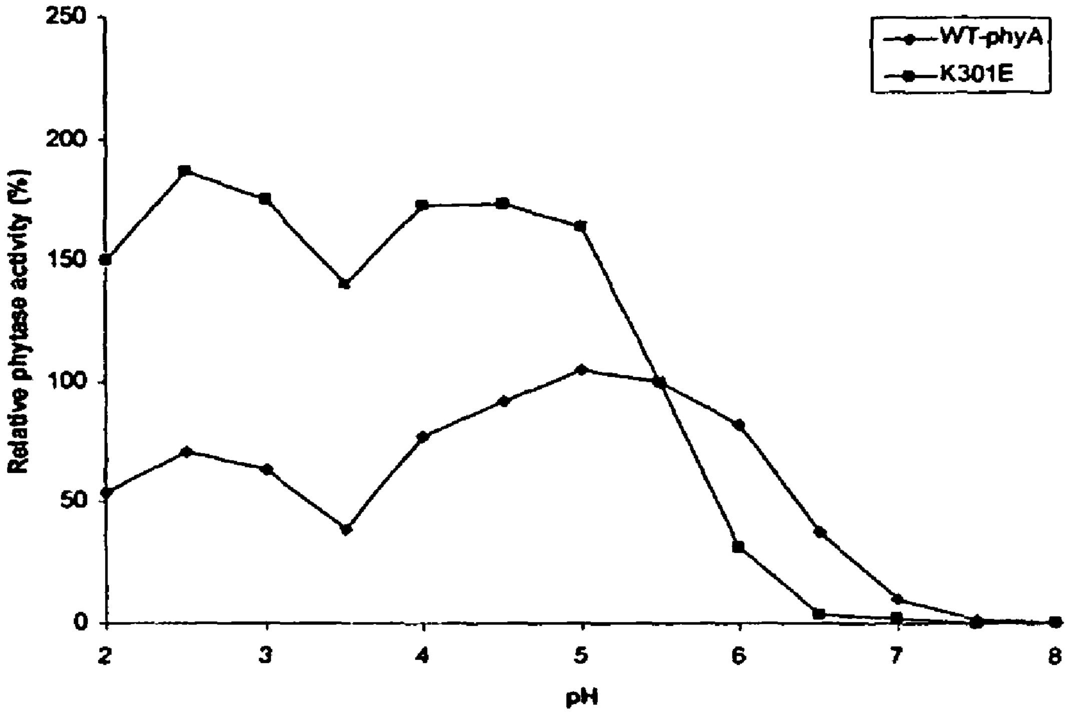

Based on the PhyA molecular modeling (Kostrewa et al., "Crystal Structure of *Aspergillus niger* pH 2.5 Acid Phosphatase at 2.4 Å Resolution," *J. Mol. Biol.* 288:965-974 (1999), which is hereby incorporated by reference in its entirety) (see FIG. 7) and the sequence comparisons among other fungal phytases, it appears that the reason for poor activity of PhyA at pH 3.5 is due to the $pK_a$ of acid/base catalytic residues and the charge environment in the active site. Because amino acid residues K91, K94, E228, D262, K300, and K301 are involved in the substrate binding (Kostrewa et al., "Crystal Structure of *Aspergillus niger* pH 2.5 Acid Phosphatase at 2.4 Å Resolution," *J. Mol. Biol.* 288:965-974 (1999), which is hereby incorporated by reference in its entirety), experiments were performed to substitute them individually or in combination with different amino acids. Some of the objectives of these experiments were to: (1) to improve the pH profile of PhyA for its function under the stomach conditions; (2) to understand the structure impact of each specific amino acid on the PhyA pH profile; (3) to determine the effects of these amino acids on the PhyA hydrolysis efficiency of phytate from sodium phytate and plant source (soybean meal); and (4) to determine the impact of these amino acids on the molecular size, glycosylation, and thermostability.

Example 22

Construction of phyA Mutants

Plasmid pYPP1, containing the *A. niger* NRRL3135 phyA gene cloned into the *Saccharomyces cerevisiae* expression vector pYES2 (Han et al., "Expression of an *Aspergillus niger* Phytase Gene (phyA) in *Saccharomyces cerevisiae*," *Appl. Environ. Microbiol.* 65:1915-1918 (1999), which is hereby incorporated by reference in its entirety), was employed to generate the mutations. Oligonucleotides were synthesized to generate site specific mutations at substrate binding sites described in Table 5. The phyA mutants in pYPP1 were constructed using the Gene Editor in vitro Site-Directed Mutagenesis System according to Mullaney et al., "Site-Directed Mutagenesis of *Aspergillus niger* NRRL 3135 Phytase at Residue 300 to Enhance Catalysis at pH 4.0.," *Biochem. Biophys. Res. Commun.* 277:1016-1020 (2002), which is hereby incorporated by reference in its entirety. The coding region of the pYPP1 mutant construct was amplified by PCR using two primers (upstream, 5'CGG AAT TCC TGG CAG TCC CCG3' (SEQ ID NO:66); downstream, 5'GCT CTA GAC TAA GCA AAA CAC TCC3' (SEQ ID NO:67)) and inserted into a constitutive expressing vector pGAPZαA (Invitrogen, San Diego, Calif.) at EcoRI and XbaI sites. The gene was led by a signal peptide α-factor and was under the control of GAP promoter. The DNA sequence of each inserted phyA variants was confirmed the presence of the desired mutations in the selected transformants.

Example 23

Transformation and Protein Expression

The pGAP vector containing phyA mutant gene (10 μg) was linearized by restriction enzyme BamHI and transformed into *Pichia pastoris* X33 by electroporation using ECM 600 Electro Cell Manipulator (Gentronics, Inc., BTX Instrument Division, San Diego, Calif.). The transformed cells were plated in YPD agar (1% yeast extract, 2% peptone, and 2% dextrose) plus zeocin (100 μg/ml) and incubated at 30° C. for 3 days. Single colonies of the transformants were selected, inoculated into YPD media, and incubated at 30° C. for 2 days for phytase expression. Phytase activity of the culture supernatant was measured to screen for high phytase activity-producing transformants.

Example 24

Enzyme Purification

The expressed PhyA and mutant enzymes in the medium supernatant were concentrated by ultrafiltration (Amicon Stirred Ultrafiltration Cells. Millipore Corp, Bedford, Mass.) with a membrane having an apparent molecular cutoff of 30,000. The concentrated phytase solution was loaded onto a DEAE-cellulose column (Sigma, St Louis, Mo.) equilibrated with 10 mM Tris-HCl, pH 7.4. The bound protein was eluted using a linear gradient from 0-0.3 M NaCl in 10 mM Tris-HCl, pH 7.4 at a flow rate of 0.2 ml per minute. Three fractions exhibiting the highest activities were pooled and concentrated by spin column concentration unit. The concentrated phytase was loaded onto Sephadex G-100 gel exclusion column chromatography equilibrated with 50 mM Tris-HCl buffer containing 0.15M NaCl, pH 7.4. The phytase protein was eluted as a single peak and used for further analysis.

Example 25

Phytase Activity and Protein Assay

Phytase activity was measured using sodium phytate as the substrate. One phytase unit (U) was defined as the amount of activity that releases 1 μmol of inorganic phosphorus from sodium phytate per minute at pH 5.5 and 37° C. The enzyme was diluted in 0.2 M citrate buffer, pH 5.5 (or the buffer and pH as indicated in the results), and an equal volume of substrate solution containing 11 mM sodium phytate (Sigma) was added. After incubation of the sample for 15 min at 37° C., the reaction was stopped by addition of an equal volume of 15% trichloroacetic acid. The release inorganic phosphorus was determined as previously described (Rodriguez et al., "Site-Directed Mutagenesis Improves Catalytic Efficiency and Thermostability of *Escherichia coli* pH 2.5 Acid Phosphatase/Phytase Expressed in *Pichia pastoris*," *Arch. Biochem. Biophys.* 382:105-112 (2000), which is hereby incorporated by reference in its entirety). The total protein concentration in the samples was determined by the method of Lowry et al., "Protein Measurement With the Folin Phenol Reagent," *J. Biol. Chem.* 193:265-275 (1951), which is hereby incorporated by reference in its entirety.

Example 26 pH Profile

The pH profiles of the expressed phytases were determined using the following buffers: 0.2M glycine-HCl for pH 2-3.5; 0.2M citrate for pH 4-6.5; 0.2M Tris.HCl for pH 7-8.5. The substrate was 1% sodium phytase dissolved in each of the selected buffers. Purified enzymes were diluted in nanopure water to give an activity of 0.1 U/ml.

Example 27

SDS-PAGE and Western Blotting

Samples of purified protein were subjected to 10% SDS-PAGE using a Mini-ProteinII Cell (Bio-Rad Laboratories, Hercules, Calif.) (Laemmli, "Cleavage of Structural Proteins During the Assembly of the Head of Bacteriophage T4," *Nature* 227:680-685 (1970), which is hereby incorporated by reference in its entirety). Protein was stained with Coomassie Brilliant Blue R-250 and quantified by an IS-1000 digital imaging system (Alpha Innotech Co., San Leandro, Calif.). The molecular weight marker used was prestained SDS-PAGE standard (Broad range, Bio-Rad). For Western blot analysis, the separated proteins were transferred onto a Protran nitrocellulose membrane (Schleicher & Schuell, Keene, N.H.) with a Mini Trans-Blot cell (Bio-Rad). A rabbit polyclonal immunoglobulin G raised against purified native *A. niger* PhyA was used as the primary antibody and was diluted 1:5,000 prior to application. A goat anti-rabbit antibody with horseradish peroxidase (Bio-Rad) was used for the colorimetric detection.

Example 28

Thermostability

The enzyme was diluted in 0.2 M citrate, pH 5.5 to give a phytase activity of 0.2 U/ml. The diluted samples were incubated for 15 min at 4, 37, 55, 65, 75, and 95° C. After the samples were cooled on ice for 30 min, their remaining phytase activities were measured as described in Example 25 (above).

Example 29

Hydrolysis of Phytate in Soybean Meal

The effectiveness of the expressed phytases in releasing phytate phosphorus from soybean meal was measured by incubating soybean meal with phytase (0 to 1000 U/kg of sample) in 0.2M citrate buffer, pH 5.5 and 3.5, at 37° C. for 1 h. One gram soybean meal was added in 9 ml buffer (0.2M citrate buffer, pH 5.3 and 2.7) and incubated at 37° C. for 20 min with shaking, which gave a final pH of the suspension 5.5 and 3.5, respectively. Then, 1 ml of pre-warmed diluted enzyme was added to start the hydrolysis reaction. After incubation of the sample for 60 min at 37° C. with shaking, the reaction was stopped by adding an equal volume of 15% trichloroacetic acid. The released inorganic phosphorus was determined as previously described (Rodriguez et al., "Site-Directed Mutagenesis Improves Catalytic Efficiency and Thermostability of *Escherichia coli* pH 2.5 Acid Phosphatase/Phytase Expressed in *Pichia pastoris*," *Arch. Biochem. Biophys.* 382:105-112 (2000), which is hereby incorporated by reference in its entirety).

Example 30

Statistical Analysis

Experimental results were analyzed by one-way-ANOVA and t-test using the Minitab release 13 for Windows.

Example 31

Single Mutations: Design of Mutations

A total of 11 mutants were prepared at the substrate binding sites of K91, K94, E228, D262, K300, and K301. Another two mutants were made at site of Q50 to improve its activity (Table 5). The designed mutations had no apparent effect on the calculated molecular mass or isoelectric point of PhyA.

TABLE 5

Change of DNA Sequence, Amino Acid and Charge Environment in the PhyA Variants with Single Mutations.

| Mutants | Charge change | Base change | Molecular weight (kDa) | Isoelectric point |
|---|---|---|---|---|
| WT | NA | NA | 51.09 | 4.94 |
| Q50L | N to N | CAA to CTA | 51.07 | 4.94 |
| Q50P | N to N | CAA to CCA | 51.06 | 4.94 |
| K91A | (+) to N | AAG to GCG | 51.03 | 4.89 |
| K91E | (+) to (−) | AAG to GAG | 51.09 | 4.85 |
| K94E | (+) to (−) | AAA to GAA | 51.09 | 4.85 |
| E228Q | (−) to N | GAA to CAA | 51.09 | 4.99 |
| E228K | (−) to (+) | GAA to AAA | 51.11 | 5.05 |
| D262H | (−) to (+) | GAC to CAC | 51.09 | 5.05 |

TABLE 5-continued

Change of DNA Sequence, Amino Acid and Charge Environment in the PhyA Variants with Single Mutations.

| Mutants | Charge change | Base change | Molecular weight (kDa) | Isoelectric point |
|---|---|---|---|---|
| K300R | (+) to (+) | AAA to AGA | 51.12 | 4.94 |
| K300T | (+) to N | AAA to ACA | 51.06 | 4.89 |
| K300D | (+) to (−) | AAA to GAT | 51.07 | 4.84 |
| K300E | (+) to (−) | AAA to GAA | 51.09 | 4.85 |
| K301E | (+) to (−) | AAG to GAG | 51.09 | 4.85 |

N: Neutral,
(+): Basic,
(−): Acidic.

Example 32

Phytase Activity Yield, Optimal pH, and Relative Activity at pH 2.5, 3.5, and 5.5.

*Pichia pastoris* X33 transformants of each mutant were selected from more than 200 colonies on YPD agar containing zeocin (100 μg/ml). To compare phytase activity yield, phytase activity of each mutant transformant was determined at 0.2M citrate buffer, pH 5.5. The results were expressed in Table 6 as the means±SD of multiple colonies, and the highest yield was listed in the parenthesis. As the wild-type enzyme has its pH optima at 5.5 (the highest activity) and 2.5 and lowest activity at pH 3.5, the differences in the activity ratios of pH 3.5/pH 5.5 and pH 3.5/pH 2.5 reflect the changes of the enzyme profiles. The higher ratios than those of wild-type indicate an improvement at pH 3.5 (stomach pH). As the buffer also affects the ratio and there are at least two buffers for pH 3.5, citrate and glycine buffers have also been compared.

The results in Table 6 are summarized as follows: At the assay condition (0.2 M citrate, pH 5.5), only E228Q, K300T, and K300D had similar activity to that of wild-type, while Q50L, K91E, E228K, D26H, K300R, and K301E had much lower activity than that of wild-type. Compared with the wild-type, mutants Q50L, K91E, D262H, K300T, K300D, and K300E lost the pH 2.5 optimum. Mutants Q50P, K94E, E228K, and K301E had shifted one or two of the two pH optima. In contrast, mutants K91A and E228Q maintained the two pH optima. The activity ratios at pH 3.5 (glycine) to pH 5.5 or 2.5 for all the mutants except for K91A, K94E, and E228Q were elevated, due to the activity rise at pH 3.5 and or the activity decreases at pH 5.5 and 2.5. The most striking changes were seen in mutants E228K and K301E in comparison with pH 5.5 and mutants Q50L, K91E, E228K, D262H, and K300T in comparison with pH 2.5. The activity ratios at pH 3.5/5.5 using citrate as the buffer were not changed much compared with the wild-type in all mutants except for E228K and K301E.

TABLE 6

Phytase Activity of *P. pastoris* Transformants at 37° C. and Different pH.

| Mutants | Phytase activity[a] (U/ml culture) | Optimal pH[b] | Ratio of phytase activity[c] 3.5C/5.5C | 3.5G/5.5C | 3.5G/2.5G |
|---|---|---|---|---|---|
| WT | 17.8 ± 14.7 (50.1) | 5 to 5.5 & 2.5 | 0.65 ± 0.007 | 0.38 ± 0.012 | 0.55 ± 0.025 |
| Q50L | 6.3 ± 2.7 (9.7) | 5.0 | 0.71 ± 0.003 | 0.68 ± 0.014 | 1.51 ± 0.031 |
| Q50P | 11.7 ± 9.4 (35.4) | 5.5 & 3 | 0.68 ± 0.004 | 0.50 ± 0.009 | 0.94 ± 0.017 |

TABLE 6-continued

Phytase Activity of *P. pastoris* Transformants at 37° C. and Different pH.

| Mutants | Phytase activity[a] (U/ml culture) | Optimal pH[b] | Ratio of phytase activity[c] 3.5C/5.5C | 3.5G/5.5C | 3.5G/2.5G |
|---|---|---|---|---|---|
| K91A | 13.1 ± 6.3 (24.9) | 5 to 5.5 & 2.5 | 0.66 ± 0.009 | 0.33 ± 0.002 | 0.55 ± 0.004 |
| K91E | 3.5 ± 2.2 (6.5) | 5 to 5.5 | 0.46 ± 0.005 | 0.46 ± 0.030 | 1.76 ± 0.114 |
| K94E | 7.2 ± 3.6 (13.3) | 5 to 5.5 & 2.0 | 0.64 ± 0.016 | 0.34 ± 0.009 | 0.56 ± 0.014 |
| E228Q | 15.1 ± 8.7 (31.2) | 5 to 5.5 & 2.5 | 0.69 ± 0.012 | 0.34 ± 0.012 | 0.52 ± 0.019 |
| E228K | 4.9 ± 3.7 (10.7) | 4.0 & 3.0 | 2.10 ± 0.027 | 1.72 ± 0.012 | 1.08 ± 0.009 |
| D262H | 2.3 ± 1.9 (6.8) | 5.0 | 0.82 ± 0.001 | 0.87 ± 0.020 | 1.51 ± 0.034 |
| K300R | 7.2 ± 4.8 (17.1) | 5.0 & 2.5 | 0.84 ± 0.012 | 0.59 ± 0.007 | 0.65 ± 0.014 |
| K300T | 15.9 ± 13.1 (42.0) | 5 to 5.5 | 0.72 ± 0.023 | 0.69 ± 0.011 | 1.10 ± 0.008 |
| K300D | 16.0 ± 10.7 (37.3) | 5 to 5.5 | 0.68 ± 0.007 | 0.65 ± 0.014 | 0.97 ± 0.013 |
| K300E | 13.3 ± 6.5 (23.4) | 5 to 5.5 | 0.65 ± 0.006 | 0.61 ± 0.018 | 1.21 ± 0.035 |
| K301E | 3.0 ± 2.0 (7.9) | 2.5 & 4 to 4.5 | 1.61 ± 0.025 | 1.40 ± 0.014 | 0.75 ± 0.016 |

[a]Values are mean ± SD (n ≧ 12) and determined using 0.2M citrate, pH 5.5. The number in parenthesis indicates the highest yield assayed.
[b]Optimal pH is listed as the 1st & the 2nd optimal pH.
[c]Ratios of phytase activity are mean ± SD (n = 3 to 6). The ratio of phytase activity at different pH was calculated to estimate the change of pH profile: 5.5C: 0.2M citrate buffer, pH 5.5; 3.5C: 0.2M citrate buffer, pH 3.5; 3.5G: 0.2M glycine-HCl buffer, pH 3.5; 2.5G: 0.2M glycine-HCl buffer, pH 2.5.

Example 33 pH Profiles of Mutants

Each mutant enzyme was characterized for its pH profile against the wild-type (FIGS. 8A-8G). The WT PhyA expressed in *P. pastoris* showed the same unique bi-hump pH optima as those expressed in *S. cerevisiae* and *A. niger* (Han et al., "Expression of an *Aspergillus niger* Phytase Gene (phyA) in *Saccharomyces cerevisiae*," *Appl. Environ. Microbiol.* 65:1915-1918 (1999); and Ullah et al., "Extracellular Phytase (E. C. 3.1.3.8) from *Aspergillus ficuum* NRRL 3135: Purification and Characterization," *Prep. Biochem.* 17:63-91 (1987), which are hereby incorporated by reference in their entirety). Q50L mutant gave an improved phytase activity at pH 3.5 with a single optimal pH at 5. Q50P showed almost the same pH profile as wild type but the 5 to 5.5 pH optimum was shifted toward to 5.5. Substitution of lysine at 91 residue for an acidic amino acid (E) changed the pH profile to give a single optimal pH at 5 to 5.5, while a non-polar, aliphatic amino acid (A) at 91 residue showed almost the same pH profile as WT. K94E gave similar pH profile to WT between pH 3.5 to 8, but the second optimal pH at 2.5 was shifted to pH 2 causing a greater dip in activity at pH between 3 to 3.5. While the alanine substitution at 228 residue gave almost identical pH profile as WT, the basic amino acid (K) substitution at 228 residue resulted in an optimal pH at 4 with almost two fold higher activity than the activity at pH 5.5. E262H had a single optimal pH at 5, and 50% higher activity at pH 3.5 than at pH 2.5. K300E, K300D, and K300T (negative charged or neutral amino acids) showed improved phytase activity at pH 3.5, resulting in a smooth pH profile with one optimal pH at 5 to 5.5. K300R had two pH optima at 5 and 2.5. Negatively charge amino acid (E) at 301 residue resulted in a broad optimal pH ranged between 2 to 5, with a small activity drop at pH 3.5.

Example 34

Hydrolysis of Phytate in Soybean Meal

Figure 9:
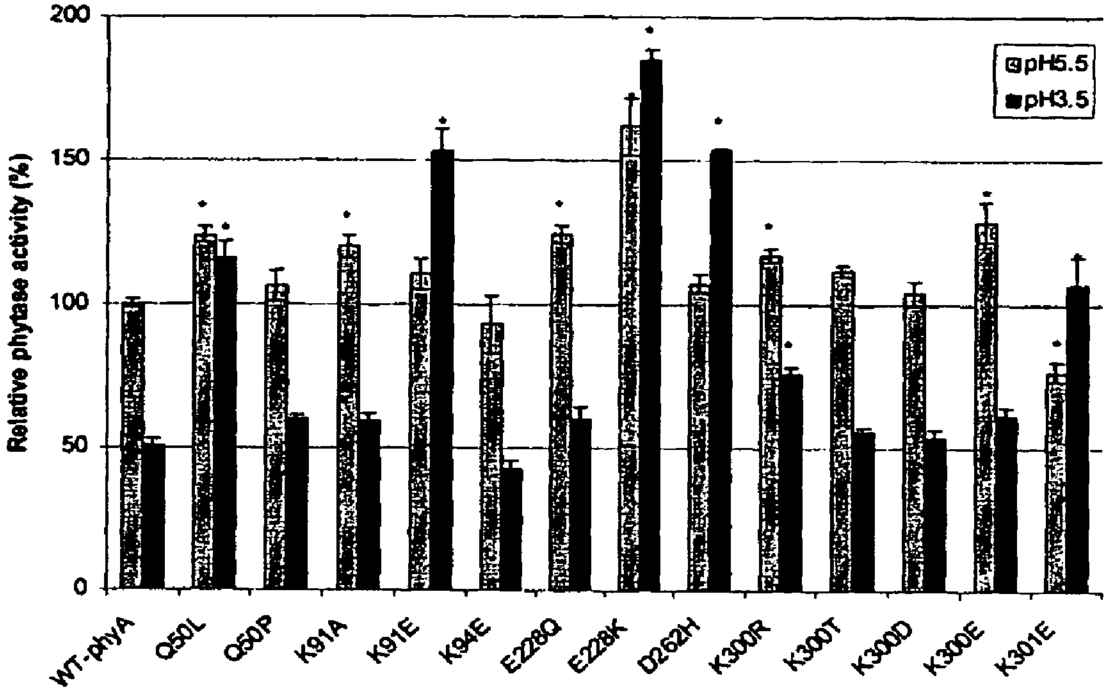
FIG. 9 is a graph showing the hydrolysis of phytate phosphors in soybean meal by different PhyA mutants (250 U/kg soybean meal) at pH 5.5 and 3.5 (0.2M citrate), 37 C for 1 h. Each bar represents the mean±SD of four replicate samples. An asterisk (*) signifies that the phytase activity of the mutant is significantly different from that of the wild-type phytase at the indicated pH.

Soybean meal was used as phytase substrate source to check the hydrolysis efficiency of the mutant enzymes since it is the main phytate source in animal diet. Some of the mutants showed quite different enzyme activity using soybean meal from the phytase activity results using sodium phytate as a substrate (FIG. 9). Mutants K91E, D262H, and K301E showed greater phosphors release from soy phytate at pH 3.5 than at pH 5.5 or the WT at pH 3.5. Compared with the WT at pH 5.5, E228K was 70% more efficient, while the other mutants were similar or less efficient. Mutant Q50L had similar phytate phosphorus hydrolysis at pH 3.5 and 5.5. In contrast, mutants Q50P, K91A, K94E, E228Q, K300R, K300T, K300D, and K300E all had lower phytate-phosphorus hydrolysis at pH 3.5 than at pH 5.5, similar to the WT.

Example 35

SDS-PAGE and Western Blot

Figure 10A:
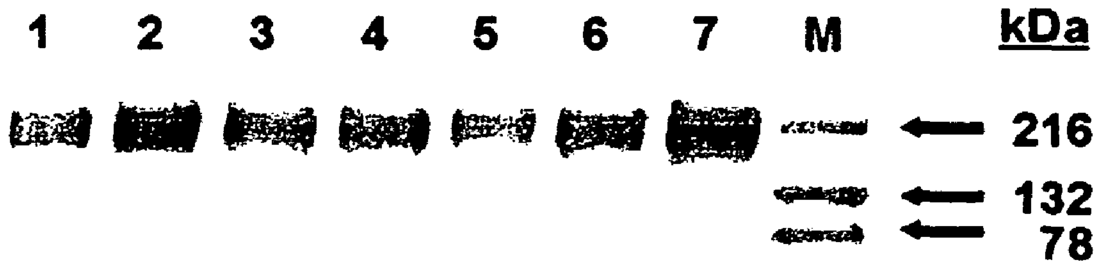
FIGS. 10A-10B show the results from a Western blot (FIG. 10A) of PhyA mutant proteins and an SDS-PAGE (FIG. 10B) of PhyA WT.
Figure 10B:

The site-directed mutagenesis did not change the molecular weight and glycosylation patterns of all mutants. A diffused single protein fragment was detected in SDS-PAGE gel and the molecular size of all the mutants was estimated to be ~78 kDa. The protein fragment was confirmed to be PhyA mutant enzyme by western blot (FIGS. 10A-10B). The molecular weight of the deglycosylated mature PhyA protein was ~49.2 kDa.

Example 36

Thermostability

Figure 11:
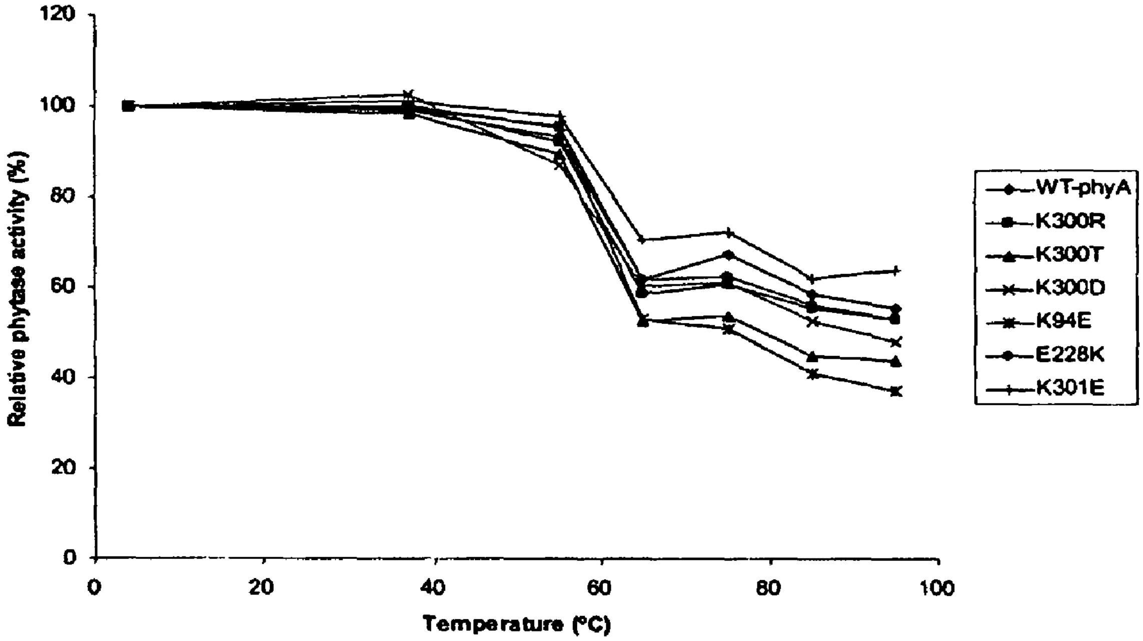
FIG. 11 is a graph showing the thermostability of purified PhyA mutant enzymes: 0.2 U of phytase was incubated for 15 min at 4, 37, 55, 65, 75, 85 and 95° C. and kept in ice for 30 min before the activity assay.
Figure 13A:
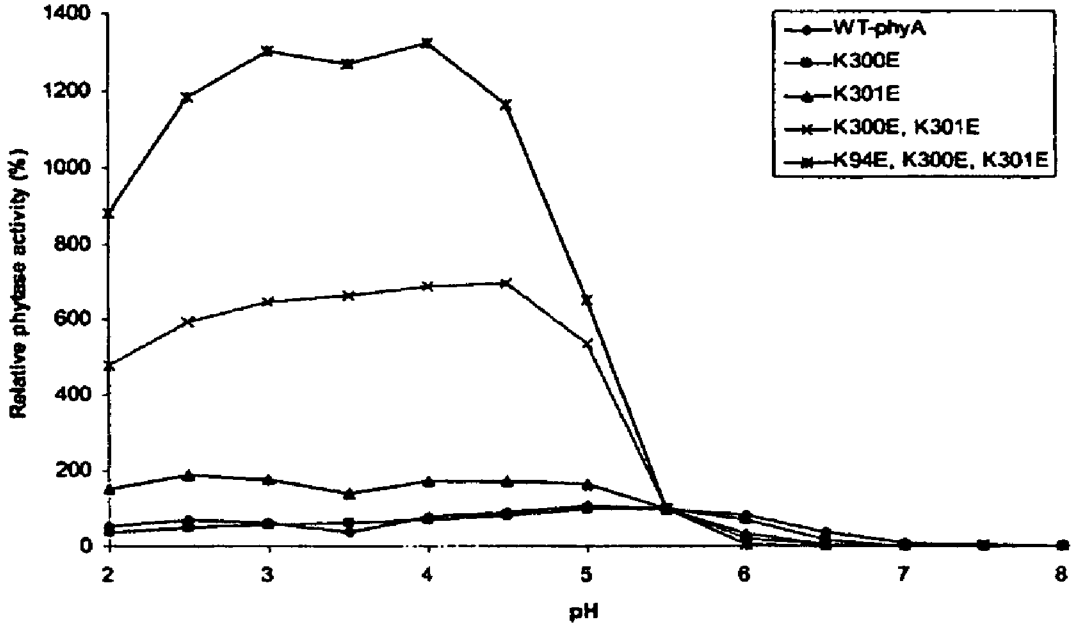
FIGS. 13A-13F are graphs showing the pH profiles of PhyA mutants with multiple changes. Combination of several mutations based on single mutation results to improve an activity at acidic pH (n=3).
Figure 13B:
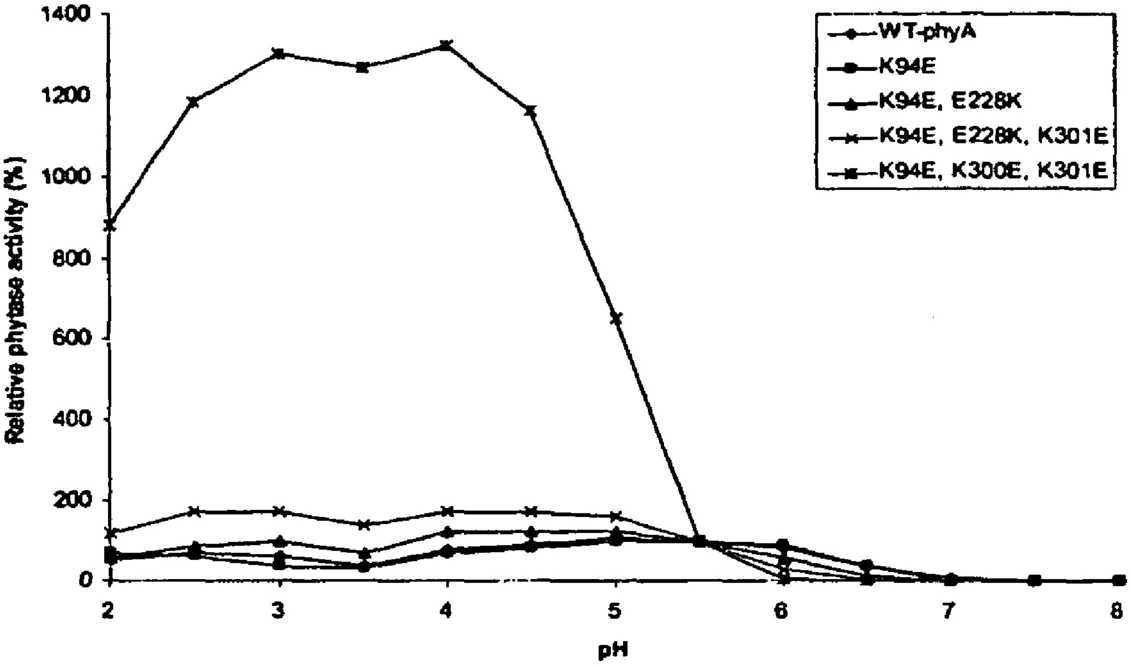
Figure 13C:
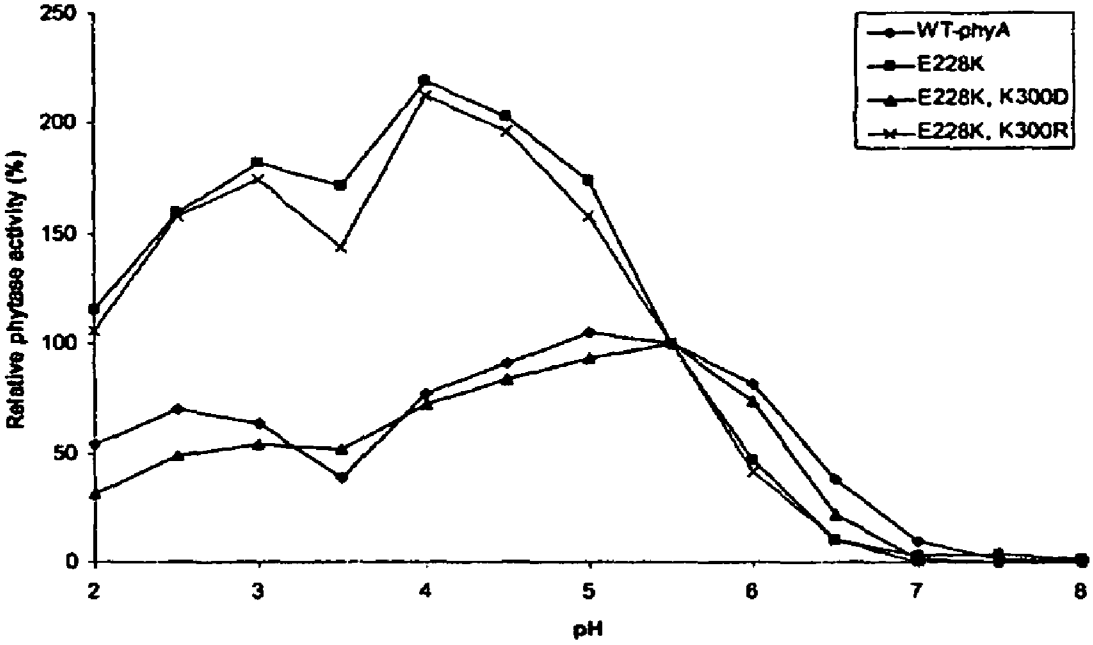
Figure 13D:
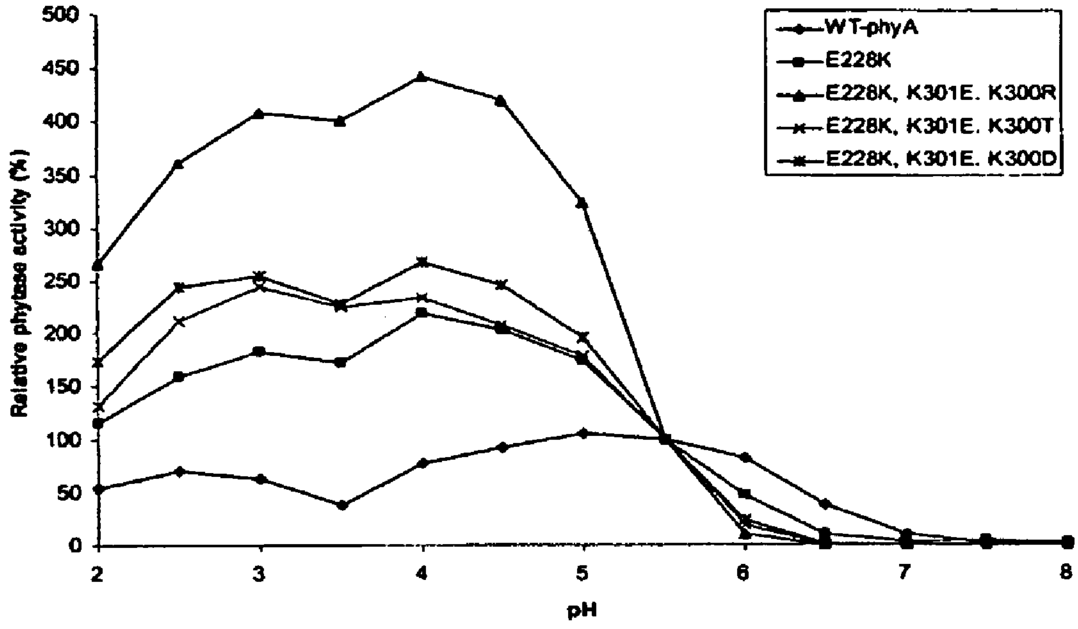
Figure 13E:
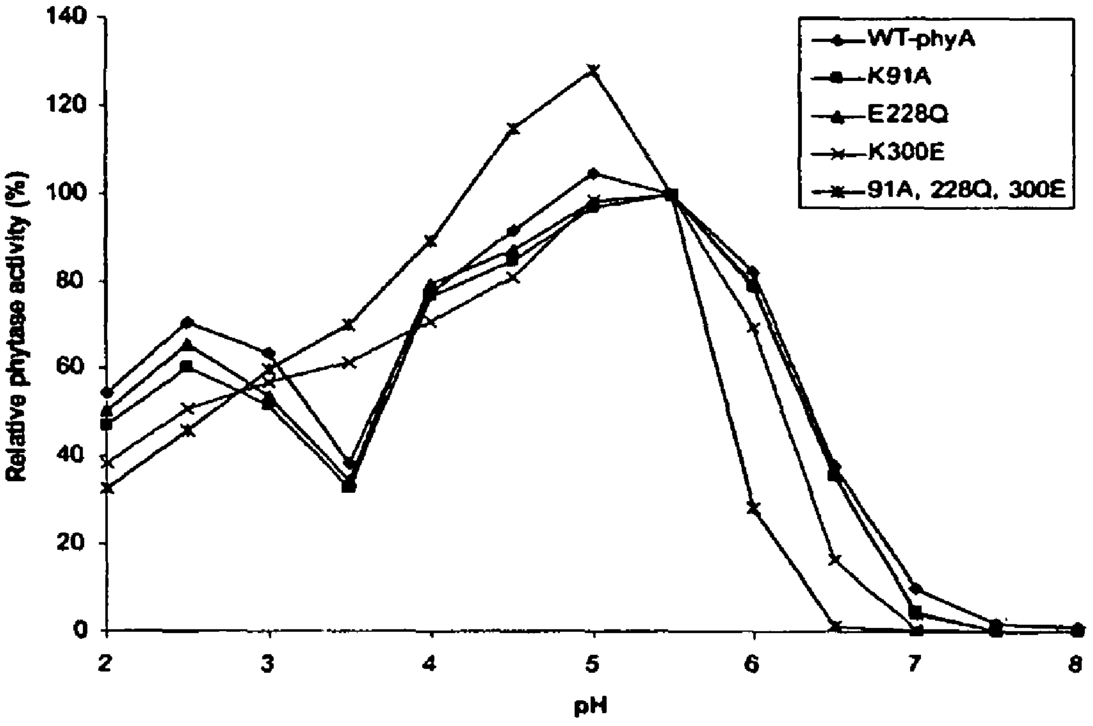
Figure 13F:
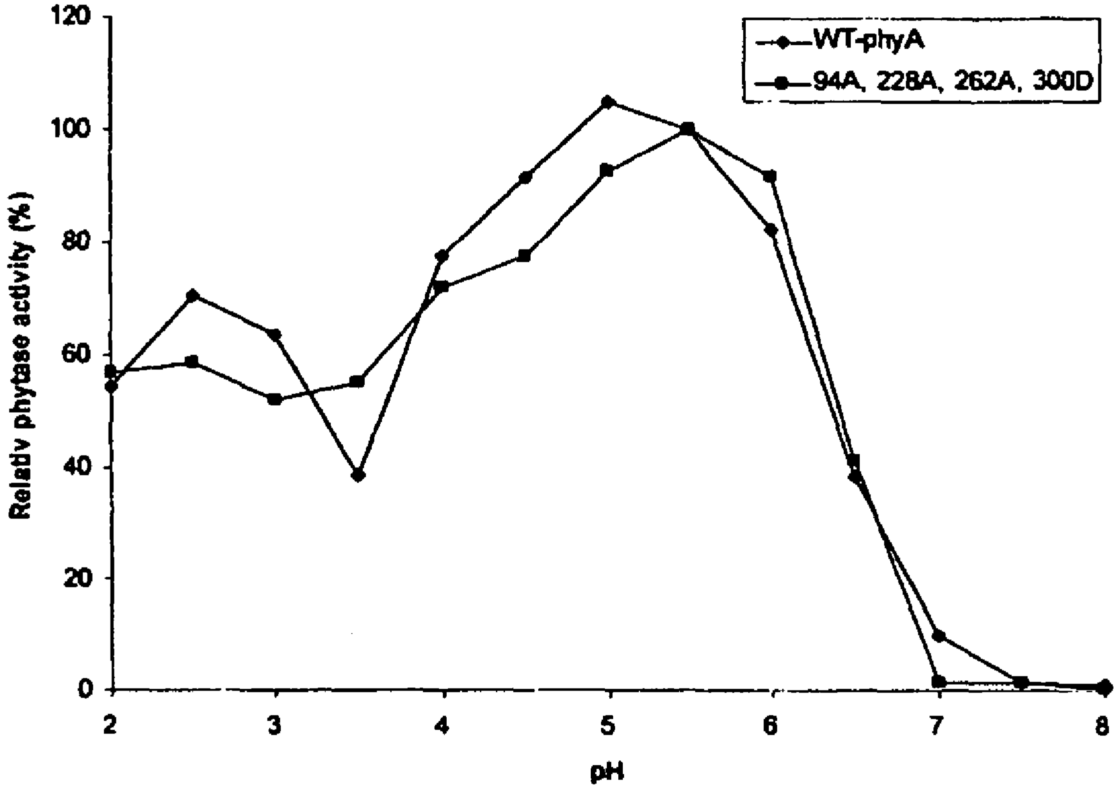

No mutant enzyme showed any significant difference in heat stability from the WT (FIG. 11). However, K94E and K300T mutants had 10 to 20% lower activity than the WT after being heated at 75 to 95° C. for 15 min.

Example 37

Multiple Mutations: Design Rationales

Among all the mutants with single mutations, E228K and K301E exhibited the most dramatic changes in pH profile, along with shifts to acidic optimal pH between 3 to 4.5. More relevantly, E228K showed an improved performance of hydrolysis of phytate from soybean meal. Based on these data, a total of 13 mutants with two to four amino acid substitutions have been designed and prepared.

Example 38

List of Mutants with Multiple Changes

The mutants are classified into 5 groups.

1. Combinations of 300K and 301K with K94 and(or) E228:
   K300E K301E
   K300E K301E K94E
   K301E E228K K94E
2. Combinations of E228K with 300K and K94:
   K300D E228K
   K300T E228K
   K300R E228K
   K94E E228K
3. Combinations of E228K and K301E with K300 or K94:
   K300R K301E E228K
   K300T K301E E228K
   K300D K301E E228K
   K94E K301E E228K
4. Combinations of K300E, K91A and E228Q (K91A and E228Q showed the improved catalytic activity and K300E showed improved pH profile):
   K300E K91A E228Q
5. *A. terreus* phytase mimicked sequence (FIG. 12):
   K300D K94A E228A D262A.

Example 39

Molecular Weight, Isoelectric Point, Phytase Activity Yield, Optimal pH, and Relative Activity at pH 2.5, 3.5, and 5.5

As in the case of single mutations, there was no significant effect of multiple mutations on the calculated molecular size or the isoelectric point (Table 7). At the assay condition (0.2 M citrate, pH 5.5), only K300D E228K, K300E K91A E228Q had good activity yield. Other mutants had much lower activity yield than the WT (Table 8). Compared with the WT, mutants K300D E228K and K300D K94A E228A D262A, K300E K91A E228Q lost the pH 2.5 optimum and showed only one pH optimal at 5.5 or 4.5-5. The other mutants had their pH optima shifted to 2.5-4.5 (Table 8). The activity ratios at pH 3.5 (glycine) to pH 5.5 or 2.5 for all the mutants were elevated, with the highest in mutant K300E K301E K94E (12.7) and followed by the mutant K300E K301E (6.6), and K300R K301E E228K (4.0) (Table 8).

TABLE 7

Change of DNA Sequence, Amino Acid, and Charge Environment in the PhyA Mutants with Multiple Changes.

| Mutants | Charge change | Base change | Molecular weight (kDa) | Isoelectric point |
|---|---|---|---|---|
| WT | NA | NA | 51.09 | 4.94 |
| K300E | (+) to (−) | AAA to GAA | 51.09 | 4.77 |
| K301E | (+) to (−) | AAG to GAG | | |
| K300D | (+) to (−) | AAA to GAT | 51.07 | 4.94 |
| E228K | (−) to (+) | GAA to AAA | | |
| K300T | (+) to N | AAA to ACA | 51.06 | 4.99 |
| E228K | (−) to (+) | GAA to AAA | | |
| K300R | (+) to (+) | AAA to AGA | 51.11 | 5.05 |
| E228K | (−) to (+) | GAA to AAA | | |
| E228K | (−) to (+) | GAA to AAA | 51.09 | 4.94 |
| K94E | (+) to (−) | AAA to GAA | | |
| K300R | (+) to (+) | AAA to AGA | 51.12 | 4.94 |
| K301E | (+) to (−) | AAG to GAG | | |
| E228K | (−) to (+) | GAA to AAA | | |
| K300T | (+) to N | AAA to ACA | 51.06 | 4.89 |
| K301E | (+) to (−) | AAG to GAG | | |
| E228K | (−) to (+) | GAA to AAA | | |
| K300D | (+) to (−) | AAA to GAT | 51.07 | 4.84 |
| K301E | (+) to (−) | AAG to GAG | | |
| E228K | (−) to (+) | GAA to AAA | | |
| K300E | (+) to (−) | AAA to GAA | 51.09 | 4.70 |
| K301E | (+) to (−) | AAG to GAG | | |
| K94E | (+) to (−) | AAA to GAA | | |
| K301E | (+) to (−) | AAG to GAG | 51.09 | 4.85 |
| E228K | (−) to (+) | GAA to AAA | | |
| K94E | (+) to (−) | AAA to GAA | | |
| K300E | (+) to (−) | AAA to GAA | 51.03 | 4.84 |
| K91A | (+) to N | AAG to GCG | | |
| E228Q | (−) to N | GAA to CAA | | |
| K300D | (+) to (−) | AAA to GAC | 51.92 | 4.87 |
| K94A | (+) to N | AAA to GCA | | |
| E228A | (−) to N | GAA to GCA | | |
| D262A | (−) to N | GAC to GCC | | |

N: Neutral,
(+): Basic,
(−): Acidic

TABLE 8

Phytase Activity of *P. pastoris* Transformants of PhyA Mutants (Multiple Changes) at 37° C. and Different pH.

| Mutants | Phytase activity (U/ml culture)[a] | Optimal pH[b] | Ratio of phytase activity[c] 3.5C/5.5C | 3.5G/5.5C | 3.5G/2.5G |
|---|---|---|---|---|---|
| WT | 17.8 ± 14.7 (50.1) | 5 to 5.5 & 2.5 | 0.65 ± 0.007 | 0.38 ± 0.012 | 0.55 ± 0.025 |
| K300E K301E | 0.78 ± 0.45 (2.0) | 3 to 4.5 | 6.73 ± 0.103 | 6.62 ± 0.114 | 1.11 ± 0.031 |
| K300D E228K | 10.9 ± 6.4 (25.4) | 5.5 | 0.61 ± 0.010 | 0.52 ± 0.012 | 1.07 ± 0.025 |
| K300T E228K | No activity | NA | NA | NA | NA |
| K300R E228K | 3.7 ± 2.0 (10.0) | 4.0 & 3.0 | 2.06 ± 0.001 | 1.44 ± 0.226 | 0.91 ± 0.143 |
| E228K K94E | 5.6 ± 2.7 (8.7) | 4.5 & 3.0 | 1.08 ± 0.012 | 0.69 ± 0.039 | 0.79 ± 0.044 |
| K300R K301E E228K | 1.9 ± 2.0 (4.7) | 4.0 | 4.31 ± 0.062 | 4.00 ± 0.049 | 1.11 ± 0.019 |
| K300T K301E E228K | 3.8 ± 2.3 (6.3) | 3.0 & 4.0 | 2.46 ± 0.027 | 2.25 ± 0.032 | 1.06 ± 0.049 |
| K300D K301E E228K | 1.5 ± NA (1.5)* | 4.0 & 3.0 | 2.75 ± 0.001 | 2.28 ± 0.027 | 0.93 ± 0.034 |
| K300E K301E K94E | 0.24 ± 0.10 (0.46) | 4.0 & 3.0 | 13.54 ± 0.155 | 12.68 ± 0.142 | 1.07 ± 0.012 |
| K301E E228K K94E | 2.96 ± 1.95 (7.8) | 4 to 4.5 & 2.5 to 3 | 1.70 ± 0.031 | 1.38 ± 0.066 | 0.81 ± 0.039 |

TABLE 8-continued

Phytase Activity of *P. pastoris* Transformants of PhyA Mutants (Multiple Changes) at 37° C. and Different pH.

| Mutants | Phytase activity (U/ml culture)[a] | Optimal pH[b] | Ratio of phytase activity[c] 3.5C/5.5C | 3.5G/5.5C | 3.5G/2.5G |
|---|---|---|---|---|---|
| K300E K91A E228Q | 9.1 ± 4.08 (21.0) | 4.5 to 5.0 | 0.69 ± 0.017 | 0.70 ± 0.051 | 1.53 ± 0.111 |
| K300D K94A E228A D262A | 3.3 ± 0.95 (5.4) | 5.5 | 0.64 ± 0.027 | 0.55 ± 0.021 | 0.94 ± 0.037 |

[a]Values are mean ± SD (n ≧ 12, but only one transformant for K300D, K301E, E228K*) and determined using 0.2M citrate, pH 5.5. The number in parenthesis indicates the highest yield assayed.
[b]Optimal pH is listed as the 1st & the 2nd optimal pH.
[c]Ratios of phytase activity are mean ± SD (n = 3 to 6). The ratio of phytase activity at different pH was calculated to estimate the change of pH profile: 5.5C: 0.2M citrate buffer, pH 5.5; 3.5C: 0.2M citrate buffer, pH 3.5; 3.5G: 0.2M glycine-HCl buffer, pH 3.5; 2.5G: 0.2M glycine-HCl buffer, pH 2.5.

Example 40 pH Profiles of Mutants

Each mutant enzyme was characterized for its pH profile against the WT (FIGS. 13A-13F). Mutant K300E K301E showed a completely altered pH profile from the WT: only one broad pH optimum between 3 and 4.5 and a very low activity at pH 5 to 5.5. Adding K94E into K300E K301E further improved phytase activity at pH 2 to 4.5 by 2-3 fold and narrowed the pH optimal range somewhat. Among the four mutants with K94E, the one combined with K300E K301E showed the most significant changes and K94E E228K K301E with apparent changes as well. Adding the mutation K300D into the mutant E228K seemed to offset the changes by E228K and resulted in a similar pH profile to the WT. In contrast, adding the mutation K300R into the mutant E228K had only a slight effect on its activity at pH 3.5. Among the three mutants with E228K K301E, the addition of K300R produced at least a double improvement in activity at pH 2.5-4.5. The replacement of K300D was slightly better than that of K300T. The combination of K91A, E228Q, and K300E resulted in a single optimal pH 5, while the single mutations in K91A or E228Q essentially maintained the two pH optima as in the WT. The combination of four mutations: K94A, E228A, D262A, and K300D resulted in a single optimal pH 5.5 and a small rise in the activity dip at pH 3.5.

Example 41

Hydrolysis of Phytate in Soybean Meal

Figure 14A:
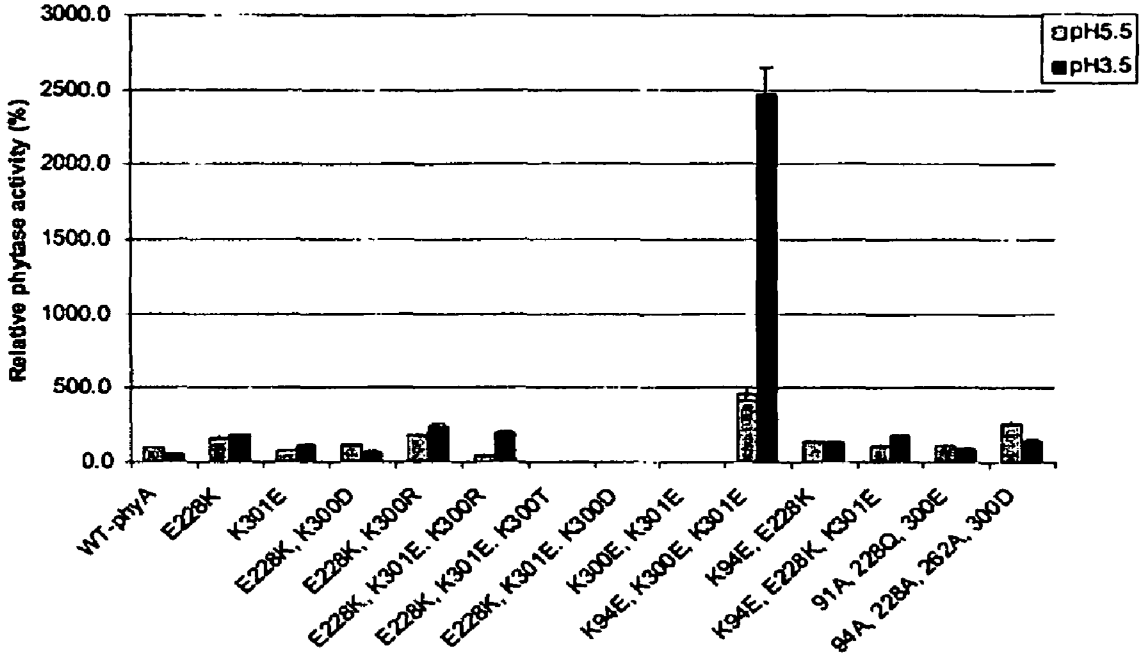
FIGS. 14A-14B are graphs showing the hydrolysis of phytate phosphors in soybean meal by different PhyA mutants with multiple changes (250 U/kg soybean meal) at pH 5.5 and 3.5 (0.2M citrate), 37 C for 1 h. Each bar represents the mean±SD of four replicate samples.
Figure 14B:
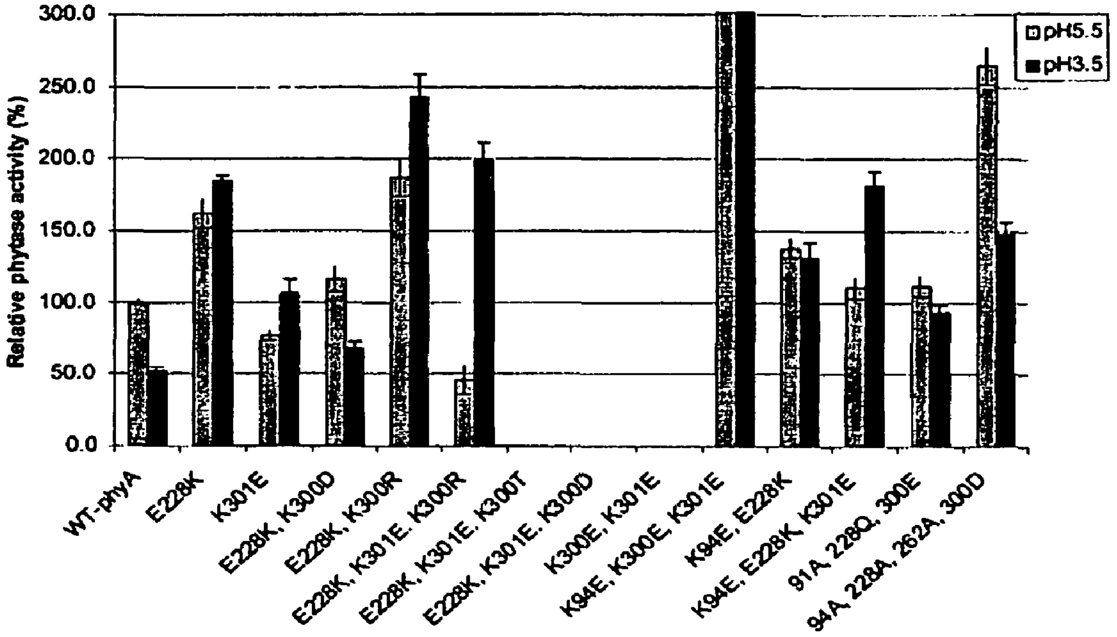

At pH 5.5, mutants E228K, E228K K300R, E228K K301E K300R, K94E K300E K301E, K94E E228K, K94E E228K K301E, and K94A, E228A D262A K300D showed greater phosphorus release from soy phytate than the WT (FIGS. 14A-14B). At pH 5.5, E228K, E228k K300R, K94E K300E K301E, and the mutant with the four combined mutations also released more phosphorus than the WT. The mutant K94E K300E K301E showed the most significant improvement in phytate-phosphorus hydrolysis at both pH 3.5 and 5.5, whereas the mutant E228K K301E K300R gave a large relative difference in phytate-phosphorus hydrolysis between pH 3.5 and 5.5.

Example 42

Analysis of Improving *Aspergillus niger* PhyA Phytase by Protein Engineering A total of 25 *A. niger* PhyA mutants have been produced by site-directed mutagenesis. There are 13 mutants with single amino acid changes and 12 mutants with combined 2 to 4 amino acid changes in the sequence. The mutations have been made to modify the substrate binding region of the enzyme and (or) to improve catalytic efficiency. All these changes have been designed based on the three-dimensional structure of PhyA and sequence comparisons among different phytases. The pH profile and the pH optima have been significantly altered by these mutations. Many mutants have demonstrated complete or favorable shifts in activity to more acidic pH ranges. A number of the mutants have shown a significant improvement in hydrolyzing phytate-phosphorus from soybean meal in vitro. A preliminary animal feeding experiment has supported these observations. The mutations have no apparent effect on the molecular size, glycosylation, immune-reactivity, isoelectric point, and thermostability. All these mutants can be selected and further improved in heat stability, protease-resistance, catalytic efficiency, and expression yield for animal feed, human food or treatment, and environmental protection. Different mutants can be used to serve specific purposes (e.g., two different mutants may be used for fish and humans, respectively).

Example 43

Animal Feeding Tests of PhyA Mutants

Experiments were conducted to test if two PhyA mutants were more effective than the wild-type enzyme in releasing phytate phosphorus to support growth and plasma phosphorus status.

Animal protocols that had been approved by the Institutional Animal Care and Use Committee of Cornell University were used. The experiment was conducted with a total of 24 weanling pigs (5-week-old) for 5 weeks. The pigs were Landrace-Yorkshire-Duroc crossbreds from the Cornell University Swine Farm. The pigs were allotted into three treatment groups on the basis of body weight, litter, and sex. The three groups of pigs were fed a corn-soybean meal basal diet ("BD") (see Table 9) supplemented with the wild-type (WT) and two of the PhyA mutants (E228K and TK10: K94E K300E K301E) at 200 U/kg feed to compare the efficacy. The BD contained adequate levels of all nutrients (NRC, "Nutrient Requirements of Swine ($10^{th}$ Ed.)," National Academy Press, Washington, D.C. (1998), which is hereby incorporated by reference in its entirety), except that the BD contained no inorganic phosphorus supplement and had a reduced calcium level (0.51%) (Lei et al., "Calcium Level Affects the Efficacy of Supplemental Microbial Phytase in Corn-Soybean Meal Diets of Weanling Pigs," *J. Anim. Sci.* 72(1):139-143 (1994), which is hereby incorporated by reference in its entirety).

TABLE 9

Composition of Basal Diet[a].

| Ingredients | % |
|---|---|
| Corn | 67.10 |
| Soybean meal, 48% CP | 28.00 |
| Spray-dried plasma protein | 1.50 |
| Limestone | 1.05 |
| L-Lysine-HCl | 0.10 |
| Corn Oil | 1.00 |
| Vitamin/mineral premix[b] | 0.25 |
| Salt | 0.50 |
| Antibiotics[c] | 0.50 |
| Total | 100.00 |
| Nutritive values (as fed)[d] | |
| Crude protein | 20.04% |
| $Ca_{total}$ | 0.51% |
| $P_{total}$ | 0.41% |
| $P_{available}$ | 0.10% |
| $Ca:P_{total}$ | 1.24 |

[a]Various of phytase enzyme preparations were added at the experimental diets at the expense of corn.
[b]Vitamin and mineral premix supplies (per kg diet): 5,500 IU vitamin A, 1,100 IU vitamin $D_3$, 24 IU vitamin E, 0.73 mg vitamin K, 4.4 mg riboflavin, 17.6 mg pantothenic acid, 26.4 mg niacin, 66 mg choline, 26 μg vitamin $B_{12}$, 0.27 g Mg (MgO), 32 mg Mn (MnO), 0.4 mg I ($C_2H_8N_2$•2HI, ethylenediamine dihydroiodide), 10 mg Cu ($CuSO_4$•$5H_2O$), 0.3 mg Se ($Na_2SeO_3$), 90 mg Zn (ZnO), and 80 mg Fe ($FeSO_4$•$7H_2O$).
[c]Provided 110 mg of chlortetracycline, 110 mg sulfathiazole, and 55 mg of penicillin per kg of diet.
[d]Calculated (NRC, 1998).

Pigs were individually penned in an environmentally-controlled barn (23-25° C.; light:dark cycle, 12 h) and allowed free access to feed and water. Feed waste was collected daily, and body weight of pigs was measured weekly for calculation of average daily gain ("ADG"), average daily feed intake ("ADFI"), and Gain/Feed ratio. Blood samples of individual, overnight-fasted (for 8 h) pigs were collected from the anterior vena cava into heparinized syringes at the start and at the end of trial to assay for plasma alkaline phosphatase activity and plasma inorganic phosphorus concentration.

Biochemical Analysis: Plasma was prepared by centrifuging ice-chilled whole blood samples at 3,000×g (GS-6KR Centrifuge, Beckman Instruments Inc.) for 10 minutes at 4° C. For determination of inorganic phosphorus concentration, plasma was deproteinated with 12.5% trichloroacetic acid and assayed using Elon (p-methylaminophenol sulfate) solution (Gomori, "A Modification of the Colorimetric Phosphorus Determination for Use with the Photoelectric Colorimeter," *J. Lab. Clin. Med.* 27:955-960 (1942), which is hereby incorporated by reference in its entirety). Plasma alkaline phosphatase activity was determined by the hydrolysis of p-nitrophenol phosphate to p-nitrophenol (Bowers et al., "A Continuous Spectophotometric Method for Measuring the Activity of Serum Alkaline Phosphatase," *Clin. Chem.* 12:70-89 (1966), which is hereby incorporated by reference in its entirety). The enzyme unit was defined as 1 mmol of p-nitrophenol released per minute at 30° C.

Figure 15:
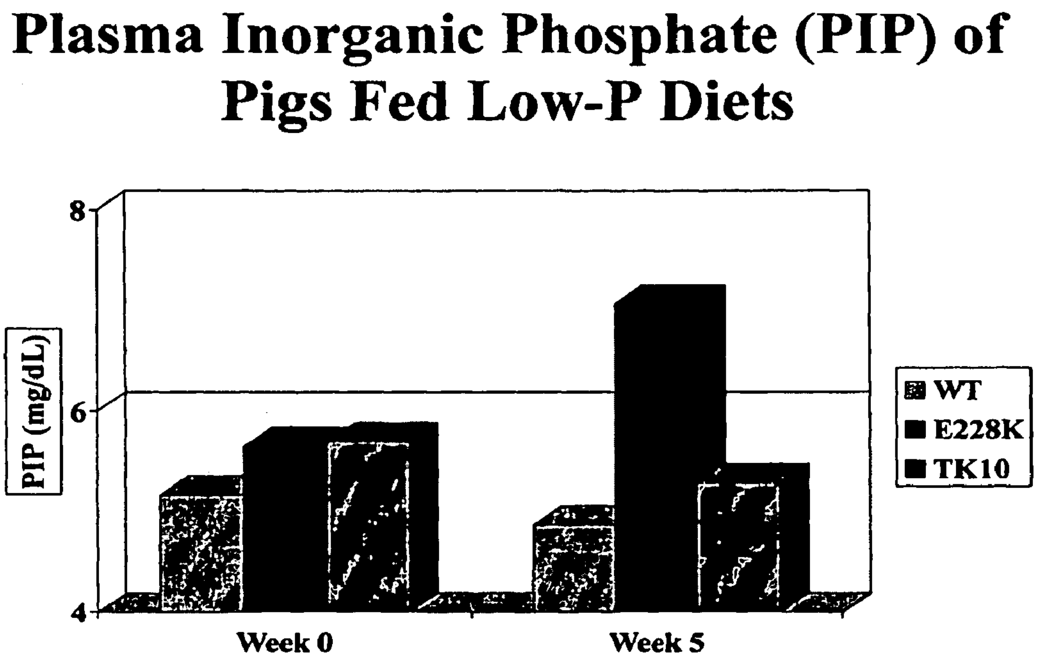
FIG. 15 is a graph showing the plasma inorganic phosphate ("PIP") of pigs fed low-P diets.
Figure 16:
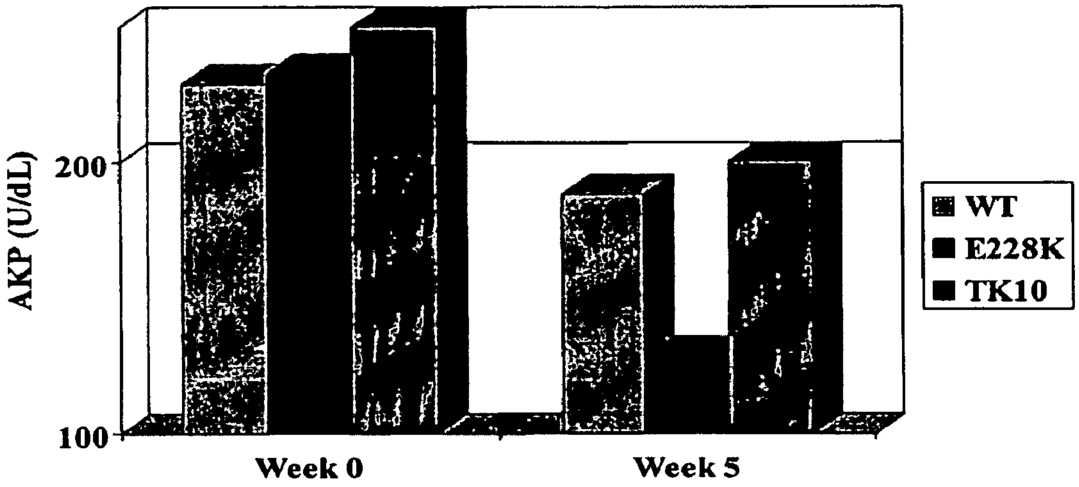
FIG. 16 is a graph showing the plasma alkaline phosphatase ("AKP") activity of pigs fed low-P diets.
Figure 17:
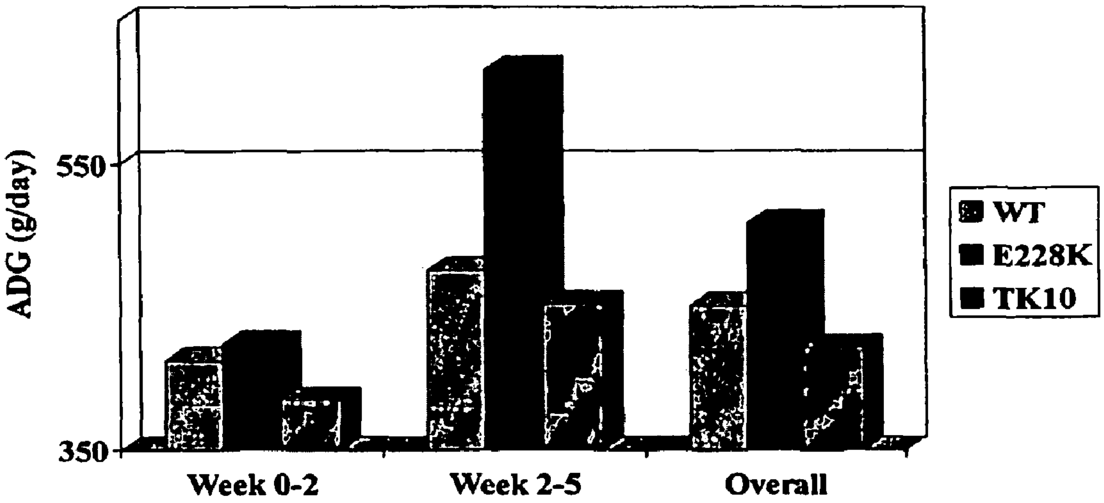
FIG. 17 is a graph showing the average daily gain ("ADG") of pigs fed low-P diets.
Figure 18:
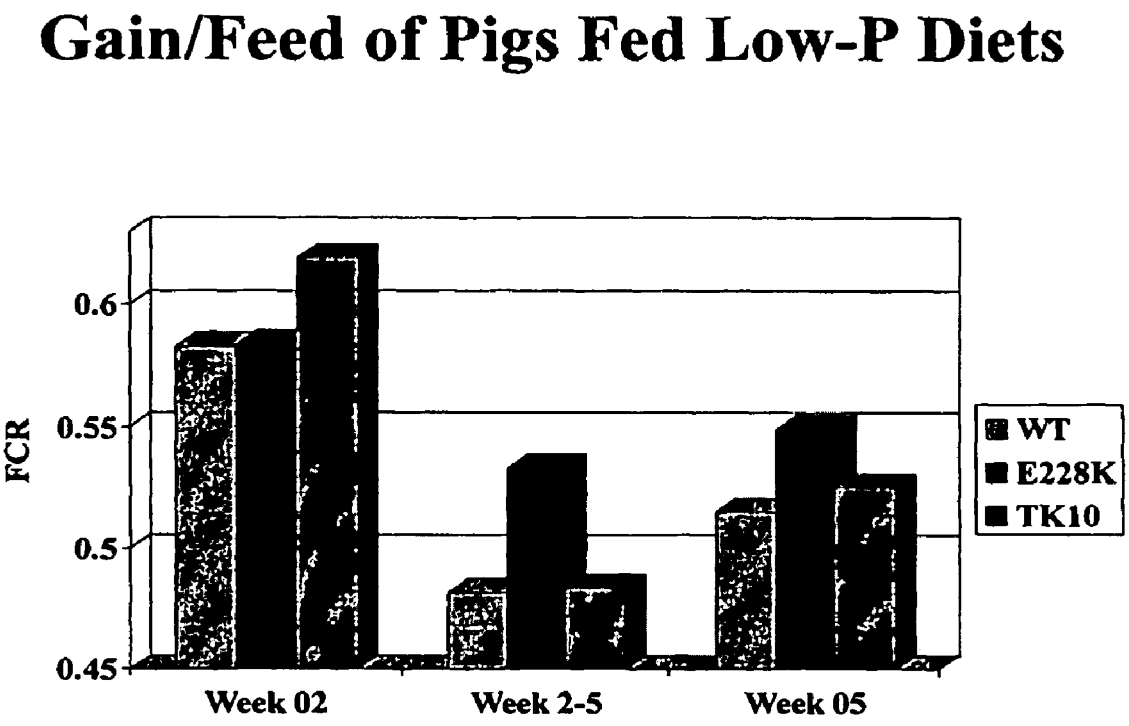
FIG. 18 is a graph showing the gain/feed of pigs fed low-P diets.

Mutant E228K demonstrated better performance than the wild-type enzyme. In particular, as compared to pigs fed the WT PhyA enzyme, pigs fed Mutant E228K had: (i) greater daily gain and feed efficiency (FIGS. 17 and 18); (ii) higher plasma inorganic phosphorus (FIG. 15); and (iii) lower plasma alkaline phosphatase activity (less bone resorption) (FIG. 16). Mutant TK10 showed no improvement over the wild-type in animal feeding.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated mutant phytase comprising either:

(i) an amino acid sequence having at least 96 percent sequence identity to SEQ ID NO:2 and containing at least one amino acid residue substitution selected from the group consisting of amino acid residue 50, 91, 94, 262, 300, and 301 of SEQ ID NO:2; or (ii) an amino acid sequence having at least 96 percent sequence identity to SEQ ID NO: 4 and containing a substitution of amino acid residue 363 of SEQ ID NO: 4, wherein said mutant phytase comprise phytase activity.

2. The isolated mutant phytase according to claim 1, wherein said isolated mutant phytase is in pure or non-pure form.

3. The isolated mutant phytase according to claim 1, wherein said isolated mutant phytase is recombinant.

4. The isolated mutant phytase according to claim 1, wherein said at least one substitution is of amino acid residue 50 of SEQ ID NO:2 and is selected from the group consisting of Q50L and Q50P.

5. The isolated mutant phytase according to claim 1, wherein said at least one substitution is of amino acid residue 91 of SEQ ID NO:2 and is selected from the group consisting of K91A and K91E.

6. The isolated mutant phytase according to claim 1, wherein said at least one substitution is of amino acid residue 94 of SEQ ID NO:2 and comprises K94E.

7. The isolated mutant phytase according to claim 1, wherein said at least one substitution is of amino acid residue 262 of SEQ ID NO:2 and comprises D262H.

8. The isolated mutant phytase according to claim 1, wherein said at least one substitution is of amino acid residue 300 of SEQ ID NO:2 and is selected from the group consisting of K300R, K300T, K300D, and K300E.

9. The isolated mutant phytase according to claim 1, wherein said at least one substitution is of amino acid residue 301 of SEQ ID NO:2 and comprises K301E.

10. The isolated mutant phytase according to claim 1, wherein said substitution of amino acid residue 363 of SEQ ID NO:4 is M363L.

11. The isolated mutant phytase according to claim 1, wherein said at least one substitution comprises a double-substitution.

12. The isolated mutant phytase according to claim 11, wherein said double-substitution is K300E/K301E.

13. The isolated mutant phytase according to claim 1, wherein said at least one substitution comprises a triple-substitution.

14. The isolated mutant phytase according to claim 13, wherein said triple-substitution is K300E/K30 1 E/K94E.

15. The isolated mutant phytase according to claim 1, wherein said at least one substitution comprises a quadruple-substitution.

16. An animal feed composition comprising the isolated mutant phytase according to claim 1.

17. A foodstuff comprising an animal feed composition according to claim 16.

18. The foodstuff according to claim 17, wherein the foodstuff further comprises greater than 1.0% by weight vitamin and mineral mix.

19. The foodstuff according to claim 17, wherein the foodstuff further comprises soybean meal.

20. The foodstuff according to claim 17, wherein the foodstuff further comprises antibiotics.

21. A method of feeding a monogastric animal comprising: feeding to the animal a foodstuff in combination with the isolated mutant phytase according to claim 1.

22. The method according to claim 21, wherein the animal is a fowl species.

23. The method according to claim 21, wherein the animal is a porcine species.

24. The method according to claim 21, wherein the animal is an aquatic species.

25. The method according to claim 21, wherein the animal is a domestic animal selected from the group consisting of a canine species and a feline species.

26. The method according to claim 21, wherein the animal is a mammalian species selected from the group consisting of an *Oryctolagus* species, a *Capra* species, a *Bos* species, an *Equus* species, and an *Ovis* species.

27. The method according to claim 21, wherein there are about 100-2,000 units of the mutant phytase per kilogram of the foodstuff.

28. The method according to claim 21, wherein the mutant phytase has an alterered pH profile and an altered pH optima compared to a corresponding non-mutant phytase.

29. A method of improving the nutritional value of a foodstuff consumed by an animal, said method comprising:

providing a foodstuff comprising myo-inositol hexakisphosphate;

providing a mutant phytase according to claim 1; and feeding to the animal the foodstuff in combination with the mutant phytase under conditions effective to increase the bioavailability of phosphate from phytate.

30. The method according to claim 29, wherein the animal is poultry.

31. The method according to claim 29, wherein the animal is a porcine species.

32. The method according to claim 29, wherein the animal is an aquatic species.

33. The method according to claim 29, wherein the animal is a domestic animal selected from the group consisting of a canine species and a feline species.

34. The method according to claim 29, wherein the animal is a mammalian species selected from the group consisting of an *Oryctolagus* species, a *Capra* species, a *Bos* species, an *Equus* species, and an *Ovis* species.

35. The method according to claim 29, wherein the animal is a human.

36. The method according to claim 29, wherein the foodstuff is pig feed.

37. The method according to claim 29, wherein the foodstuff is poultry feed.

38. The method according to claim 29, wherein the animal is fed the foodstuff in combination with about 100-2,000 units of the mutant phytase per kilogram of the foodstuff.

39. A method of improving the nutritional value of a foodstuff consumed by humans, said method comprising:

providing a mutant phytase according to claim 1 and combining said mutant phytase with a foodstuff consumed by humans under conditions effective to increase the bioavailability of minerals from said foodstuff, wherein said minerals are selected from the group consisting of iron, zinc, phosphorus, and calcium.

* * * * *

SEQUENCE LISTING

```
<160> NUMBER OF SEQ ID NOS: 69

<210> SEQ ID NO 1
<211> LENGTH: 2665
<212> TYPE: DNA
<213> ORGANISM: Aspergillus niger

<400> SEQUENCE: 1

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600
```

-continued

```
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcgaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
cccctttctgt gacctgttca cccatgacga atggatcaac tacgactacc tccagtcctt   1680
gaaaaagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                         2665
```

<210> SEQ ID NO 2
<211> LENGTH: 467
<212> TYPE: PRT
<213> ORGANISM: Aspergillus niger

<400> SEQUENCE: 2

Met Gly Val Ser Ala Val Leu Leu Pro Leu Tyr Leu Leu Ser Gly Val

-continued

```
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430
```

-continued

Leu His Gly Cys Pro Val Asp Ala Leu Gly Arg Cys Thr Arg Asp Ser
435 440 445

Phe Val Arg Gly Leu Ser Phe Ala Arg Ser Gly Gly Asp Trp Ala Glu
450 455 460

Cys Phe Ala
465

<210> SEQ ID NO 3
<211> LENGTH: 1455
<212> TYPE: DNA
<213> ORGANISM: Aspergillus fumigatus

<400> SEQUENCE: 3
atggtgactc tgactttcct gctttcggcg gcgtatctgc tttctgggtg agtggcttgg 60
atctattgct cggatagggc tgtggtgctg attctgaaac ggagtagagt gtctgcggca 120
cctagttctg ctggctccaa gtcctgcgat acggtagacc tcgggtacca gtgctcccct 180
gcgacttctc atctatgggg ccagtactcg ccattctttt cgctcgagga cgagctgtcc 240
gtgtcgagta agcttcccaa ggattgccgg atcaccttgg tacaggtgct atcgcgccat 300
ggagcgcggt acccaaccag ctccaagagc aaaaagtata agaagcttgt gacggcgatc 360
caggccaatg ccaccgactt caagggcaag tttgcctttt tgaagacgta caactatact 420
ctgggtgcgg atgacctcac tccctttggg gagcagcagc tggtgaactc gggcatcaag 480
ttctaccaga ggtacaaggc tctggcgcgc agtgtggtgc cgtttattcg cgcctcaggc 540
tcggaccggg ttattgcttc gggagagaag ttcatcgagg ggttccagca ggcgaagctg 600
gctgatcctg gcgcgacgaa ccgcgccgct ccggcgatta gtgtgattat tccggagagc 660
gagacgttca acaatacgct ggaccacggt gtgtgcacga agtttgaggc gagtcagctg 720
ggagatgagg ttgcggccaa tttcactgcg ctctttgcac ccgacatccg agctcgcgcc 780
gagaagcatc ttcctggcgt gacgctgaca gacgaggacg ttgtcagtct aatggacatg 840
tgttcgtttg atacggtagc gcgcaccagc gacgcaagtc agctgtcacc gttctgtcaa 900
ctcttcactc acaatgagtg gaagaagtac aactaccttc agtccttggg caagtactac 960
ggctacggcg caggcaaccc tctgggaccg gctcagggga tagggttcac caacgagctg 1020
attgcccggt tgactcgttc gccagtgcag gaccacacca gcactaactc gactctagtc 1080
tccaacccgg ccaccttccc gttgaacgct accatgtacg tcgacttttc acacgacaac 1140
agcatggttt ccatcttctt tgcattgggc ctgtacaacg gcactgaacc cttgtcccgg 1200
acctcggtgg aaagcgccaa ggaattggat gggtattctg catcctgggt ggtgcctttc 1260
ggcgcgcgag cctacttcga gacgatgcaa tgcaagtcgg aaaaggagcc tcttgttcgc 1320
gctttgatta atgaccgggt tgtgccactg catggctgcg atgtggacaa gctggggcga 1380
tgcaagctga atgactttgt caagggattg agttgggcca gatctggggg caactgggga 1440
gagtgcttta gttga 1455

<210> SEQ ID NO 4
<211> LENGTH: 465
<212> TYPE: PRT
<213> ORGANISM: Aspergillus fumigatus

<400> SEQUENCE: 4

Met Val Thr Leu Thr Phe Leu Leu Ser Ala Ala Tyr Leu Leu Ser Gly
1 5 10 15

-continued

```
Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
        355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
```

-continued

```
        435                 440                 445

Lys Gly Leu Ser Trp Ala Arg Ser Gly Gly Asn Trp Gly Glu Cys Phe
    450                 455                 460

Ser
465


<210> SEQ ID NO 5
<211> LENGTH: 2665
<212> TYPE: DNA
<213> ORGANISM: Aspergillus niger

<400> SEQUENCE: 5

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780

ctgaagctcg gactgtgtgg gactactgat cgctgactat ctgtgcagag tcacctccgg     840

actggcagtc cccgcctcga gaaatcaatc cagttgcgat acggtcgatc aggggtatca     900

atgcttctcc gagacttcgc atctttgggg tccatacgca ccgttcttct ctctggcaaa     960

cgaatcggtc atctcccctg aggtgcccgc cggatgcaga gtcactttcg ctcaggtcct    1020

ctcccgtcat ggagcgcggt atccgaccga ctccaagggc aagaaatact ccgctctcat    1080

tgaggagatc cagcagaacg cgaccacctt tgacggaaaa tatgccttcc tgaagacata    1140

caactacagc ttgggtgcag atgacctgac tcccttcgga gaacaggagc tagtcaactc    1200

cggcatcaag ttctaccagc ggtacgaatc gctcacaagg aacatcgttc cattcatccg    1260

atcctctggc tccagccgcg tgatcgcctc cggcaagaaa ttcatcgagg gcttccagag    1320

caccaagctg aaggatcctc gtgcccagcc cggccaatcg tcgcccaaga tcgacgtggt    1380

catttccgag gccagctcat ccaacaacac tctcgaccca ggcacctgca ctgtcttcga    1440

agacagcgaa ttggccgata ccgtcgaagc caatttcacc gccacgttcg tcccctccat    1500

tcgtcaacgt ctggagaacg acctgtccgg tgtgactctc acagacacag aagtgaccta    1560

cctcatggac atgtgctcct tcgacaccat ctccaccagc accgtcgaca ccaagctgtc    1620

ccccttctgt gacctgttca cccatgacga atggatcaac tacgactacc tccagtcctt    1680

gaaaaagtat tacggccatg gtgcaggtaa cccgctcggc ccgacccagg gcgtcggcta    1740

cgctaacgag ctcatcgccc gtctgaccca ctcgcctgtc cacgatgaca ccagttccaa    1800

ccacactttg gactcgagcc cggctacctt tccgctcaac tctactctct acgcggactt    1860

ttcgcatgac aacggcatca tctccattct ctttgcttta ggtctgtaca acggcactaa    1920
```

-continued

```
gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                          2665
```

<210> SEQ ID NO 6
<211> LENGTH: 467
<212> TYPE: PRT
<213> ORGANISM: Aspergillus niger

<400> SEQUENCE: 6

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Pro Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240
```

-continued

```
Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 7
<211> LENGTH: 2665
<212> TYPE: DNA
<213> ORGANISM: Aspergillus niger

<400> SEQUENCE: 7

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780
```

-continued ctgaagctcg gactgtgtgg gactactgat cgctgactat ctgtgcagag tcacctccgg 840
actggcagtc cccgcctcga gaaatcaatc cagttgcgat acggtcgatc aggggtatca 900
atgcttctcc gagacttcgc atctttgggg tcaatacgca ccgttcttct ctctggcaaa 960
cgaatcggtc atctcccctg aggtgcccgc cggatgcaga gtcactttcg ctcaggtcct 1020
ctcccgtcat ggagcgcggt atccgaccga ctccaagggc aagaaatact ccgctctcat 1080
tgaggagatc cagcagaacg cgaccacctt tgacggaaaa tatgccttcc tgaagacata 1140
caactacagc ttgggtgcag atgacctgac tcccttcgga gaacaggagc tagtcaactc 1200
cggcatcaag ttctaccagc ggtacgaatc gctcacaagg aacatcgttc cattcatccg 1260
atcctctggc tccagccgcg tgatcgcctc cggcaagaaa ttcatcgagg gcttccagag 1320
caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcgaagc caatttcacc gccacgttcg tcccctccat 1500
tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620 cccccttctgt gacctgttca cccatgacga atggatcaac tacgactacc tccagtcctt 1680
ggaaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040
gccgctggtc cgtgtcttgg ttaatgatcg cgttgtcccg ctgcatgggt gtccggttga 2100
tgctttgggg agatgtaccc gggatagctt tgtgaggggg ttgagctttg ctagatctgg 2160
gggtgattgg gcggagtgtt ttgcttagct gaattacctt gatgaatggt atgtatcagc 2220
attgcatatc attagcactt caggtatgta ttatcgaaga tgtatatcga aaggatcaat 2280
ggtgactgtc actggttatc tgaatatccc tctatacctc gcccacaacc aatcatcacc 2340
ctttaaacaa tcacactcaa gccacagcgt acaaacgaac aaacgcacaa agaatatttt 2400
acactcctcc ccaacgcaat accaaccgca attcatcata cctcatataa atacaataca 2460
atacaataca tccatcccta ccctcaagtc cacccatcct ataatcaatc cctacttact 2520
tacttctccc cctcccctc acccttccca gaactcaccc ccgaagtagt aatagtagta 2580
gtagaagaag cagacgacct ctccaccaat ctcttcggcc tcttatcccc atacgctaca 2640
caaaaccccc accccgttag catgc 2665

<210> SEQ ID NO 8
<211> LENGTH: 467
<212> TYPE: PRT
<213> ORGANISM: Aspergillus niger

<400> SEQUENCE: 8

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp
20 25 30

-continued

Thr Val Asp Gln Gly Tyr Gln Cys Phe Ser Glu Thr Ser His Leu Trp
35 40 45

Gly Gln Tyr Ala Pro Phe Phe Ser Leu Ala Asn Glu Ser Val Ile Ser
50 55 60

Pro Glu Val Pro Ala Gly Cys Arg Val Thr Phe Ala Gln Val Leu Ser
65 70 75 80

Arg His Gly Ala Arg Tyr Pro Thr Asp Ser Lys Gly Lys Lys Tyr Ser
85 90 95

Ala Leu Ile Glu Glu Ile Gln Gln Asn Ala Thr Thr Phe Asp Gly Lys
100 105 110

Tyr Ala Phe Leu Lys Thr Tyr Asn Tyr Ser Leu Gly Ala Asp Asp Leu
115 120 125

Thr Pro Phe Gly Glu Gln Glu Leu Val Asn Ser Gly Ile Lys Phe Tyr
130 135 140

Gln Arg Tyr Glu Ser Leu Thr Arg Asn Ile Val Pro Phe Ile Arg Ser
145 150 155 160

Ser Gly Ser Ser Arg Val Ile Ala Ser Gly Lys Lys Phe Ile Glu Gly
165 170 175

Phe Gln Ser Thr Lys Leu Lys Asp Pro Arg Ala Gln Pro Gly Gln Ser
180 185 190

Ser Pro Lys Ile Asp Val Val Ile Ser Glu Ala Ser Ser Ser Asn Asn
195 200 205

Thr Leu Asp Pro Gly Thr Cys Thr Val Phe Glu Asp Ser Glu Leu Ala
210 215 220

Asp Thr Val Glu Ala Asn Phe Thr Ala Thr Phe Val Pro Ser Ile Arg
225 230 235 240

Gln Arg Leu Glu Asn Asp Leu Ser Gly Val Thr Leu Thr Asp Thr Glu
245 250 255

Val Thr Tyr Leu Met Asp Met Cys Ser Phe Asp Thr Ile Ser Thr Ser
260 265 270

Thr Val Asp Thr Lys Leu Ser Pro Phe Cys Asp Leu Phe Thr His Asp
275 280 285

Glu Trp Ile Asn Tyr Asp Tyr Leu Gln Ser Leu Glu Lys Tyr Tyr Gly
290 295 300

His Gly Ala Gly Asn Pro Leu Gly Pro Thr Gln Gly Val Gly Tyr Ala
305 310 315 320

Asn Glu Leu Ile Ala Arg Leu Thr His Ser Pro Val His Asp Asp Thr
325 330 335

Ser Ser Asn His Thr Leu Asp Ser Ser Pro Ala Thr Phe Pro Leu Asn
340 345 350

Ser Thr Leu Tyr Ala Asp Phe Ser His Asp Asn Gly Ile Ile Ser Ile
355 360 365

Leu Phe Ala Leu Gly Leu Tyr Asn Gly Thr Lys Pro Leu Ser Thr Thr
370 375 380

Thr Val Glu Asn Ile Thr Gln Thr Asp Gly Phe Ser Ser Ala Trp Thr
385 390 395 400

Val Pro Phe Ala Ser Arg Leu Tyr Val Glu Met Met Gln Cys Gln Ala
405 410 415

Glu Gln Glu Pro Leu Val Arg Val Leu Val Asn Asp Arg Val Val Pro
420 425 430

Leu His Gly Cys Pro Val Asp Ala Leu Gly Arg Cys Thr Arg Asp Ser
435 440 445

Phe Val Arg Gly Leu Ser Phe Ala Arg Ser Gly Gly Asp Trp Ala Glu

-continued

```
450                 455                 460

Cys Phe Ala
465


<210> SEQ ID NO 9
<211> LENGTH: 1455
<212> TYPE: DNA
<213> ORGANISM: Aspergillus fumigatus

<400> SEQUENCE: 9

atggtgactc tgactttcct gctttcggcg gcgtatctgc tttctgggtg agtggcttgg      60

atctattgct cggatagggc tgtggtgctg attctgaaac ggagtagagt gtctgcggca     120

cctagttctg ctggctccaa gtcctgcgat acggtagacc tcgggtacca gtgctcccct     180

gcgacttctc atctatgggg ccagtactcg ccattctttt cgctcgagga cgagctgtcc     240

gtgtcgagta agcttcccaa ggattgccgg atcaccttgg tacaggtgct atcgcgccat     300

ggagcgcggt acccaaccag ctccaagagc aaaaagtata agaagcttgt gacggcgatc     360

caggccaatg ccaccgactt caagggcaag tttgcctttt tgaagacgta caactatact     420

ctgggtgcgg atgacctcac tccctttggg gagcagcagc tggtgaactc gggcatcaag     480

ttctaccaga ggtacaaggc tctggcgcgc agtgtggtgc cgtttattcg cgcctcaggc     540

tcggaccggg ttattgcttc gggagagaag ttcatcgagg ggttccagca ggcgaagctg     600

gctgatcctg gcgcgacgaa ccgcgccgct ccggcgatta gtgtgattat tccggagagc     660

gagacgttca acaatacgct ggaccacggt gtgtgcacga agtttgaggc gagtcagctg     720

ggagatgagg ttgcggccaa tttcactgcg ctctttgcac ccgacatccg agctcgcgcc     780

gagaagcatc ttcctggcgt gacgctgaca gacgaggacg ttgtcagtct aatggacatg     840

tgttcgtttg atacggtagc gcgcaccagc gacgcaagtc agctgtcacc gttctgtcaa     900

ctcttcactc acaatgagtg gaagaagtac aactaccttc agtccttggg caagtactac     960

ggctacggcg caggcaaccc tctgggaccg gctcagggga tagggttcac caacgagctg    1020

attgcccggt tgactcgttc gccagtgcag gaccacacca gcactaactc gactctagtc    1080

tccaacccgg ccaccttccc gttgaacgct accatgtacg tcgacttttc acacgacaac    1140

agcctggttt ccatcttctt tgcattgggc ctgtacaacg gcactgaacc cttgtcccgg    1200

acctcggtgg aaagcgccaa ggaattggat gggtattctg catcctgggt ggtgcctttc    1260

ggcgcgcgag cctacttcga gacgatgcaa tgcaagtcgg aaaaggagcc tcttgttcgc    1320

gctttgatta atgaccgggt tgtgccactg catggctgcg atgtggacaa gctggggcga    1380

tgcaagctga atgactttgt caagggattg agttgggcca gatctggggg caactgggga    1440

gagtgcttta gttga                                                     1455


<210> SEQ ID NO 10
<211> LENGTH: 465
<212> TYPE: PRT
<213> ORGANISM: Aspergillus fumigatus

<400> SEQUENCE: 10

Met Val Thr Leu Thr Phe Leu Leu Ser Ala Ala Tyr Leu Leu Ser Gly
  1               5                  10                  15

Arg Val Ser Ala Ala Pro Ser Ser Ala Gly Ser Lys Ser Cys Asp Thr
             20                  25                  30

Val Asp Leu Gly Tyr Gln Cys Ser Pro Ala Thr Ser His Leu Trp Gly
         35                  40                  45
```

-continued

```
Gln Tyr Ser Pro Phe Phe Ser Leu Glu Asp Glu Leu Ser Val Ser Ser
     50                  55                  60

Lys Leu Pro Lys Asp Cys Arg Ile Thr Leu Val Gln Val Leu Ser Arg
 65                  70                  75                  80

His Gly Ala Arg Tyr Pro Thr Ser Ser Lys Ser Lys Lys Tyr Lys Lys
                 85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Leu Val Ser Ile Phe Phe
        355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
        435                 440                 445

Lys Gly Leu Ser Trp Ala Arg Ser Gly Gly Asn Trp Gly Glu Cys Phe
    450                 455                 460
```

-continued

Ser
465

<210> SEQ ID NO 11
<211> LENGTH: 2665
<212> TYPE: DNA
<213> ORGANISM: Aspergillus niger

<400> SEQUENCE: 11
gcatgcagca ctgtcagcaa ataaattgct ttgaatgatt ttctgcttct tctcatattg 60
ggctatagac actgccgtta tctgactttt aatgagcgag ggcgatgttc atcattcggc 120
gttctgttct tatgatttcc ccacgtcctt tcgggctttc ggcacagcaa aatagattgt 180
ttagcaggta cagaaacaac ttgatgacac atgcatccga gaatcttcag ccgtggaagc 240
attcatgtag atctttgcta agagaaatga tggcggccca gggcatccag gcaccttttc 300
caacggggaa cttccgccgt ccacgtgctc tgattcagcc aatcaagacg tcccacggca 360
atgctggatc aacgatcaac ttgaatgcaa taaatgaaga tggaactaac accatctgct 420
gcctttctct cgagaaagct cctccacttc tcccactaga tatctccgtc cccgtcgact 480
tcccgtccta ttcggcctcg tccgctgaag atccatccca ccattgcacg tgggccacct 540
ttgtgagctt ctaacctgaa ctggtagagt atcacacacc atgccaaggt gggatgaagg 600
ggttatatag gaccgtccgg tccggcgcga tggccgtagc tgccactcgc tgctgtgcaa 660
gaaattactt ctcataggca tcatgggcgt ctctgctgtt ctacttcctt tgtatctcct 720
gtctgggtat gctaagcacc acaatcaaag tctaataagg accctccctt ccgagggccc 780
ctgaagctcg gactgtgtgg gactactgat cgctgactat ctgtgcagag tcacctccgg 840
actggcagtc cccgcctcga gaaatcaatc cagttgcgat acggtcgatc aggggtatca 900
atgcttctcc gagacttcgc atctttgggg tctatacgca ccgttcttct ctctggcaaa 960
cgaatcggtc atctcccctg aggtgcccgc cggatgcaga gtcactttcg ctcaggtcct 1020
ctcccgtcat ggagcgcggt atccgaccga ctccaagggc aagaaatact ccgctctcat 1080
tgaggagatc cagcagaacg cgaccacctt tgacggaaaa tatgccttcc tgaagacata 1140
caactacagc ttgggtgcag atgacctgac tcccttcgga gaacaggagc tagtcaactc 1200
cggcatcaag ttctaccagc ggtacgaatc gctcacaagg aacatcgttc cattcatccg 1260
atcctctggc tccagccgcg tgatcgcctc cggcaagaaa ttcatcgagg gcttccagag 1320
caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcgaagc caatttcacc gccacgttcg tccctccat 1500 tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620
ccccttctgt gacctgttca cccatgacga atggatcaac tacgactacc tccagtcctt 1680
gaaaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040

-continued

```
gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                           2665


<210> SEQ ID NO 12
<211> LENGTH: 467
<212> TYPE: PRT
<213> ORGANISM: Aspergillus niger

<400> SEQUENCE: 12

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Leu Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
```

-continued

```
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 13
<211> LENGTH: 1401
<212> TYPE: DNA
<213> ORGANISM: Aspergillus terreus

<400> SEQUENCE: 13

```
atgggggttt tcgtcgttct attatctatc gcgactctgt tcggcagcac atcgggcact      60

gcgctgggcc cccgtggaaa tcacagcgac tgcacctcag tcgaccgggg gtatcaatgc     120

ttccctgagc tctcccataa atggggtctc tacgcgccct atttctccct ccaggatgaa     180

tctccgtttc ctctggacgt cccggatgac tgccacatca cctttgtgca ggtgctggcc     240

cgacatggag cgcggtctcc aaccgatagc aagacaaagg cgtatgccgc gactattgca     300

gccatccaga agaatgccac cgcgttgccg ggcaaatacg ccttcctgaa gtcgtacaat     360

tactccatgg gctccgagaa cctgaacccc ttcgggcgga accaactgca agatctgggc     420

gcccagttct accgtcgcta cgacaccctc acccggcaca tcaacccttt cgtccgggcc     480

gcggattcct cccgcgtcca cgaatcagcc gagaagttcg tcgagggctt ccaaaacgcc     540

cgccaaggcg atcctcacgc caaccctcac cagccgtcgc cgcgcgtgga tgtagtcatc     600

cccgaaggca ccgcctacaa caacacgctc gagcacagca tctgcaccgc cttcgaggcc     660

agcaccgtcg gcgacgccgc ggcagacaac ttcactgccg tgttcgcgcc ggcgatcgcc     720

aagcgtctgg aggccgatct gcccggcgtg cagctgtccg ccgacgacgt ggtcaatctg     780

atggccatgt gtccgttcga gacggtcagc ctgaccgacg acgcgcacac gctgtcgccg     840

ttctgcgacc tcttcaccgc cgccgagtgg acgcagtaca actacctgct ctcgctggac     900
```

-continued

```
aagtactacg gctacggcgg cggcaatccg ctgggccccg tgcagggcgt gggctgggcg     960

aacgagctga tcgcgcggct gacgcgctcc cccgtccacg accacacctg cgtcaacaac    1020

accctcgacg ccaacccggc caccttcccg ctgaacgcca ccctctacgc ggacttttcg    1080

cacgacagta acctggtgtc gatcttctgg gcgctgggtc tgtacaacgg caccaagccc    1140

ctgtcgcaga ccaccgtgga ggatatcacc cggacggacg ggtacgcggc cgcctggacg    1200

gtgccgtttg ccgcccgcgc ctacatcgag atgatgcagt gtcgcgcgga gaagcagccg    1260

ctggtgcgcg tgctggtcaa cgaccgtgtc atgccgctgc acggctgcgc ggtggataat    1320

ctgggcaggt gtaaacggga cgactttgtg gagggactga gctttgcgcg ggcaggaggg    1380

aactgggccg agtgtttctg a                                              1401
```

<210> SEQ ID NO 14
<211> LENGTH: 466
<212> TYPE: PRT
<213> ORGANISM: Aspergillus terreus

<400> SEQUENCE: 14

```
Met Gly Val Phe Val Val Leu Leu Ser Ile Ala Thr Leu Phe Gly Ser
  1               5                  10                  15

Thr Ser Gly Thr Ala Leu Gly Pro Arg Gly Asn His Ser Asp Cys Thr
             20                  25                  30

Ser Val Asp Arg Gly Tyr Gln Cys Phe Pro Glu Leu Ser His Lys Trp
         35                  40                  45

Gly Leu Tyr Ala Pro Tyr Phe Ser Leu Gln Asp Glu Ser Pro Phe Pro
     50                  55                  60

Leu Asp Val Pro Asp Asp Cys His Ile Thr Phe Val Gln Val Leu Ala
 65                  70                  75                  80

Arg His Gly Ala Arg Ser Pro Thr Asp Ser Lys Thr Lys Ala Tyr Ala
                 85                  90                  95

Ala Thr Ile Ala Ala Ile Gln Lys Asn Ala Thr Ala Leu Pro Gly Lys
            100                 105                 110

Tyr Ala Phe Leu Lys Ser Tyr Asn Tyr Ser Met Gly Ser Glu Asn Leu
        115                 120                 125

Asn Pro Phe Gly Arg Asn Gln Leu Gln Asp Leu Gly Ala Gln Phe Tyr
    130                 135                 140

Arg Arg Tyr Asp Thr Leu Thr Arg His Ile Asn Pro Phe Val Arg Ala
145                 150                 155                 160

Ala Asp Ser Ser Arg Val His Glu Ser Ala Glu Lys Phe Val Glu Gly
                165                 170                 175

Phe Gln Asn Ala Arg Gln Gly Asp Pro His Ala Asn Pro His Gln Pro
            180                 185                 190

Ser Pro Arg Val Asp Val Val Ile Pro Glu Gly Thr Ala Tyr Asn Asn
        195                 200                 205

Thr Leu Glu His Ser Ile Cys Thr Ala Phe Glu Ala Ser Thr Val Gly
    210                 215                 220

Asp Ala Ala Ala Asp Asn Phe Thr Ala Val Phe Ala Pro Ala Ile Ala
225                 230                 235                 240

Lys Arg Leu Glu Ala Asp Leu Pro Gly Val Gln Leu Ser Ala Asp Asp
                245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Ala
        275                 280                 285
```

-continued

```
Glu Trp Thr Gln Tyr Asn Tyr Leu Leu Ser Leu Asp Lys Tyr Tyr Gly
    290                 295                 300

Tyr Gly Gly Gly Asn Pro Leu Gly Pro Val Gln Gly Val Gly Trp Ala
305                 310                 315                 320

Asn Glu Leu Ile Ala Arg Leu Thr Arg Ser Pro Val His Asp His Thr
                325                 330                 335

Cys Val Asn Asn Thr Leu Asp Ala Asn Pro Ala Thr Phe Pro Leu Asn
            340                 345                 350

Ala Thr Leu Tyr Ala Asp Phe Ser His Asp Ser Asn Leu Val Ser Ile
        355                 360                 365

Phe Trp Ala Leu Gly Leu Tyr Asn Gly Thr Lys Pro Leu Ser Gln Thr
    370                 375                 380

Thr Val Glu Asp Ile Thr Arg Thr Asp Gly Tyr Ala Ala Ala Trp Thr
385                 390                 395                 400

Val Pro Phe Ala Ala Arg Ala Tyr Ile Glu Met Met Gln Cys Arg Ala
                405                 410                 415

Glu Lys Gln Pro Leu Val Arg Val Leu Val Asn Asp Arg Val Met Pro
            420                 425                 430

Leu His Gly Cys Ala Val Asp Asn Leu Gly Arg Cys Lys Arg Asp Asp
        435                 440                 445

Phe Val Glu Gly Leu Ser Phe Ala Arg Ala Gly Gly Asn Trp Ala Glu
    450                 455                 460

Cys Phe
465


<210> SEQ ID NO 15
<211> LENGTH: 2665
<212> TYPE: DNA
<213> ORGANISM: Aspergillus niger

<400> SEQUENCE: 15

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780

ctgaagctcg gactgtgtgg gactactgat cgctgactat ctgtgcagag tcacctccgg     840

actggcagtc cccgcctcga gaaatcaatc cagttgcgat acggtcgatc aggggtatca     900

atgcttctcc gagacttcgc atctttgggg tcaatacgca ccgttcttct ctctggcaaa     960

cgaatcggtc atctcccctg aggtgcccgc cggatgcaga gtcactttcg ctcaggtcct    1020
```

-continued

```
ctcccgtcat ggagcgcggt atccgaccga ctccgcgggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcgaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacgactacc tccagtcctt   1680

gaaaaagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

<210> SEQ ID NO 16
<211> LENGTH: 467
<212> TYPE: PRT
<213> ORGANISM: Aspergillus niger

<400> SEQUENCE: 16

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80
```

-continued

Arg His Gly Ala Arg Tyr Pro Thr Asp Ser Ala Gly Lys Lys Tyr Ser
85 90 95

Ala Leu Ile Glu Glu Ile Gln Gln Asn Ala Thr Thr Phe Asp Gly Lys
100 105 110

Tyr Ala Phe Leu Lys Thr Tyr Asn Tyr Ser Leu Gly Ala Asp Asp Leu
115 120 125

Thr Pro Phe Gly Glu Gln Glu Leu Val Asn Ser Gly Ile Lys Phe Tyr
130 135 140

Gln Arg Tyr Glu Ser Leu Thr Arg Asn Ile Val Pro Phe Ile Arg Ser
145 150 155 160

Ser Gly Ser Ser Arg Val Ile Ala Ser Gly Lys Lys Phe Ile Glu Gly
165 170 175

Phe Gln Ser Thr Lys Leu Lys Asp Pro Arg Ala Gln Pro Gly Gln Ser
180 185 190

Ser Pro Lys Ile Asp Val Val Ile Ser Glu Ala Ser Ser Ser Asn Asn
195 200 205

Thr Leu Asp Pro Gly Thr Cys Thr Val Phe Glu Asp Ser Glu Leu Ala
210 215 220

Asp Thr Val Glu Ala Asn Phe Thr Ala Thr Phe Val Pro Ser Ile Arg
225 230 235 240

Gln Arg Leu Glu Asn Asp Leu Ser Gly Val Thr Leu Thr Asp Thr Glu
245 250 255

Val Thr Tyr Leu Met Asp Met Cys Ser Phe Asp Thr Ile Ser Thr Ser
260 265 270

Thr Val Asp Thr Lys Leu Ser Pro Phe Cys Asp Leu Phe Thr His Asp
275 280 285

Glu Trp Ile Asn Tyr Asp Tyr Leu Gln Ser Leu Lys Lys Tyr Tyr Gly
290 295 300

His Gly Ala Gly Asn Pro Leu Gly Pro Thr Gln Gly Val Gly Tyr Ala
305 310 315 320

Asn Glu Leu Ile Ala Arg Leu Thr His Ser Pro Val His Asp Asp Thr
325 330 335

Ser Ser Asn His Thr Leu Asp Ser Ser Pro Ala Thr Phe Pro Leu Asn
340 345 350

Ser Thr Leu Tyr Ala Asp Phe Ser His Asp Asn Gly Ile Ile Ser Ile
355 360 365

Leu Phe Ala Leu Gly Leu Tyr Asn Gly Thr Lys Pro Leu Ser Thr Thr
370 375 380

Thr Val Glu Asn Ile Thr Gln Thr Asp Gly Phe Ser Ser Ala Trp Thr
385 390 395 400

Val Pro Phe Ala Ser Arg Leu Tyr Val Glu Met Met Gln Cys Gln Ala
405 410 415

Glu Gln Glu Pro Leu Val Arg Val Leu Val Asn Asp Arg Val Val Pro
420 425 430

Leu His Gly Cys Pro Val Asp Ala Leu Gly Arg Cys Thr Arg Asp Ser
435 440 445

Phe Val Arg Gly Leu Ser Phe Ala Arg Ser Gly Gly Asp Trp Ala Glu
450 455 460

Cys Phe Ala
465

<210> SEQ ID NO 17
<211> LENGTH: 2665
<212> TYPE: DNA

-continued

<213> ORGANISM: Aspergillus niger

<400> SEQUENCE: 17
gcatgcagca ctgtcagcaa ataaattgct ttgaatgatt ttctgcttct tctcatattg 60
ggctatagac actgccgtta tctgactttt aatgagcgag ggcgatgttc atcattcggc 120
gttctgttct tatgatttcc ccacgtcctt tcgggctttc ggcacagcaa aatagattgt 180
ttagcaggta cagaaacaac ttgatgacac atgcatccga gaatcttcag ccgtggaagc 240
attcatgtag atctttgcta agagaaatga tggcggccca gggcatccag gcaccttttc 300
caacggggaa cttccgccgt ccacgtgctc tgattcagcc aatcaagacg tcccacggca 360
atgctggatc aacgatcaac ttgaatgcaa taaatgaaga tggaactaac accatctgct 420
gcctttctct cgagaaagct cctccacttc tcccactaga tatctccgtc cccgtcgact 480
tcccgtccta ttcggcctcg tccgctgaag atccatccca ccattgcacg tgggccacct 540
ttgtgagctt ctaacctgaa ctggtagagt atcacacacc atgccaaggt gggatgaagg 600
ggttatatag gaccgtccgg tccggcgcga tggccgtagc tgccactcgc tgctgtgcaa 660
gaaattactt ctcataggca tcatgggcgt ctctgctgtt ctacttcctt tgtatctcct 720
gtctgggtat gctaagcacc acaatcaaag tctaataagg accctccctt ccgagggccc 780
ctgaagctcg gactgtgtgg gactactgat cgctgactat ctgtgcagag tcacctccgg 840
actggcagtc cccgcctcga gaaatcaatc cagttgcgat acggtcgatc aggggtatca 900
atgcttctcc gagacttcgc atctttgggg tcaatacgca ccgttcttct ctctggcaaa 960
cgaatcggtc atctcccctg aggtgcccgc cggatgcaga gtcactttcg ctcaggtcct 1020
ctcccgtcat ggagcgcggt atccgaccga ctccgagggc aagaaatact ccgctctcat 1080
tgaggagatc cagcagaacg cgaccacctt tgacggaaaa tatgccttcc tgaagacata 1140
caactacagc ttgggtgcag atgacctgac tcccttcgga gaacaggagc tagtcaactc 1200
cggcatcaag ttctaccagc ggtacgaatc gctcacaagg aacatcgttc cattcatccg 1260
atcctctggc tccagccgcg tgatcgcctc cggcaagaaa ttcatcgagg gcttccagag 1320
caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcgaagc caatttcacc gccacgttcg tcccctccat 1500
tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620
ccccttctgt gacctgttca cccatgacga atggatcaac tacgactacc tccagtcctt 1680
gaaaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040
gccgctggtc cgtgtcttgg ttaatgatcg cgttgtcccg ctgcatgggt gtccggttga 2100
tgctttgggg agatgtaccc gggatagctt tgtgaggggg ttgagctttg ctagatctgg 2160
gggtgattgg gcggagtgtt ttgcttagct gaattacctt gatgaatggt atgtatcagc 2220
attgcatatc attagcactt caggtatgta ttatcgaaga tgtatatcga aaggatcaat 2280

-continued

```
ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

```
<210> SEQ ID NO 18
<211> LENGTH: 467
<212> TYPE: PRT
<213> ORGANISM: Aspergillus niger

<400> SEQUENCE: 18

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Glu Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300
```

-continued

```
His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 19
<211> LENGTH: 2665
<212> TYPE: DNA
<213> ORGANISM: Aspergillus niger

<400> SEQUENCE: 19

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780

ctgaagctcg gactgtgtgg gactactgat cgctgactat ctgtgcagag tcacctccgg     840

actggcagtc cccgcctcga gaaatcaatc cagttgcgat acggtcgatc aggggtatca     900

atgcttctcc gagacttcgc atctttgggg tcaatacgca ccgttcttct ctctggcaaa     960

cgaatcggtc atctcccctg aggtgcccgc cggatgcaga gtcactttcg ctcaggtcct    1020

ctcccgtcat ggagcgcggt atccgaccga ctccaagggc aaggaatact ccgctctcat    1080

tgaggagatc cagcagaacg cgaccacctt tgacggaaaa tatgccttcc tgaagacata    1140
```

-continued

```
caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcgaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacgactacc tccagtcctt   1680

gaaaaagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctcccctc  acccttccca gaactcaccc ccgaagtagt aatagtagta   2580

gtagaagaag cagacgacct ctccaccaat ctcttcggcc tcttatcccc atacgctaca   2640

caaaacccc  accccgttag catgc                                          2665
```

```
<210> SEQ ID NO 20
<211> LENGTH: 467
<212> TYPE: PRT
<213> ORGANISM: Aspergillus niger

<400> SEQUENCE: 20

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Glu Tyr Ser
                 85                  90                  95
```

-continued

```
Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 21
<211> LENGTH: 2665
<212> TYPE: DNA
<213> ORGANISM: Aspergillus niger

<400> SEQUENCE: 21

-continued

```
gcatgcagca ctgtcagcaa ataaattgct ttgaatgatt ttctgcttct tctcatattg      60
ggctatagac actgccgtta tctgactttt aatgagcgag ggcgatgttc atcattcggc     120
gttctgttct tatgatttcc ccacgtcctt tcgggctttc ggcacagcaa aatagattgt     180
ttagcaggta cagaaacaac ttgatgacac atgcatccga gaatcttcag ccgtggaagc     240
attcatgtag atctttgcta agagaaatga tggcggccca gggcatccag gcaccttttc     300
caacggggaa cttccgccgt ccacgtgctc tgattcagcc aatcaagacg tcccacggca     360
atgctggatc aacgatcaac ttgaatgcaa taaatgaaga tggaactaac accatctgct     420
gcctttctct cgagaaagct cctccacttc tcccactaga tatctccgtc cccgtcgact     480
tcccgtccta ttcggcctcg tccgctgaag atccatccca ccattgcacg tgggccacct     540
ttgtgagctt ctaacctgaa ctggtagagt atcacacacc atgccaaggt gggatgaagg     600
ggttatatag gaccgtccgg tccggcgcga tggccgtagc tgccactcgc tgctgtgcaa     660
gaaattactt ctcataggca tcatgggcgt ctctgctgtt ctacttcctt tgtatctcct     720
gtctgggtat gctaagcacc acaatcaaag tctaataagg accctccctt ccgagggccc     780
ctgaagctcg gactgtgtgg gactactgat cgctgactat ctgtgcagag tcacctccgg     840
actggcagtc cccgcctcga gaaatcaatc cagttgcgat acggtcgatc aggggtatca     900
atgcttctcc gagacttcgc atctttgggg tcaatacgca ccgttcttct ctctggcaaa     960
cgaatcggtc atctcccctg aggtgcccgc cggatgcaga gtcactttcg ctcaggtcct    1020
ctcccgtcat ggagcgcggt atccgaccga ctccaagggc aagaaatact ccgctctcat    1080
tgaggagatc cagcagaacg cgaccacctt tgacggaaaa tatgccttcc tgaagacata    1140
caactacagc ttgggtgcag atgacctgac tcccttcgga gaacaggagc tagtcaactc    1200
cggcatcaag ttctaccagc ggtacgaatc gctcacaagg aacatcgttc cattcatccg    1260
atcctctggc tccagccgcg tgatcgcctc cggcaagaaa ttcatcgagg gcttccagag    1320
caccaagctg aaggatcctc gtgcccagcc cggccaatcg tcgcccaaga tcgacgtggt    1380
catttccgag gccagctcat ccaacaacac tctcgaccca ggcacctgca ctgtcttcga    1440
agacagcgaa ttggccgata ccgtccaagc caatttcacc gccacgttcg tcccctccat    1500
tcgtcaacgt ctggagaacg acctgtccgg tgtgactctc acagacacag aagtgaccta    1560
cctcatggac atgtgctcct tcgacaccat ctccaccagc accgtcgaca ccaagctgtc    1620
ccccttctgt gacctgttca cccatgacga atggatcaac tacgactacc tccagtcctt    1680
gaaaaagtat tacggccatg gtgcaggtaa cccgctcggc ccgacccagg gcgtcggcta    1740
cgctaacgag ctcatcgccc gtctgaccca ctcgcctgtc cacgatgaca ccagttccaa    1800
ccacactttg gactcgagcc cggctacctt tccgctcaac tctactctct acgcggactt    1860
ttcgcatgac aacggcatca tctccattct ctttgcttta ggtctgtaca acggcactaa    1920
gccgctatct accacgaccg tggagaatat cacccagaca gatggattct cgtctgcttg    1980
gacggttccg tttgcttcgc gtttgtacgt cgagatgatg cagtgtcagg cggagcagga    2040
gccgctggtc cgtgtcttgg ttaatgatcg cgttgtcccg ctgcatgggt gtccggttga    2100
tgctttgggg agatgtaccc gggatagctt tgtgaggggg ttgagctttg ctagatctgg    2160
gggtgattgg gcggagtgtt ttgcttagct gaattacctt gatgaatggt atgtatcagc    2220
attgcatatc attagcactt caggtatgta ttatcgaaga tgtatatcga aaggatcaat    2280
ggtgactgtc actggttatc tgaatatccc tctatacctc gcccacaacc aatcatcacc    2340
```

```
ctttaaacaa tcacactcaa gccacagcgt acaaacgaac aaacgcacaa agaatatttt    2400

acactcctcc ccaacgcaat accaaccgca attcatcata cctcatataa atacaataca    2460

atacaataca tccatcccta ccctcaagtc cacccatcct ataatcaatc cctacttact    2520

tacttctccc cctcccccct cacccttccca gaactcaccc ccgaagtagt aatagtagta    2580

gtagaagaag cagacgacct ctccaccaat ctcttcggcc tcttatcccc atacgctaca    2640

caaaaccccc accccgttag catgc                                         2665
```

<210> SEQ ID NO 22
<211> LENGTH: 467
<212> TYPE: PRT
<213> ORGANISM: Aspergillus niger

<400> SEQUENCE: 22

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Gln Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320
```

-continued

```
Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 23
<211> LENGTH: 2665
<212> TYPE: DNA
<213> ORGANISM: Aspergillus niger

<400> SEQUENCE: 23

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780

ctgaagctcg gactgtgtgg gactactgat cgctgactat ctgtgcagag tcacctccgg     840

actggcagtc cccgcctcga gaaatcaatc cagttgcgat acggtcgatc aggggtatca     900

atgcttctcc gagacttcgc atctttgggg tcaatacgca ccgttcttct ctctggcaaa     960

cgaatcggtc atctcccctg aggtgcccgc cggatgcaga gtcactttcg ctcaggtcct    1020

ctcccgtcat ggagcgcggt atccgaccga ctccaagggc aagaaatact ccgctctcat    1080

tgaggagatc cagcagaacg cgaccacctt tgacggaaaa tatgccttcc tgaagacata    1140

caactacagc ttgggtgcag atgacctgac tcccttcgga gaacaggagc tagtcaactc    1200
```

-continued cggcatcaag ttctaccagc ggtacgaatc gctcacaagg aacatcgttc cattcatccg 1260
atcctctggc tccagccgcg tgatcgcctc cggcaagaaa ttcatcgagg gcttccagag 1320
caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcaaagc caatttcacc gccacgttcg tcccctccat 1500
tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620 cccctctgt gacctgttca cccatgacga atggatcaac tacgactacc tccagtcctt 1680
gaaaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040
gccgctggtc cgtgtcttgg ttaatgatcg cgttgtcccg ctgcatgggt gtccggttga 2100
tgctttgggg agatgtaccc gggatagctt tgtgaggggg ttgagctttg ctagatctgg 2160
gggtgattgg gcggagtgtt ttgcttagct gaattacctt gatgaatggt atgtatcagc 2220
attgcatatc attagcactt caggtatgta ttatcgaaga tgtatatcga aaggatcaat 2280
ggtgactgtc actggttatc tgaatatccc tctatacctc gcccacaacc aatcatcacc 2340
ctttaaacaa tcacactcaa gccacagcgt acaaacgaac aaacgcacaa agaatatttt 2400
acactcctcc ccaacgcaat accaaccgca attcatcata cctcatataa atacaataca 2460
atacaataca tccatcccta ccctcaagtc cacccatcct ataatcaatc cctacttact 2520
tacttctccc cctccccctc acccttccca gaactcaccc ccgaagtagt aatagtagta 2580
gtagaagaag cagacgacct ctccaccaat ctcttcggcc tcttatcccc atacgctaca 2640
caaaaccccc accccgttag catgc 2665

<210> SEQ ID NO 24
<211> LENGTH: 467
<212> TYPE: PRT
<213> ORGANISM: Aspergillus niger

<400> SEQUENCE: 24

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp
20 25 30

Thr Val Asp Gln Gly Tyr Gln Cys Phe Ser Glu Thr Ser His Leu Trp
35 40 45

Gly Gln Tyr Ala Pro Phe Phe Ser Leu Ala Asn Glu Ser Val Ile Ser
50 55 60

Pro Glu Val Pro Ala Gly Cys Arg Val Thr Phe Ala Gln Val Leu Ser
65 70 75 80

Arg His Gly Ala Arg Tyr Pro Thr Asp Ser Lys Gly Lys Lys Tyr Ser
85 90 95

Ala Leu Ile Glu Glu Ile Gln Gln Asn Ala Thr Thr Phe Asp Gly Lys
100 105 110

-continued

```
Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 25
<211> LENGTH: 2665
<212> TYPE: DNA
<213> ORGANISM: Aspergillus niger

<400> SEQUENCE: 25

gcatgcagca ctgtcagcaa ataaattgct ttgaatgatt ttctgcttct tctcatattg      60
```

-continued

```
ggctatagac actgccgtta tctgactttt aatgagcgag ggcgatgttc atcattcggc    120
gttctgttct tatgatttcc ccacgtcctt tcgggctttc ggcacagcaa aatagattgt    180
ttagcaggta cagaaacaac ttgatgacac atgcatccga gaatcttcag ccgtggaagc    240
attcatgtag atctttgcta agagaaatga tggcggccca gggcatccag gcaccttttc    300
caacggggaa cttccgccgt ccacgtgctc tgattcagcc aatcaagacg tcccacggca    360
atgctggatc aacgatcaac ttgaatgcaa taaatgaaga tggaactaac accatctgct    420
gcctttctct cgagaaagct cctccacttc tcccactaga tatctccgtc cccgtcgact    480
tcccgtccta ttcggcctcg tccgctgaag atccatccca ccattgcacg tgggccacct    540
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcgaagc caatttcacc gccacgttcg tcccctccat   1500
tcgtcaacgt ctggagaacg acctgtccgg tgtgactctc acagacacag aagtgaccta   1560
cctcatgcac atgtgctcct tcgacaccat ctccaccagc accgtcgaca ccaagctgtc   1620
cccccttctgt gacctgttca cccatgacga atggatcaac tacgactacc tccagtcctt   1680
gaaaaagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
```

-continued

```
atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                          2665


<210> SEQ ID NO 26
<211> LENGTH: 467
<212> TYPE: PRT
<213> ORGANISM: Aspergillus niger

<400> SEQUENCE: 26

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met His Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335
```

-continued

```
Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 27
<211> LENGTH: 2665
<212> TYPE: DNA
<213> ORGANISM: Aspergillus niger

<400> SEQUENCE: 27

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320
```

-continued caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcgaagc caatttcacc gccacgttcg tcccctccat 1500
tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620
ccccttctgt gacctgttca cccatgacga atggatcaac tacgactacc tccagtcctt 1680
gagaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040
gccgctggtc cgtgtcttgg ttaatgatcg cgttgtcccg ctgcatgggt gtccggttga 2100
tgctttgggg agatgtaccc gggatagctt tgtgaggggg ttgagctttg ctagatctgg 2160
gggtgattgg gcggagtgtt ttgcttagct gaattacctt gatgaatggt atgtatcagc 2220
attgcatatc attagcactt caggtatgta ttatcgaaga tgtatatcga aaggatcaat 2280
ggtgactgtc actggttatc tgaatatccc tctatacctc gcccacaacc aatcatcacc 2340
ctttaaacaa tcacactcaa gccacagcgt acaaacgaac aaacgcacaa agaatatttt 2400
acactcctcc ccaacgcaat accaaccgca attcatcata cctcatataa atacaataca 2460
atacaataca tccatcccta ccctcaagtc cacccatcct ataatcaatc cctacttact 2520
tacttctccc cctccccctc acccttccca gaactcaccc ccgaagtagt aatagtagta 2580
gtagaagaag cagacgacct ctccaccaat ctcttcggcc tcttatcccc atacgctaca 2640
caaaaccccc accccgttag catgc 2665

<210> SEQ ID NO 28
<211> LENGTH: 467
<212> TYPE: PRT
<213> ORGANISM: Aspergillus niger

<400> SEQUENCE: 28

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp
20 25 30

Thr Val Asp Gln Gly Tyr Gln Cys Phe Ser Glu Thr Ser His Leu Trp
35 40 45

Gly Gln Tyr Ala Pro Phe Phe Ser Leu Ala Asn Glu Ser Val Ile Ser
50 55 60

Pro Glu Val Pro Ala Gly Cys Arg Val Thr Phe Ala Gln Val Leu Ser
65 70 75 80

Arg His Gly Ala Arg Tyr Pro Thr Asp Ser Lys Gly Lys Lys Tyr Ser
85 90 95

Ala Leu Ile Glu Glu Ile Gln Gln Asn Ala Thr Thr Phe Asp Gly Lys
100 105 110

Tyr Ala Phe Leu Lys Thr Tyr Asn Tyr Ser Leu Gly Ala Asp Asp Leu
115 120 125

-continued

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Arg Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465

<210> SEQ ID NO 29
<211> LENGTH: 2665
<212> TYPE: DNA
<213> ORGANISM: Aspergillus niger

<400> SEQUENCE: 29
gcatgcagca ctgtcagcaa ataaattgct ttgaatgatt ttctgcttct tctcatattg 60
ggctatagac actgccgtta tctgactttt aatgagcgag ggcgatgttc atcattcggc 120
gttctgttct tatgatttcc ccacgtcctt tcgggctttc ggcacagcaa aatagattgt 180

-continued

```
ttagcaggta cagaaacaac ttgatgacac atgcatccga gaatcttcag ccgtggaagc    240
attcatgtag atctttgcta agagaaatga tggcggccca gggcatccag gcaccttttc    300
caacggggaa cttccgccgt ccacgtgctc tgattcagcc aatcaagacg tcccacggca    360
atgctggatc aacgatcaac ttgaatgcaa taaatgaaga tggaactaac accatctgct    420
gcctttctct cgagaaagct cctccacttc tcccactaga tatctccgtc cccgtcgact    480
tcccgtccta ttcggcctcg tccgctgaag atccatccca ccattgcacg tgggccacct    540
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcgaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
cccctctgt gacctgttca cccatgacga atggatcaac tacgactacc tccagtcctt   1680
gacaaagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
```

```
tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaacccc accccgttag catgc                                          2665


<210> SEQ ID NO 30
<211> LENGTH: 467
<212> TYPE: PRT
<213> ORGANISM: Aspergillus niger

<400> SEQUENCE: 30

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Thr Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350
```

-continued

```
Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 31
<211> LENGTH: 2665
<212> TYPE: DNA
<213> ORGANISM: Aspergillus niger

<400> SEQUENCE: 31

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380
```

-continued

```
catttccgag gccagctcat ccaacaacac tctcgaccca ggcacctgca ctgtcttcga   1440

agacagcgaa ttggccgata ccgtcgaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacgactacc tccagtcctt   1680

ggataagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

```
<210> SEQ ID NO 32
<211> LENGTH: 467
<212> TYPE: PRT
<213> ORGANISM: Aspergillus niger

<400> SEQUENCE: 32

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140
```

-continued

```
Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Asp Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 33
<211> LENGTH: 2665
<212> TYPE: DNA
<213> ORGANISM: Aspergillus niger

<400> SEQUENCE: 33

```
gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240
```

-continued

```
attcatgtag atctttgcta agagaaatga tggcggccca gggcatccag gcaccttttc    300
caacggggaa cttccgccgt ccacgtgctc tgattcagcc aatcaagacg tcccacggca    360
atgctggatc aacgatcaac ttgaatgcaa taaatgaaga tggaactaac accatctgct    420
gcctttctct cgagaaagct cctccacttc tcccactaga tatctccgtc cccgtcgact    480
tcccgtccta ttcggcctcg tccgctgaag atccatccca ccattgcacg tgggccacct    540
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcgaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
ccccttctgt gacctgttca cccatgacga atggatcaac tacgactacc tccagtcctt   1680
gaaagagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
```

-continued caaaacccccc accccgttag catgc 2665

<210> SEQ ID NO 34
<211> LENGTH: 467
<212> TYPE: PRT
<213> ORGANISM: Aspergillus niger

<400> SEQUENCE: 34

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp
20 25 30

Thr Val Asp Gln Gly Tyr Gln Cys Phe Ser Glu Thr Ser His Leu Trp
35 40 45

Gly Gln Tyr Ala Pro Phe Phe Ser Leu Ala Asn Glu Ser Val Ile Ser
50 55 60

Pro Glu Val Pro Ala Gly Cys Arg Val Thr Phe Ala Gln Val Leu Ser
65 70 75 80

Arg His Gly Ala Arg Tyr Pro Thr Asp Ser Lys Gly Lys Lys Tyr Ser
85 90 95

Ala Leu Ile Glu Glu Ile Gln Gln Asn Ala Thr Thr Phe Asp Gly Lys
100 105 110

Tyr Ala Phe Leu Lys Thr Tyr Asn Tyr Ser Leu Gly Ala Asp Asp Leu
115 120 125

Thr Pro Phe Gly Glu Gln Glu Leu Val Asn Ser Gly Ile Lys Phe Tyr
130 135 140

Gln Arg Tyr Glu Ser Leu Thr Arg Asn Ile Val Pro Phe Ile Arg Ser
145 150 155 160

Ser Gly Ser Ser Arg Val Ile Ala Ser Gly Lys Lys Phe Ile Glu Gly
165 170 175

Phe Gln Ser Thr Lys Leu Lys Asp Pro Arg Ala Gln Pro Gly Gln Ser
180 185 190

Ser Pro Lys Ile Asp Val Val Ile Ser Glu Ala Ser Ser Ser Asn Asn
195 200 205

Thr Leu Asp Pro Gly Thr Cys Thr Val Phe Glu Asp Ser Glu Leu Ala
210 215 220

Asp Thr Val Glu Ala Asn Phe Thr Ala Thr Phe Val Pro Ser Ile Arg
225 230 235 240

Gln Arg Leu Glu Asn Asp Leu Ser Gly Val Thr Leu Thr Asp Thr Glu
245 250 255

Val Thr Tyr Leu Met Asp Met Cys Ser Phe Asp Thr Ile Ser Thr Ser
260 265 270

Thr Val Asp Thr Lys Leu Ser Pro Phe Cys Asp Leu Phe Thr His Asp
275 280 285

Glu Trp Ile Asn Tyr Asp Tyr Leu Gln Ser Leu Lys Glu Tyr Tyr Gly
290 295 300

His Gly Ala Gly Asn Pro Leu Gly Pro Thr Gln Gly Val Gly Tyr Ala
305 310 315 320

Asn Glu Leu Ile Ala Arg Leu Thr His Ser Pro Val His Asp Asp Thr
325 330 335

Ser Ser Asn His Thr Leu Asp Ser Ser Pro Ala Thr Phe Pro Leu Asn
340 345 350

Ser Thr Leu Tyr Ala Asp Phe Ser His Asp Asn Gly Ile Ile Ser Ile
355 360 365

-continued

```
Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 35
<211> LENGTH: 2665
<212> TYPE: DNA
<213> ORGANISM: Aspergillus niger

<400> SEQUENCE: 35

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720

gtctgggtat gctaagcacc acaatcaaag tctaataagg accctccctt ccgagggccc     780

ctgaagctcg gactgtgtgg gactactgat cgctgactat ctgtgcagag tcacctccgg     840

actggcagtc cccgcctcga gaaatcaatc cagttgcgat acggtcgatc aggggtatca     900

atgcttctcc gagacttcgc atctttgggg tcaatacgca ccgttcttct ctctggcaaa     960

cgaatcggtc atctcccctg aggtgcccgc cggatgcaga gtcactttcg ctcaggtcct    1020

ctcccgtcat ggagcgcggt atccgaccga ctccaagggc aagaaatact ccgctctcat    1080

tgaggagatc cagcagaacg cgaccacctt tgacggaaaa tatgccttcc tgaagacata    1140

caactacagc ttgggtgcag atgacctgac tcccttcgga gaacaggagc tagtcaactc    1200

cggcatcaag ttctaccagc ggtacgaatc gctcacaagg aacatcgttc cattcatccg    1260

atcctctggc tccagccgcg tgatcgcctc cggcaagaaa ttcatcgagg gcttccagag    1320

caccaagctg aaggatcctc gtgcccagcc cggccaatcg tcgcccaaga tcgacgtggt    1380

catttccgag gccagctcat ccaacaacac tctcgaccca ggcacctgca ctgtcttcga    1440

agacagcgaa ttggccgata ccgtcgaagc caatttcacc gccacgttcg tcccctccat    1500
```

-continued

```
tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacgactacc tccagtcctt   1680

ggaagagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

<210> SEQ ID NO 36
<211> LENGTH: 467
<212> TYPE: PRT
<213> ORGANISM: Aspergillus niger

<400> SEQUENCE: 36

```
Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160
```

-continued

```
Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Glu Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 37
<211> LENGTH: 2665
<212> TYPE: DNA
<213> ORGANISM: Aspergillus niger

<400> SEQUENCE: 37

```
gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360
```

-continued

```
atgctggatc aacgatcaac ttgaatgcaa taaatgaaga tggaactaac accatctgct    420
gcctttctct cgagaaagct cctccacttc tcccactaga tatctccgtc cccgtcgact    480
tcccgtccta ttcggcctcg tccgctgaag atccatccca ccattgcacg tgggccacct    540
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcaaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
cccctctgt gacctgttca cccatgacga atggatcaac tacgactacc tccagtcctt   1680
ggataagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                         2665
```

-continued

<210> SEQ ID NO 38
<211> LENGTH: 467
<212> TYPE: PRT
<213> ORGANISM: Aspergillus niger

<400> SEQUENCE: 38

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Asp Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380
```

-continued

```
Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 39
<211> LENGTH: 2665
<212> TYPE: DNA
<213> ORGANISM: Aspergillus niger

<400> SEQUENCE: 39

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcaaagc caatttcacc gccacgttcg tcccctccat   1500

tcgtcaacgt ctggagaacg acctgtccgg tgtgactctc acagacacag aagtgaccta   1560
```

-continued cctcatggac atgtgctcct tcgacaccat ctccaccagc accgtcgaca ccaagctgtc 1620
ccccttctgt gacctgttca cccatgacga atggatcaac tacgactacc tccagtcctt 1680
gagaaagtat tacggccatg gtgcaggtaa cccgctcggc ccgacccagg gcgtcggcta 1740
cgctaacgag ctcatcgccc gtctgaccca ctcgcctgtc cacgatgaca ccagttccaa 1800
ccacactttg gactcgagcc cggctacctt tccgctcaac tctactctct acgcggactt 1860
ttcgcatgac aacggcatca tctccattct ctttgcttta ggtctgtaca acggcactaa 1920
gccgctatct accacgaccg tggagaatat cacccagaca gatggattct cgtctgcttg 1980
gacggttccg tttgcttcgc gtttgtacgt cgagatgatg cagtgtcagg cggagcagga 2040
gccgctggtc cgtgtcttgg ttaatgatcg cgttgtcccg ctgcatgggt gtccggttga 2100
tgctttgggg agatgtaccc gggatagctt tgtgaggggg ttgagctttg ctagatctgg 2160
gggtgattgg gcggagtgtt ttgcttagct gaattacctt gatgaatggt atgtatcagc 2220
attgcatatc attagcactt caggtatgta ttatcgaaga tgtatatcga aaggatcaat 2280
ggtgactgtc actggttatc tgaatatccc tctatacctc gcccacaacc aatcatcacc 2340
ctttaaacaa tcacactcaa gccacagcgt acaaacgaac aaacgcacaa agaatatttt 2400
acactcctcc ccaacgcaat accaaccgca attcatcata cctcatataa atacaataca 2460
atacaataca tccatcccta ccctcaagtc cacccatcct ataatcaatc cctacttact 2520
tacttctccc cctccccctc acccttccca gaactcaccc ccgaagtagt aatagtagta 2580
gtagaagaag cagacgacct ctccaccaat ctcttcggcc tcttatcccc atacgctaca 2640
caaaaccccc accccgttag catgc 2665

<210> SEQ ID NO 40
<211> LENGTH: 467
<212> TYPE: PRT
<213> ORGANISM: Aspergillus niger

<400> SEQUENCE: 40

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp
20 25 30

Thr Val Asp Gln Gly Tyr Gln Cys Phe Ser Glu Thr Ser His Leu Trp
35 40 45

Gly Gln Tyr Ala Pro Phe Phe Ser Leu Ala Asn Glu Ser Val Ile Ser
50 55 60

Pro Glu Val Pro Ala Gly Cys Arg Val Thr Phe Ala Gln Val Leu Ser
65 70 75 80

Arg His Gly Ala Arg Tyr Pro Thr Asp Ser Lys Gly Lys Lys Tyr Ser
85 90 95

Ala Leu Ile Glu Glu Ile Gln Gln Asn Ala Thr Thr Phe Asp Gly Lys
100 105 110

Tyr Ala Phe Leu Lys Thr Tyr Asn Tyr Ser Leu Gly Ala Asp Asp Leu
115 120 125

Thr Pro Phe Gly Glu Gln Glu Leu Val Asn Ser Gly Ile Lys Phe Tyr
130 135 140

Gln Arg Tyr Glu Ser Leu Thr Arg Asn Ile Val Pro Phe Ile Arg Ser
145 150 155 160

Ser Gly Ser Ser Arg Val Ile Ala Ser Gly Lys Lys Phe Ile Glu Gly
165 170 175

-continued

Phe Gln Ser Thr Lys Leu Lys Asp Pro Arg Ala Gln Pro Gly Gln Ser
180 185 190

Ser Pro Lys Ile Asp Val Val Ile Ser Glu Ala Ser Ser Ser Asn Asn
195 200 205

Thr Leu Asp Pro Gly Thr Cys Thr Val Phe Glu Asp Ser Glu Leu Ala
210 215 220

Asp Thr Val Lys Ala Asn Phe Thr Ala Thr Phe Val Pro Ser Ile Arg
225 230 235 240

Gln Arg Leu Glu Asn Asp Leu Ser Gly Val Thr Leu Thr Asp Thr Glu
245 250 255

Val Thr Tyr Leu Met Asp Met Cys Ser Phe Asp Thr Ile Ser Thr Ser
260 265 270

Thr Val Asp Thr Lys Leu Ser Pro Phe Cys Asp Leu Phe Thr His Asp
275 280 285

Glu Trp Ile Asn Tyr Asp Tyr Leu Gln Ser Leu Arg Lys Tyr Tyr Gly
290 295 300

His Gly Ala Gly Asn Pro Leu Gly Pro Thr Gln Gly Val Gly Tyr Ala
305 310 315 320

Asn Glu Leu Ile Ala Arg Leu Thr His Ser Pro Val His Asp Asp Thr
325 330 335

Ser Ser Asn His Thr Leu Asp Ser Ser Pro Ala Thr Phe Pro Leu Asn
340 345 350

Ser Thr Leu Tyr Ala Asp Phe Ser His Asp Asn Gly Ile Ile Ser Ile
355 360 365

Leu Phe Ala Leu Gly Leu Tyr Asn Gly Thr Lys Pro Leu Ser Thr Thr
370 375 380

Thr Val Glu Asn Ile Thr Gln Thr Asp Gly Phe Ser Ser Ala Trp Thr
385 390 395 400

Val Pro Phe Ala Ser Arg Leu Tyr Val Glu Met Met Gln Cys Gln Ala
405 410 415

Glu Gln Glu Pro Leu Val Arg Val Leu Val Asn Asp Arg Val Val Pro
420 425 430

Leu His Gly Cys Pro Val Asp Ala Leu Gly Arg Cys Thr Arg Asp Ser
435 440 445

Phe Val Arg Gly Leu Ser Phe Ala Arg Ser Gly Gly Asp Trp Ala Glu
450 455 460

Cys Phe Ala
465

<210> SEQ ID NO 41
<211> LENGTH: 2665
<212> TYPE: DNA
<213> ORGANISM: Aspergillus niger

<400> SEQUENCE: 41
gcatgcagca ctgtcagcaa ataaattgct ttgaatgatt ttctgcttct tctcatattg 60
ggctatagac actgccgtta tctgactttt aatgagcgag ggcgatgttc atcattcggc 120
gttctgttct tatgatttcc ccacgtcctt tcgggctttc ggcacagcaa aatagattgt 180
ttagcaggta cagaaacaac ttgatgacac atgcatccga gaatcttcag ccgtggaagc 240
attcatgtag atctttgcta agagaaatga tggcggccca gggcatccag gcaccttttc 300
caacggggaa cttccgccgt ccacgtgctc tgattcagcc aatcaagacg tcccacggca 360
atgctggatc aacgatcaac ttgaatgcaa taaatgaaga tggaactaac accatctgct 420

-continued

```
gcctttctct cgagaaagct cctccacttc tcccactaga tatctccgtc cccgtcgact    480
tcccgtccta ttcggcctcg tccgctgaag atccatccca ccattgcacg tgggccacct    540
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctccccctg aggtgcccgc cggatgcaga gtcactttcg ctcaggtcct   1020
ctcccgtcat ggagcgcggt atccgaccga ctccaagggc aaggaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcaaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
ccccttctgt gacctgttca cccatgacga atggatcaac tacgactacc tccagtcctt   1680
gaaaaagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                          2665
```

<210> SEQ ID NO 42
<211> LENGTH: 467

-continued

<212> TYPE: PRT
<213> ORGANISM: Aspergillus niger

<400> SEQUENCE: 42

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Glu Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400
```

-continued

```
Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 43
<211> LENGTH: 2665
<212> TYPE: DNA
<213> ORGANISM: Aspergillus niger

<400> SEQUENCE: 43

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcaaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

cccctctgt gacctgttca cccatgacga atggatcaac tacgactacc tccagtcctt   1680
```

-continued

```
gagagagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

```
<210> SEQ ID NO 44
<211> LENGTH: 467
<212> TYPE: PRT
<213> ORGANISM: Aspergillus niger

<400> SEQUENCE: 44

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190
```

-continued

```
Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Arg Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465


<210> SEQ ID NO 45
<211> LENGTH: 2665
<212> TYPE: DNA
<213> ORGANISM: Aspergillus niger

<400> SEQUENCE: 45

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540
```

-continued

```
ttgtgagctt ctaacctgaa ctggtagagt atcacacacc atgccaaggt gggatgaagg    600
ggttatatag gaccgtccgg tccggcgcga tggccgtagc tgccactcgc tgctgtgcaa    660
gaaattactt ctcataggca tcatgggcgt ctctgctgtt ctacttcctt tgtatctcct    720
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccaagggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtcaaagc caatttcacc gccacgttcg tccccctccat  1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
ccccttctgt gacctgttca cccatgacga atggatcaac tacgactacc tccagtcctt   1680
gacagagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                         2665
```

<210> SEQ ID NO 46
<211> LENGTH: 467
<212> TYPE: PRT
<213> ORGANISM: Aspergillus niger -continued

<400> SEQUENCE: 46

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Thr Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415
```

-continued

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465

<210> SEQ ID NO 47
<211> LENGTH: 2665
<212> TYPE: DNA
<213> ORGANISM: Aspergillus niger

<400> SEQUENCE: 47
gcatgcagca ctgtcagcaa ataaattgct ttgaatgatt ttctgcttct tctcatattg 60
ggctatagac actgccgtta tctgactttt aatgagcgag ggcgatgttc atcattcggc 120
gttctgttct tatgatttcc ccacgtcctt tcgggctttc ggcacagcaa aatagattgt 180
ttagcaggta cagaaacaac ttgatgacac atgcatccga gaatcttcag ccgtggaagc 240
attcatgtag atctttgcta agagaaatga tggcggccca gggcatccag gcaccttttc 300
caacggggaa cttccgccgt ccacgtgctc tgattcagcc aatcaagacg tcccacggca 360
atgctggatc aacgatcaac ttgaatgcaa taaatgaaga tggaactaac accatctgct 420
gcctttctct cgagaaagct cctccacttc tcccactaga tatctccgtc cccgtcgact 480
tcccgtccta ttcggcctcg tccgctgaag atccatccca ccattgcacg tgggccacct 540
ttgtgagctt ctaacctgaa ctggtagagt atcacacacc atgccaaggt gggatgaagg 600
ggttatatag gaccgtccgg tccggcgcga tggccgtagc tgccactcgc tgctgtgcaa 660
gaaattactt ctcataggca tcatgggcgt ctctgctgtt ctacttcctt tgtatctcct 720
gtctgggtat gctaagcacc acaatcaaag tctaataagg accctccctt ccgagggccc 780
ctgaagctcg gactgtgtgg gactactgat cgctgactat ctgtgcagag tcacctccgg 840
actggcagtc cccgcctcga gaaatcaatc cagttgcgat acggtcgatc aggggtatca 900
atgcttctcc gagacttcgc atctttgggg tcaatacgca ccgttcttct ctctggcaaa 960
cgaatcggtc atctcccctg aggtgcccgc cggatgcaga gtcactttcg ctcaggtcct 1020
ctcccgtcat ggagcgcggt atccgaccga ctccaagggc aagaaatact ccgctctcat 1080
tgaggagatc cagcagaacg cgaccacctt tgacggaaaa tatgccttcc tgaagacata 1140
caactacagc ttgggtgcag atgacctgac tcccttcgga gaacaggagc tagtcaactc 1200
cggcatcaag ttctaccagc ggtacgaatc gctcacaagg aacatcgttc cattcatccg 1260
atcctctggc tccagccgcg tgatcgcctc cggcaagaaa ttcatcgagg gcttccagag 1320
caccaagctg aaggatcctc gtgcccagcc cggccaatcg tcgcccaaga tcgacgtggt 1380
catttccgag gccagctcat ccaacaacac tctcgaccca ggcacctgca ctgtcttcga 1440
agacagcgaa ttggccgata ccgtcaaagc caatttcacc gccacgttcg tcccctccat 1500
tcgtcaacgt ctggagaacg acctgtccgg tgtgactctc acagacacag aagtgaccta 1560
cctcatggac atgtgctcct tcgacaccat ctccaccagc accgtcgaca ccaagctgtc 1620 cccttctgt gacctgttca cccatgacga atggatcaac tacgactacc tccagtcctt 1680
ggatgagtat tacggccatg gtgcaggtaa cccgctcggc ccgacccagg gcgtcggcta 1740

-continued

```
cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

```
<210> SEQ ID NO 48
<211> LENGTH: 467
<212> TYPE: PRT
<213> ORGANISM: Aspergillus niger

<400> SEQUENCE: 48

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205
```

-continued

```
Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Asp Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 49
<211> LENGTH: 2665
<212> TYPE: DNA
<213> ORGANISM: Aspergillus niger

<400> SEQUENCE: 49

```
gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600
```

-continued

```
ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aaggaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcgaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

cccttctgt gacctgttca cccatgacga atggatcaac tacgactacc tccagtcctt   1680

ggaagagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctcccctc accctccca gaactcaccc ccgaagtagt aatagtagta   2580

gtagaagaag cagacgacct ctccaccaat ctcttcggcc tcttatcccc atacgctaca   2640

caaaaccccc accccgttag catgc                                           2665
```

<210> SEQ ID NO 50
<211> LENGTH: 467
<212> TYPE: PRT
<213> ORGANISM: Aspergillus niger

<400> SEQUENCE: 50

Met Gly Val Ser Ala Val Leu Leu Pro Leu Tyr Leu Leu Ser Gly Val

-continued

```
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Glu Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Glu Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430
```

-continued

```
Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 51
<211> LENGTH: 2665
<212> TYPE: DNA
<213> ORGANISM: Aspergillus niger

<400> SEQUENCE: 51

```
gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aaggaatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcaaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

cccctttctgt gacctgttca cccatgacga atggatcaac tacgactacc tccagtcctt   1680

gaaagagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860
```

-continued

```
ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

```
<210> SEQ ID NO 52
<211> LENGTH: 467
<212> TYPE: PRT
<213> ORGANISM: Aspergillus niger

<400> SEQUENCE: 52

Met Gly Val Ser Ala Val Leu Leu Pro Leu Tyr Leu Leu Ser Gly Val
1               5                   10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Glu Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220
```

-continued

```
Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Glu Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465

<210> SEQ ID NO 53
<211> LENGTH: 2665
<212> TYPE: DNA
<213> ORGANISM: Aspergillus niger

<400> SEQUENCE: 53

gcatgcagca ctgtcagcaa ataaattgct ttgaatgatt ttctgcttct tctcatattg      60

ggctatagac actgccgtta tctgactttt aatgagcgag ggcgatgttc atcattcggc     120

gttctgttct tatgatttcc ccacgtcctt tcgggctttc ggcacagcaa aatagattgt     180

ttagcaggta cagaaacaac ttgatgacac atgcatccga gaatcttcag ccgtggaagc     240

attcatgtag atctttgcta agagaaatga tggcggccca gggcatccag gcaccttttc     300

caacggggaa cttccgccgt ccacgtgctc tgattcagcc aatcaagacg tcccacggca     360

atgctggatc aacgatcaac ttgaatgcaa taaatgaaga tggaactaac accatctgct     420

gcctttctct cgagaaagct cctccacttc tcccactaga tatctccgtc cccgtcgact     480

tcccgtccta ttcggcctcg tccgctgaag atccatccca ccattgcacg tgggccacct     540

ttgtgagctt ctaacctgaa ctggtagagt atcacacacc atgccaaggt gggatgaagg     600

ggttatatag gaccgtccgg tccggcgcga tggccgtagc tgccactcgc tgctgtgcaa     660

gaaattactt ctcataggca tcatgggcgt ctctgctgtt ctacttcctt tgtatctcct     720
```

-continued

```
gtctgggtat gctaagcacc acaatcaaag tctaataagg accctccctt ccgagggccc    780
ctgaagctcg gactgtgtgg gactactgat cgctgactat ctgtgcagag tcacctccgg    840
actggcagtc cccgcctcga gaaatcaatc cagttgcgat acggtcgatc aggggtatca    900
atgcttctcc gagacttcgc atctttgggg tcaatacgca ccgttcttct ctctggcaaa    960
cgaatcggtc atctcccctg aggtgcccgc cggatgcaga gtcactttcg ctcaggtcct   1020
ctcccgtcat ggagcgcggt atccgaccga ctccgcgggc aagaaatact ccgctctcat   1080
tgaggagatc cagcagaacg cgaccacctt tgacggaaaa tatgccttcc tgaagacata   1140
caactacagc ttgggtgcag atgacctgac tcccttcgga gaacaggagc tagtcaactc   1200
cggcatcaag ttctaccagc ggtacgaatc gctcacaagg aacatcgttc cattcatccg   1260
atcctctggc tccagccgcg tgatcgcctc cggcaagaaa ttcatcgagg gcttccagag   1320
caccaagctg aaggatcctc gtgcccagcc cggccaatcg tcgcccaaga tcgacgtggt   1380
catttccgag gccagctcat ccaacaacac tctcgaccca ggcacctgca ctgtcttcga   1440
agacagcgaa ttggccgata ccgtccaagc caatttcacc gccacgttcg tcccctccat   1500
tcgtcaacgt ctggagaacg acctgtccgg tgtgactctc acagacacag aagtgaccta   1560
cctcatggac atgtgctcct tcgacaccat ctccaccagc accgtcgaca ccaagctgtc   1620
cccctttctgt gacctgttca cccatgacga atggatcaac tacgactacc tccagtcctt   1680
ggaaaagtat tacggccatg gtgcaggtaa cccgctcggc ccgacccagg gcgtcggcta   1740
cgctaacgag ctcatcgccc gtctgaccca ctcgcctgtc cacgatgaca ccagttccaa   1800
ccacactttg gactcgagcc cggctacctt tccgctcaac tctactctct acgcggactt   1860
ttcgcatgac aacggcatca tctccattct ctttgcttta ggtctgtaca acggcactaa   1920
gccgctatct accacgaccg tggagaatat cacccagaca gatggattct cgtctgcttg   1980
gacggttccg tttgcttcgc gtttgtacgt cgagatgatg cagtgtcagg cggagcagga   2040
gccgctggtc cgtgtcttgg ttaatgatcg cgttgtcccg ctgcatgggt gtccggttga   2100
tgctttgggg agatgtaccc gggatagctt tgtgaggggg ttgagctttg ctagatctgg   2160
gggtgattgg gcggagtgtt ttgcttagct gaattacctt gatgaatggt atgtatcagc   2220
attgcatatc attagcactt caggtatgta ttatcgaaga tgtatatcga aaggatcaat   2280
ggtgactgtc actggttatc tgaatatccc tctatacctc gcccacaacc aatcatcacc   2340
ctttaaacaa tcacactcaa gccacagcgt acaaacgaac aaacgcacaa agaatatttt   2400
acactcctcc ccaacgcaat accaaccgca attcatcata cctcatataa atacaataca   2460
atacaataca tccatcccta ccctcaagtc cacccatcct ataatcaatc cctacttact   2520
tacttctccc cctccccctc acccttccca gaactcaccc ccgaagtagt aatagtagta   2580
gtagaagaag cagacgacct ctccaccaat ctcttcggcc tcttatcccc atacgctaca   2640
caaaaccccc accccgttag catgc                                         2665
```

<210> SEQ ID NO 54
<211> LENGTH: 467
<212> TYPE: PRT
<213> ORGANISM: Aspergillus niger

<400> SEQUENCE: 54

```
Met Gly Val Ser Ala Val Leu Leu Pro Leu Tyr Leu Leu Ser Gly Val
 1               5                  10                  15

Thr Ser Gly Leu Ala Val Pro Ala Ser Arg Asn Gln Ser Ser Cys Asp
```

-continued

```
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Ala Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Gln Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Glu Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445
```

-continued

```
Phe Val Arg Gly Leu Ser Phe Ala Arg Ser Gly Gly Asp Trp Ala Glu
    450                 455                 460

Cys Phe Ala
465


<210> SEQ ID NO 55
<211> LENGTH: 2665
<212> TYPE: DNA
<213> ORGANISM: Aspergillus niger

<400> SEQUENCE: 55

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aaggcatact ccgctctcat   1080

tgaggagatc cagcagaacg cgaccacctt tgacggaaaa tatgccttcc tgaagacata   1140

caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcgcagc caatttcacc gccacgttcg tcccctccat   1500

tcgtcaacgt ctggagaacg acctgtccgg tgtgactctc acagacacag aagtgaccta   1560

cctcatggcc atgtgctcct tcgacaccat ctccaccagc accgtcgaca ccaagctgtc   1620

ccccttctgt gacctgttca cccatgacga atggatcaac tacgactacc tccagtcctt   1680

ggataagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920
```

-continued

```
gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                          2665
```

<210> SEQ ID NO 56
<211> LENGTH: 467
<212> TYPE: PRT
<213> ORGANISM: Aspergillus niger

<400> SEQUENCE: 56

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Ala Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Ala Ala Asn Phe Thr Ala Thr Phe Val Pro Ser Ile Arg
225                 230                 235                 240
```

-continued

```
Gln Arg Leu Glu Asn Asp Leu Ser Gly Val Thr Leu Thr Asp Thr Glu
                245                 250                 255

Val Thr Tyr Leu Met Ala Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Asp Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence:
Oligonucleotide for generating site-specific
insertions

<400> SEQUENCE: 57
ctttggggtc tatacgcacc g 21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence:
Oligonucleotide for generating site-specific
insertions

<400> SEQUENCE: 58
ctttggggtc catacgcacc g 21

<210> SEQ ID NO 59
<211> LENGTH: 27
<212> TYPE: DNA
<213> ORGANISM: Artificial Sequence
<220> FEATURE:

-continued

<223> OTHER INFORMATION: Description of Artificial Sequence:
      Oligonucleotide for generating site-specific
      insertions

<400> SEQUENCE: 59
cacgacaaca gcctggtttc catcttc 27

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 60
gcgaattctc caagtcctgc gatac 25

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 61
acatctagac taaagcactc tcc 23

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide for generating site-specific
      insertions

<400> SEQUENCE: 62
ctccagtcct tggaaaagta ttacg 25

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide for generating site-specific
      insertions

<400> SEQUENCE: 63
ctccagtcct tggataagta ttacggc 27

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide for generating site-specific
      insertions

<400> SEQUENCE: 64
ctccagtcct tgagaaagta ttacggc 27

<210> SEQ ID NO 65
<211> LENGTH: 27
<212> TYPE: DNA
<213> ORGANISM: Artificial Sequence -continued

```
<220> FEATURE:
<223> OTHER INFORMATION: Description of Artificial Sequence:
      Oligonucleotide for generating site-specific
      insertions

<400> SEQUENCE: 65

ctccagtcct tgacaaagta ttacggc                                        27


<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 66

cggaattcct ggcagtcccc g                                              21


<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 67

gctctagact aagcaaaaca ctcc                                           24


<210> SEQ ID NO 68
<211> LENGTH: 2665
<212> TYPE: DNA
<213> ORGANISM: Aspergillus niger

<400> SEQUENCE: 68

gcatgcagca ctgtcagcaa ataaattgct ttgaatgatt ttctgcttct tctcatattg     60

ggctatagac actgccgtta tctgactttt aatgagcgag ggcgatgttc atcattcggc    120

gttctgttct tatgatttcc ccacgtcctt tcgggctttc ggcacagcaa aatagattgt    180

ttagcaggta cagaaacaac ttgatgacac atgcatccga gaatcttcag ccgtggaagc    240

attcatgtag atctttgcta agagaaatga tggcggccca gggcatccag gcaccttttc    300

caacggggaa cttccgccgt ccacgtgctc tgattcagcc aatcaagacg tcccacggca    360

atgctggatc aacgatcaac ttgaatgcaa taaatgaaga tggaactaac accatctgct    420

gcctttctct cgagaaagct cctccacttc tcccactaga tatctccgtc cccgtcgact    480

tcccgtccta ttcggcctcg tccgctgaag atccatccca ccattgcacg tgggccacct    540

ttgtgagctt ctaacctgaa ctggtagagt atcacacacc atgccaaggt gggatgaagg    600

ggttatatag gaccgtccgg tccggcgcga tggccgtagc tgccactcgc tgctgtgcaa    660

gaaattactt ctcataggca tcatgggcgt ctctgctgtt ctacttcctt tgtatctcct    720

gtctgggtat gctaagcacc acaatcaaag tctaataagg accctccctt ccgagggccc    780

ctgaagctcg gactgtgtgg gactactgat cgctgactat ctgtgcagag tcacctccgg    840

actggcagtc cccgcctcga gaaatcaatc cagttgcgat acggtcgatc aggggtatca    900

atgcttctcc gagacttcgc atctttgggg tcaatacgca ccgttcttct ctctggcaaa    960

cgaatcggtc atctcccctg aggtgcccgc cggatgcaga gtcactttcg ctcaggtcct   1020

ctcccgtcat ggagcgcggt atccgaccga ctccaagggc aagaaatact ccgctctcat   1080

tgaggagatc cagcagaacg cgaccacctt tgacggaaaa tatgccttcc tgaagacata   1140
```

-continued

```
caactacagc ttgggtgcag atgacctgac tcccttcgga gaacaggagc tagtcaactc   1200

cggcatcaag ttctaccagc ggtacgaatc gctcacaagg aacatcgttc cattcatccg   1260

atcctctggc tccagccgcg tgatcgcctc cggcaagaaa ttcatcgagg gcttccagag   1320

caccaagctg aaggatcctc gtgcccagcc cggccaatcg tcgcccaaga tcgacgtggt   1380

catttccgag gccagctcat ccaacaacac tctcgaccca ggcacctgca ctgtcttcga   1440

agacagcgaa ttggccgata ccgtcaaagc caatttcacc gccacgttcg tcccctccat   1500

tcgtcaacgt ctggagaacg acctgtccgg tgtgactctc acagacacag aagtgaccta   1560

cctcatggac atgtgctcct tcgacaccat ctccaccagc accgtcgaca ccaagctgtc   1620

ccccttctgt gacctgttca cccatgacga atggatcaac tacgactacc tccagtcctt   1680

gacaaagtat tacggccatg gtgcaggtaa cccgctcggc ccgacccagg gcgtcggcta   1740

cgctaacgag ctcatcgccc gtctgaccca ctcgcctgtc cacgatgaca ccagttccaa   1800

ccacactttg gactcgagcc cggctacctt tccgctcaac tctactctct acgcggactt   1860

ttcgcatgac aacggcatca tctccattct ctttgcttta ggtctgtaca acggcactaa   1920

gccgctatct accacgaccg tggagaatat cacccagaca gatggattct cgtctgcttg   1980

gacggttccg tttgcttcgc gtttgtacgt cgagatgatg cagtgtcagg cggagcagga   2040

gccgctggtc cgtgtcttgg ttaatgatcg cgttgtcccg ctgcatgggt gtccggttga   2100

tgctttgggg agatgtaccc gggatagctt tgtgaggggg ttgagctttg ctagatctgg   2160

gggtgattgg gcggagtgtt ttgcttagct gaattacctt gatgaatggt atgtatcagc   2220

attgcatatc attagcactt caggtatgta ttatcgaaga tgtatatcga aaggatcaat   2280

ggtgactgtc actggttatc tgaatatccc tctatacctc gcccacaacc aatcatcacc   2340

ctttaaacaa tcacactcaa gccacagcgt acaaacgaac aaacgcacaa agaatatttt   2400

acactcctcc ccaacgcaat accaaccgca attcatcata cctcatataa atacaataca   2460

atacaataca tccatcccta ccctcaagtc cacccatcct ataatcaatc cctacttact   2520

tacttctccc cctccccctc acccttccca gaactcaccc ccgaagtagt aatagtagta   2580

gtagaagaag cagacgacct ctccaccaat ctcttcggcc tcttatcccc atacgctaca   2640

caaaaccccc accccgttag catgc                                         2665
```

<210> SEQ ID NO 69
<211> LENGTH: 467
<212> TYPE: PRT
<213> ORGANISM: Aspergillus niger

<400> SEQUENCE: 69

```
Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
```

-continued

```
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Lys Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Thr Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465
```